United States Patent
Itoi et al.

(10) Patent No.: US 10,593,885 B2
(45) Date of Patent: Mar. 17, 2020

(54) POLYCYCLIC COMPOUND AND ORGANIC ELECTROLUMINESCENCE DEVICE INCLUDING THE SAME

(71) Applicant: Samsung Display Co., Ltd., Yongin-si, Gyeonggi-do (KR)

(72) Inventors: Hiroaki Itoi, Yokohama (JP); Hideo Miyake, Yokohama (JP); Hisayuki Kawamura, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/368,358

(22) Filed: Dec. 2, 2016

(65) Prior Publication Data

US 2017/0324037 A1 Nov. 9, 2017

(30) Foreign Application Priority Data

May 9, 2016 (KR) ........................ 10-2016-0056626

(51) Int. Cl.
*H01L 51/00* (2006.01)
*C07C 211/58* (2006.01)
(Continued)

(52) U.S. Cl.
CPC ............ *H01L 51/006* (2013.01); *C07C 13/66* (2013.01); *C07C 211/54* (2013.01);
(Continued)

(58) Field of Classification Search
None
See application file for complete search history.

(56) References Cited

U.S. PATENT DOCUMENTS

2004/0219386 A1 11/2004 Thorns
2007/0290610 A1 12/2007 Park et al.
(Continued)

FOREIGN PATENT DOCUMENTS

EP 2365555 A2 9/2011
JP 8-259937 A 10/1996
(Continued)

OTHER PUBLICATIONS

Machine English translation of Mujica-Fernaud et al. (WO 2016/087017 A1). Feb. 4, 2018.*
(Continued)

*Primary Examiner* — Jay Yang
(74) *Attorney, Agent, or Firm* — Lewis Roca Rothgerber Christie LLP

(57) ABSTRACT

A polycyclic compound according to an embodiment of the inventive concept is represented by the following Formula 1:

Formula 1

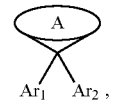

In Formula 1, $Ar_1$ and $Ar_2$ are each independently substituted or unsubstituted aryl group having 6 to 30 carbon atoms for forming a ring, or substituted or unsubstituted heteroaryl group having 2 to 30 carbon atoms for forming a ring, where $Ar_1$ and $Ar_2$ may combine with each other to form a ring, and A is represented by the following Formula 2-1 or 2-2:
(Continued)

Formula 2-1

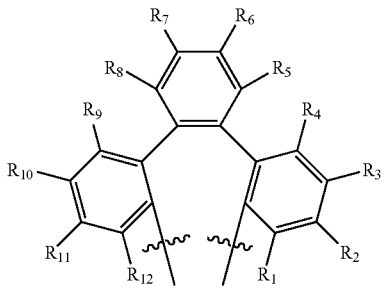

Formula 2-2

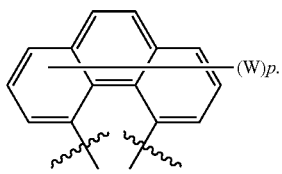

8 Claims, 1 Drawing Sheet

(51) Int. Cl.
C07C 211/61 (2006.01)
C07D 221/20 (2006.01)
C07D 307/93 (2006.01)
C09K 11/06 (2006.01)
C07C 255/52 (2006.01)
C07C 255/61 (2006.01)
C07D 335/12 (2006.01)
C07F 7/08 (2006.01)
C07F 9/6578 (2006.01)
C07C 13/66 (2006.01)
C07C 211/54 (2006.01)
C07D 311/96 (2006.01)
C07D 335/04 (2006.01)
C07D 491/06 (2006.01)
C09K 11/02 (2006.01)
H01L 51/50 (2006.01)

(52) U.S. Cl.
CPC .......... C07C 211/58 (2013.01); C07C 211/61 (2013.01); C07C 255/52 (2013.01); C07C 255/61 (2013.01); C07D 221/20 (2013.01); C07D 307/93 (2013.01); C07D 311/96 (2013.01); C07D 335/04 (2013.01); C07D 335/12 (2013.01); C07D 491/06 (2013.01); C07F 7/081 (2013.01); C07F 7/0814 (2013.01); C07F 9/6578 (2013.01); C09K 11/025 (2013.01); C09K 11/06 (2013.01); H01L 51/0061 (2013.01); H01L 51/0071 (2013.01); H01L 51/0072 (2013.01); H01L 51/0073 (2013.01); H01L 51/0074 (2013.01); C07C 2603/24 (2017.05); C07C 2603/26 (2017.05); C07C 2603/40 (2017.05); C07C 2603/48 (2017.05); C07C 2603/50 (2017.05); C07C 2603/94 (2017.05); C09K 2211/1007 (2013.01); C09K 2211/1011 (2013.01); C09K 2211/1014 (2013.01); C09K 2211/1029 (2013.01); C09K 2211/1033 (2013.01); C09K 2211/1037 (2013.01); C09K 2211/1044 (2013.01); C09K 2211/1059 (2013.01); C09K 2211/1088 (2013.01); C09K 2211/1092 (2013.01); H01L 51/0054 (2013.01); H01L 51/0058 (2013.01); H01L 51/0067 (2013.01); H01L 51/5012 (2013.01); H01L 51/5016 (2013.01); H01L 51/5056 (2013.01)

(56) References Cited

U.S. PATENT DOCUMENTS

| | | | |
|---|---|---|---|
| 2008/0079356 A1 | 4/2008 | Park et al. | |
| 2008/0093987 A1 | 4/2008 | Park et al. | |
| 2008/0100207 A1 | 5/2008 | Park et al. | |
| 2009/0117404 A1 | 5/2009 | Park et al. | |
| 2013/0328021 A1 | 12/2013 | Lim et al. | |
| 2014/0183422 A1* | 7/2014 | Stoessel | C07F 15/0086 252/519.2 |
| 2015/0115239 A1 | 4/2015 | Pflumm et al. | |
| 2015/0349265 A1 | 12/2015 | Hwang et al. | |
| 2016/0301010 A1 | 10/2016 | Park | |

FOREIGN PATENT DOCUMENTS

| | | |
|---|---|---|
| JP | 2009-267255 | 11/2009 |
| JP | 5747555 | 7/2015 |
| KR | 10-0718104 | 5/2007 |
| KR | 10-2014-0096372 | 8/2014 |
| KR | 10-2014-0119642 | 10/2014 |
| KR | 10-1473306 | 12/2014 |
| KR | 10-2015-0019724 | 2/2015 |
| WO | WO-2013/020631 A1 * | 2/2013 |
| WO | WO 2013/020631 A1 | 2/2013 |
| WO | WO 2013/135352 A1 | 9/2013 |
| WO | WO 2016/087017 A1 | 6/2016 |

OTHER PUBLICATIONS

Wei, Yi, et al., "Emission Mechanism of Doubly ortho-Linked Quinoxaline/Diphenylfluorene or cis-Stilbene/Fluorene Hybrid Compounds Based on the Transient Absorption and Emission Measurements during Pulse Radiolysis," Journal of the American chemical Society, vol. 131, No. 19, 2009, pp. 6698-6707.
Wittig, Georg, et al. "Vom o-Terphenylen-quecksilber zum 1-Phenyl-tribenzo-cyclo-heptatrienyl-Radikal," Chemische Berichte, vol. 95, 1962, pp. 431-442; DOI: 10.1002/cber.19620950220.
EPO Partial Search Report dated Aug. 22, 2017, for corresponding European Patent Application No. 17164008.9 (15 pages).
Kimura, Takao, et al., "Michael Addition of 4H-Cyclopenta[def]phenanthrene to 9,9'-Bifluorenylidene and the Related Reactions," Bulletin of the Chemical Society of Japan, vol. 52, No. 5, May 1979, pp. 1447-1449.
EPO Extended Search Report dated Dec. 8, 2017, for corresponding European Patent Application No. 17164008.9 (18 pages).

* cited by examiner

POLYCYCLIC COMPOUND AND ORGANIC ELECTROLUMINESCENCE DEVICE INCLUDING THE SAME

CROSS-REFERENCE TO RELATED APPLICATIONS

This patent application claims priority to and the benefit of Korean Patent Application No. 10-2016-0056626, filed on May 9, 2016 in the Korean Intellectual Property Office (KIPO), the contents of which are incorporated herein by reference.

BACKGROUND

1. Field

One or more aspects of embodiments of the present disclosure herein relate to a polycyclic compound and an organic electroluminescence device including the same.

2. Description of the Related Art

Recently, the development of an organic electroluminescence display as an image display is being actively conducted. The organic electroluminescence display is different from a liquid crystal display in that it is a self-luminescent display capable of displaying images via the recombination of holes and electrons injected from a first electrode and a second electrode into an emission layer and the light emission via a luminescent material including an organic compound in the emission layer.

An example organic electroluminescence device includes, for example, a first electrode, a hole transport layer disposed (e.g., positioned) on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected to the emission layer recombine to produce excitons in the emission layer. The organic electroluminescence device emits light generated by the radiation deactivation of the excitons. However, an embodiment of the organic electroluminescence device is not limited thereto, and various modifications may be possible.

For the application of an organic electroluminescence device in a display device, the organic electroluminescence device having high emission efficiency and long life is required, and developments of a material for an organic electroluminescence device capable of accomplishing these properties are being continuously required.

SUMMARY

One or more aspects of embodiments of the present disclosure are directed toward a polycyclic compound and an organic electroluminescence device including the same. More particularly, one or more aspects of embodiments of the present disclosure are directed toward a polycyclic compound which may increase emission efficiency and/or life of an organic electroluminescence device, and an organic electroluminescence device including the same.

An embodiment of the inventive concept provides a polycyclic compound represented by the following Formula 1:

Formula 1

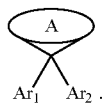

In Formula 1, $Ar_1$ and $Ar_2$ may each independently be substituted or unsubstituted aryl group having 6 to 30 carbon atoms for forming a ring, or substituted or unsubstituted heteroaryl group having 2 to 30 carbon atoms for forming a ring, where $Ar_1$ and $Ar_2$ optionally combine with each other to form a ring, and A may be represented by the following Formula 2-1 or 2-2:

[Formula 2-1]

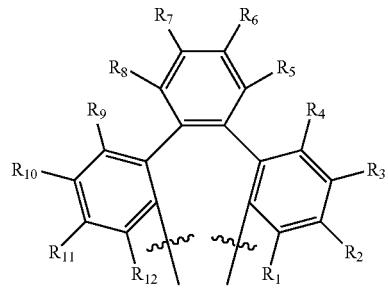

[Formula 2-2]

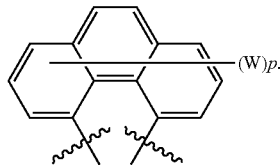

In Formula 2-1, $R_1$ to $R_{12}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, where adjacent groups optionally combine with each other to form a ring, and in Formula 2-2, W may be selected from hydrogen, deuterium, halogen, silyl group, substituted or unsubstituted alkyl group having 1 to 20 carbon atoms, substituted or unsubstituted aryl group having 6 to 60 carbon atoms for forming a ring, and substituted or unsubstituted heteroaryl group having 5 to 60 carbon atoms for forming a ring; and p may be an integer from 0 to 8. In the case where p is 2 or more, a plurality of W may be the same as or different from each other.

In an embodiment, the polycyclic compound of Formula 1 may be represented by the following Formula 3:

Formula 3

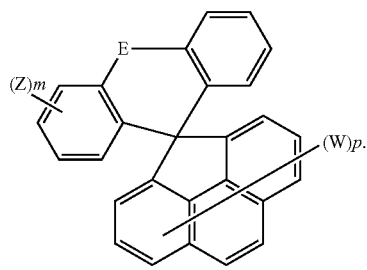

In Formula 3, W and p may be the same as described above, E may be O, S, or NR', m may be 0 or 1, and Z and R' may each independently be represented by the following Formula 4:

Formula 4

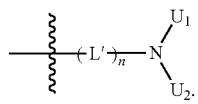

In Formula 4, $U_1$ and $U_2$ may each independently be substituted or unsubstituted aryl group having 6 to 30 carbon atoms for forming a ring, or substituted or unsubstituted heteroaryl group having 2 to 30 carbon atoms for forming a ring, L' may be substituted or unsubstituted arylene group having 6 to 30 carbon atoms for forming a ring, and n may be 0 or 1. In the case where E is NR', m may be 0, and in the case where E is O or S, m may be 1.

In an embodiment, the compound of Formula 3 may be represented by the following Formula 5:

Formula 5

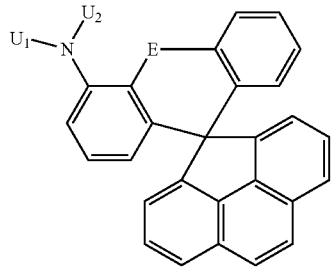

In Formula 5, E, $U_1$ and $U_2$ may be the same as described above.

In an embodiment, A in Formula 1 may be represented by Formula 2-1, and $Ar_1$ and $Ar_2$ may each independently be selected from substituted or unsubstituted phenyl group, substituted or unsubstituted anthracenyl group, substituted or unsubstituted pyrenyl group, substituted or unsubstituted phenanthryl group, substituted or unsubstituted chrysenyl group, substituted or unsubstituted triphenylenyl group, substituted or unsubstituted carbazolyl group, and substituted or unsubstituted pyridyl group, where $Ar_1$ and $Ar_2$ optionally combine with each other to form a ring.

In an embodiment, the polycyclic compound of Formula 1 may be represented by the following Formula 6:

Formula 6

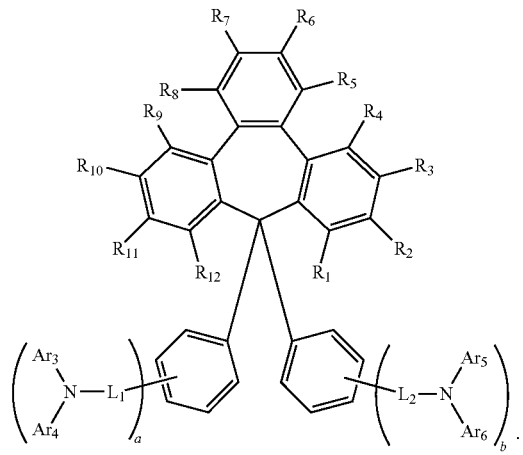

In Formula 6, $L_1$ and $L_2$ may each independently be selected from a direct linkage, substituted or unsubstituted arylene group having 6 to 30 carbon atoms for forming a ring, and substituted or unsubstituted heteroarylene group having 2 to 30 carbon atoms for forming a ring; $Ar_3$ to $Ar_6$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; a and b may each independently be 0 or 1, where the sum of a and b is not 0 (a+b≠0); and $R_1$ to $R_{12}$ may be the same as described above.

In an embodiment, the polycyclic compound of Formula 1 may be represented by the following Formula 7:

Formula 7

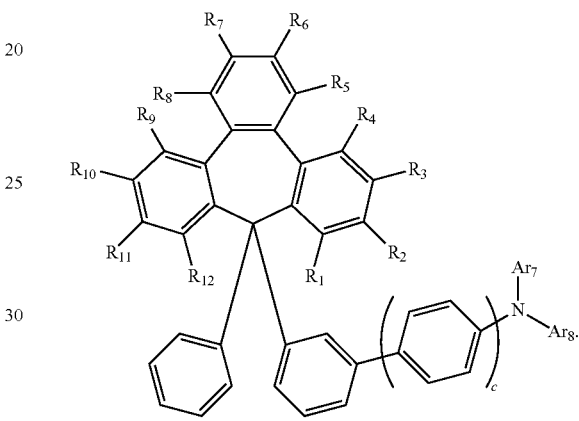

In Formula 7, $Ar_7$ and $Ar_8$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; c may be 0 or 1; and $R_1$ to $R_{12}$ may be the same as described above.

In an embodiment, the polycyclic compound of Formula 1 may be represented by the following Formula 8:

Formula 8

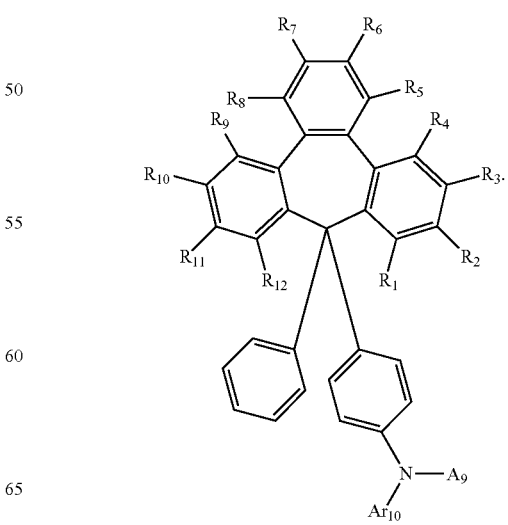

In Formula 8, $Ar_9$ and $Ar_{10}$ may each independently be hydrogen, deuterium, substituted or unsubstituted aryl group having 6 to 30 carbon atoms for forming a ring, and substituted or unsubstituted heteroaryl group having 2 to 30 carbon atoms for forming a ring; and $R_1$ to $R_{12}$ may be the same as described above.

In an embodiment, the polycyclic compound of Formula 1 may be represented by the following Formula 9:

Formula 9

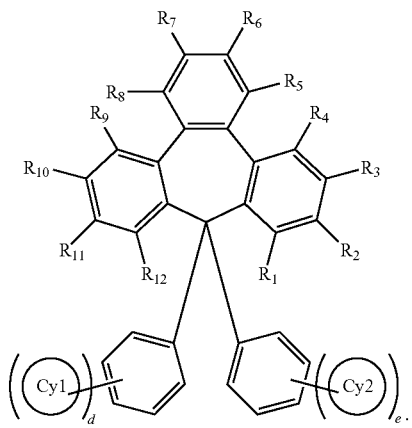

In Formula 9, Cy1 and Cy2 may each independently be substituted or unsubstituted heteroaryl group including 1 to 3 N atoms as heteroatoms and having 2 to 30 carbon atoms for forming a ring; d and e may each independently be 0 or 1, where the sum of d and e is not 0 (d+e≠0); and $R_1$ to $R_{12}$ may be the same as described above.

In an embodiment, the polycyclic compound of Formula 1 may be represented by the following Formula 10:

Formula 10

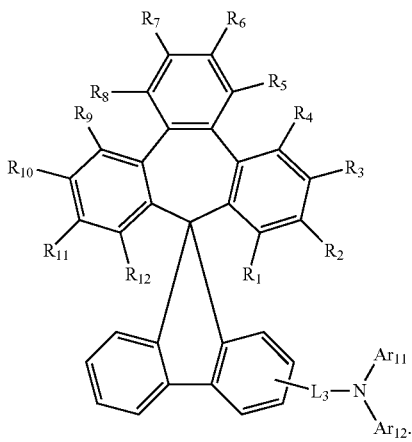

In Formula 10, $Ar_{11}$ and $Ar_{12}$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; $L_3$ may be selected from a direct linkage, substituted or unsubstituted arylene group having 6 to 30 carbon atoms for forming a ring, and substituted or unsubstituted heteroarylene group having 2 to 30 carbon atoms for forming a ring; and $R_1$ to $R_{12}$ may be the same as described above.

In an embodiment, the polycyclic compound of Formula 1 may be represented by the following Formula 11:

Formula 11

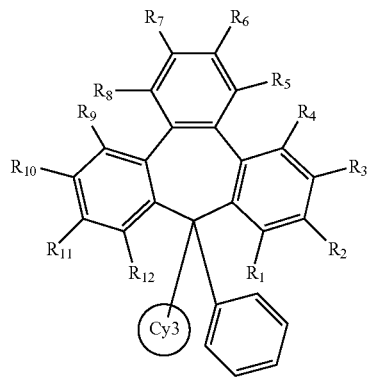

In Formula 11, Cy3 may be substituted or unsubstituted aryl group having a three- or four-membered ring; and $R_1$ to $R_{12}$ may be the same as described above.

In an embodiment, the polycyclic compound of Formula 1 may be represented by the following Formula 12:

Formula 12

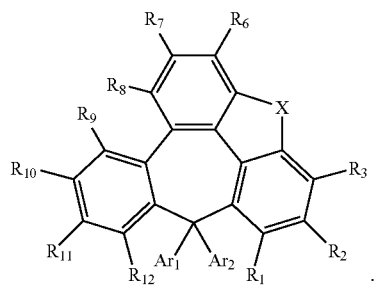

In Formula 12, X may be O, S, $NR_{13}$, $CR_{14}R_{15}$, or $SiR_{16}R_{17}$; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; and $Ar_1$, $Ar_2$, $R_1$ to $R_3$, and $R_6$ to $R_{12}$ may be the same as described above.

In an embodiment, the polycyclic compound of Formula 1 may be represented by the following Formula 13:

Formula 13

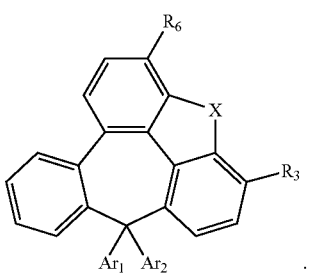

In Formula 13, X may be O, S, $NR_{13}$, $CR_{14}R_{15}$, or $SiR_{16}R_{17}$; $R_3$ and $R_6$ may each independently be selected from substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; and $Ar_1$ and $Ar_2$ may be the same as described above.

In an embodiment, the polycyclic compound of Formula 1 may be represented by the following Formula 14:

Formula 14

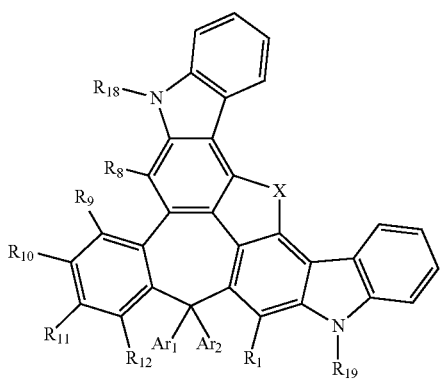

In Formula 14, X may be O, S, $NR_{13}$, $CR_{14}R_{15}$, or $SiR_{16}R_{17}$; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; $R_{18}$ and $R_{19}$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; and $Ar_1$, $Ar_2$, $R_1$, and $R_8$ to $R_{12}$ may be the same as described above.

In an embodiment, the polycyclic compound of Formula 1 may be represented by the following Formula 15:

Formula 15

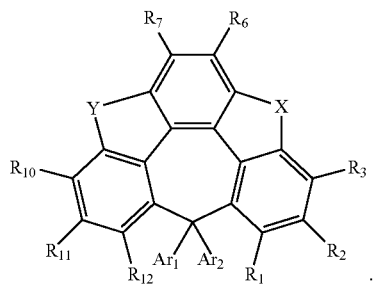

In Formula 15, X may be O, S, $NR_{13}$, $CR_{14}R_{15}$, or $SiR_{16}R_{17}$; Y may be O, S, $NR_{20}$, or substituted or unsubstituted phosphine oxide; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; $R_{20}$ may be selected from hydrogen, deuterium, substituted or unsubstituted aryl group having 6 to 30 carbon atoms for forming a ring, and substituted or unsubstituted heteroaryl group having 2 to 30 carbon atoms for forming a ring; and $Ar_1$, $Ar_2$, $R_1$ to $R_3$, $R_6$, $R_7$, and $R_{10}$ to $R_{12}$ may be the same as described above.

In an embodiment, the polycyclic compound of Formula 1 may be represented by the following Formula 16:

Formula 16

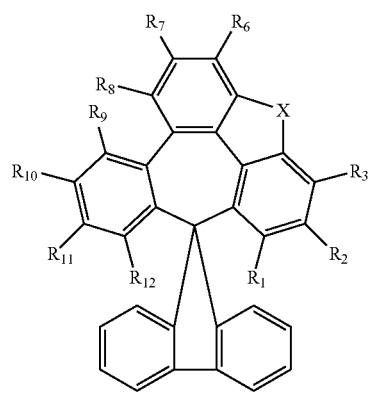

In Formula 16, X may be O, S, $NR_{13}$, $CR_{14}R_{15}$, or $SiR_{16}R_{17}$; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; and $R_1$ to $R_3$ and $R_6$ to $R_{12}$ may be the same as described above.

In an embodiment of the inventive concept, an organic electroluminescence device includes a first electrode, a hole transport region provided on the first electrode, an emission layer provided on the hole transport region, an electron transport region provided on the emission layer, and a second electrode provided on the electron transport region, wherein at least one of the hole transport region and the emission layer includes the polycyclic compound according to an embodiment of the inventive concept.

BRIEF DESCRIPTION OF THE DRAWINGS

The accompanying drawings are included to provide a further understanding of the inventive concept, and are incorporated in and constitute a part of this specification. The drawings illustrate example embodiments of the inventive concept and, together with the description, serve to explain principles of the inventive concept. In the drawings.

DETAILED DESCRIPTION

Figure 1:
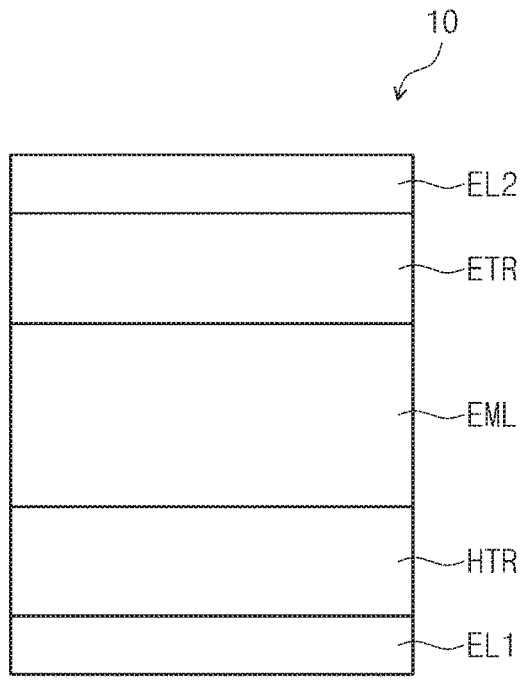
FIG. 1 is a cross-sectional view schematically illustrating an organic electroluminescence device according to an embodiment of the inventive concept.

Objects, features and advantages of the inventive concept will be understood from description of the example embodiments with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art.

Like reference numerals refer to like elements throughout the attached drawings and the written description. In the drawings, the sizes of elements may be enlarged for clarity. It will be understood that, although the terms "first," "second," etc. may be used herein to describe various elements, these elements should not be limited by these terms. These terms are only used to distinguish one element from another element. For example, a first element could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be directly on the other part, or intervening layers may also be present. When a layer, a film, a region, a plate, etc. is referred to as being "under" another part, it can be directly under the other part, or intervening layers may also be present.

As used herein, the term "and/or" includes any and all combinations of one or more of the associated listed items. Expressions such as "one of" and "selected from," when preceding a list of elements, modify the entire list of elements and do not modify the individual elements of the list. Further, the use of "may" when describing embodiments of the present invention refers to "one or more embodiments of the present invention."

In the present disclosure,

may refer to a position in which a connection with a substituent can be made.

In the present disclosure, "substituted or unsubstituted" may refer to an unsubstituted group or a group substituted with at least one substituent selected from deuterium, halogen, nitrile group, nitro group, amino group, silyl group, boron group, phosphine oxide group, alkyl group, alkenyl group, aryl group, and heteroaryl group. In addition, each of the substituents illustrated above may be substituted or unsubstituted. For example, biphenyl group may be referred to as an aryl group, or a phenyl group substituted with a phenyl group.

In the present disclosure, the term "forming a ring via the combination of adjacent groups" may refer to forming substituted or unsubstituted cyclic hydrocarbon group, or substituted or unsubstituted heterocyclic group via the combination of adjacent groups. The cyclic hydrocarbon group may include aliphatic cyclic hydrocarbon and aromatic cyclic hydrocarbon. The heterocyclic group may include aliphatic heterocyclic group and aromatic heterocyclic group. The cyclic hydrocarbon group and heterocyclic group may be a monocyclic group or a polycyclic group. In addition, the ring formed via the combination of adjacent groups may be connected with another ring to form a spiro structure.

In the present disclosure, the term "adjacent groups" may refer to a pair of substituent groups where the first substituent is connected to an atom that is directly connected to another atom substituted with the second substituent, a pair of substituent groups connected to the same atom and different from each other, or a pair of substituent groups where the first substituent is disposed stereoscopically at the nearest position to the second substituent. For example, two methyl groups in 1,2-dimethylbenzene may be interpreted as "adjacent groups", and two ethyl groups in 1,1-diethylcyclopentene may be interpreted as "adjacent groups".

In the present disclosure, "atoms for forming a ring" may refer to ring-forming atoms.

In the present disclosure, "direct linkage" may refer to a bond such a single bond.

In the present disclosure, "halogen" may include fluorine atom, chlorine atom, bromine atom, and/or iodine atom.

In the present disclosure, the alkyl group may have a linear or branched chain or a cyclic shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group may refer to an aromatic cyclic hydrocarbon functional group or substituent. The aryl group may be monocyclic aromatic hydrocarbon group or polycyclic aromatic hydrocarbon group. The number of carbon atoms for forming a ring in the aryl group may be 6 to 30, or 6 to 20. Examples of the aryl group may include phenyl group, naphthyl group, fluorenyl group, anthracenyl group, phenanthryl group, biphenyl group, terphenyl group, quaterphenyl group, quinqphenyl group, sexiphenyl group, triphenylenyl group, pyrenyl group, benzofluoranthenyl group, chrysenyl group, etc., without limitation.

In the present disclosure, the fluorenyl may be substituted, and two substituents may optionally be combined to form a spiro structure.

In the present disclosure, the heteroaryl group may be a cyclic aromatic group including at least one of O, N, P and S as a ring-forming atom, and carbon atoms as the remaining ring-forming atoms. The number of carbon atoms for forming a ring in the heteroaryl group may be 2 to 30, or 2 to 20. Examples of the heteroaryl group may include thiophene, furan, pyrrole, imidazole, thiazole, oxazole, oxadiazole, triazole, pyridyl, bipyridyl, pyrimidyl, triazine, acridyl group, dihydroacridyl group, pyridazinyl group, pyrazinyl group, quinolinyl group, quinazolinyl group, quinoxalinyl group, phenoxazyl group, phthalazinyl group, pyrido pyrimidinyl group, pyrido pyrazinyl group, pyrido indolyl group, pyrazino pyrazinyl group, isoquinolinyl group, indolyl group, carbazolyl group, N-aryl groupcarbazolyl group, N-heteroaryl group carbazolyl group, N-alkyl group carbazolyl group, benzoquinolinyl group, benzoxazolyl group, benzoimidazolyl group, benzothiazolyl group, benzocarbazolyl group, benzothiophenyl group, dibenzothiophenyl group, thienothiophenyl group, benzofuranyl group, phenanthrolinyl group, thiazolyl group, isooxazolyl group, oxadiazolyl group, thiadiazolyl group, benzothiazolyl group, phenothiazinyl group, dibenzofuranyl group, etc., without limitation.

In the present disclosure, the arylene group may refer to a divalent group having substantially the same structure as the aryl group.

In the present disclosure, the heteroarylene group may refer to a divalent group having substantially the same structure as the heteroaryl group.

In the present disclosure, the silyl group may include alkylsilylsilyl group and arylsilyl group. Examples of the silyl group may include trimethylsilyl group, triethylsilyl group, t-butyl dimethylsilyl group, vinyl dimethylsilyl group, propyl dimethylsilyl group, triphenylsilyl group, diphenylsilyl group, phenylsilyl group, etc., without limitation.

In the present disclosure, the boron group may include alkyl boron group and aryl boron group. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched hydrocarbon group having at least one carbon-carbon double bond at one or more positions along the hydrocarbon chain. The carbon number is not specifically limited, however may be 2 to 30, 2 to 20, or 2 to 10. Examples of the alkenyl group may include vinyl group, 1-butenyl group, 1-pentenyl group, 1,3-butadienyl aryl group, styrenyl group, styrylvinyl group, etc., without limitation.

In the present disclosure, the carbon number of the amine group is not specifically limited, however may be 1 to 30. The amine group may include an alkylamine group and arylamine group. Examples of the amine group may include methylamine, dimethylamine, phenylamine, naphthylamine, 9-methyl-anthracenylamine, triphenylamine, etc., without limitation.

Hereinafter, the polycyclic compound according to an embodiment of the inventive concept will be explained in more detail.

The polycyclic compound according to an embodiment of the inventive concept may be represented by the following Formula 1:

Formula 1

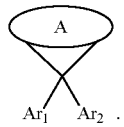

In Formula 1, $Ar_1$ and $Ar_2$ may each independently be substituted or unsubstituted aryl group having 6 to 30 carbon atoms for forming a ring, or substituted or unsubstituted heteroaryl group having 2 to 30 carbon atoms for forming a ring, where $Ar_1$ and $Ar_2$ may combine with each other to form a ring.

In Formula 1, A may be a substituted or unsubstituted group having at least 14 carbon atoms. For example, A may be represented by the following Formula 2-1 or 2-2:

Formula 2-1

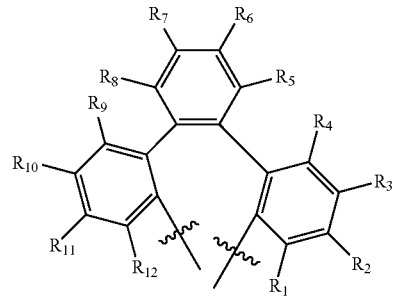

Formula 2-2

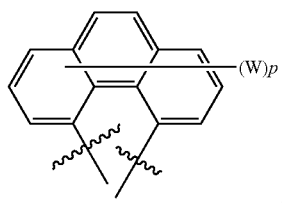

In Formula 2-1, $R_1$ to $R_{12}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, where adjacent groups may combine with each other to form a ring, and in Formula 2-2, W may be selected from hydrogen, deuterium, halogen, silyl group, substituted or unsubstituted alkyl group having 1 to 20 carbon atoms, substituted or unsubstituted aryl group having 6 to 60 carbon atoms for forming a ring, and substituted or unsubstituted heteroaryl group having 5 to 60 carbon atoms for forming a ring; and p may be an integer from 0 to 8. In the case where p is 2 or more, a plurality of W may be the same as or different from each other.

In Formula 1, A may be represented by Formula 2-2. In Formula 1, A may be represented by Formula 2-2, and $Ar_1$ and $Ar_2$ may combine with each other to form a heterocyclic group. For example, Formula 1 may be represented by the following Formula 3:

Formula 3

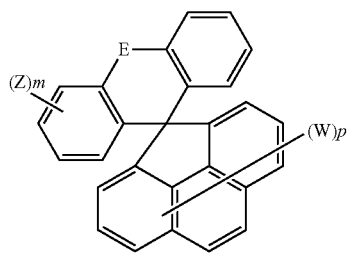

In Formula 3, W and p are the same as described above; E may be O, S, or NR'; m may be 0 or 1; and Z and R' may each independently be represented by the following Formula 4:

Formula 4

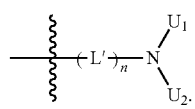

In Formula 4, $U_1$ and $U_2$ may each independently be substituted or unsubstituted aryl group having 6 to 30 carbon atoms for forming a ring, or substituted or unsubstituted heteroaryl group having 2 to 30 carbon atoms for forming a ring; L' may be substituted or unsubstituted arylene group having 6 to 30 carbon atoms for forming a ring; and n may be 0 or 1. In the case where E is NR', m may be 0, and in the case where E is O or S, m may be 1.

The polycyclic compound represented by Formula 3 may be an amine compound including nitrogen.

In Formula 2-2, p may be 0.

In Formula 4, $U_1$ and $U_2$ may be each independently selected from substituted or unsubstituted phenyl group, substituted or unsubstituted naphthyl group, substituted or unsubstituted biphenyl group, and substituted or unsubstituted terphenyl group.

In Formula 4, $U_1$ and $U_2$ may be each independently selected from unsubstituted phenyl group or phenyl group substituted with naphthyl group, substituted or unsubstituted naphthyl group, substituted or unsubstituted biphenyl group, and substituted or unsubstituted terphenyl group.

L' may be m-phenylene or p-phenylene.

In the case where E is O or S, n may be 0 or 1. In the case where E is NR', n may be 0 or 1.

Formula 3 may be represented by the following Formula 5:

Formula 5

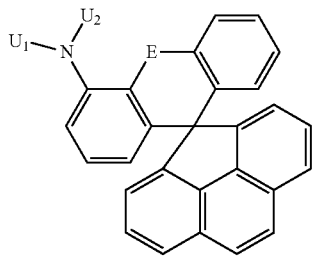

In Formula 5, E, $U_1$ and $U_2$ are the same as described above.

The polycyclic compound represented by Formula 1 may be selected from the compounds A-1 to A-23 (collectively denoted as Formula Group 1). However, an example embodiment is not limited thereto.

Formula Group 1

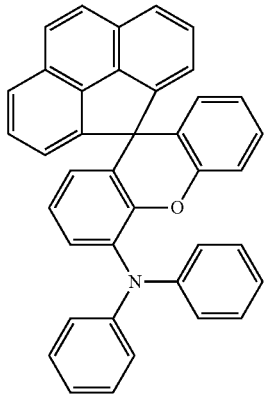

A-1

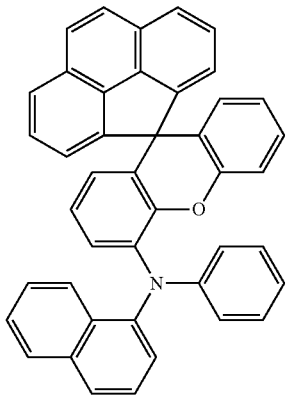

A-2

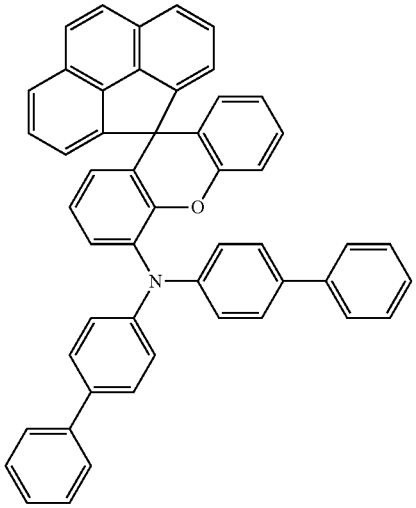

A-3

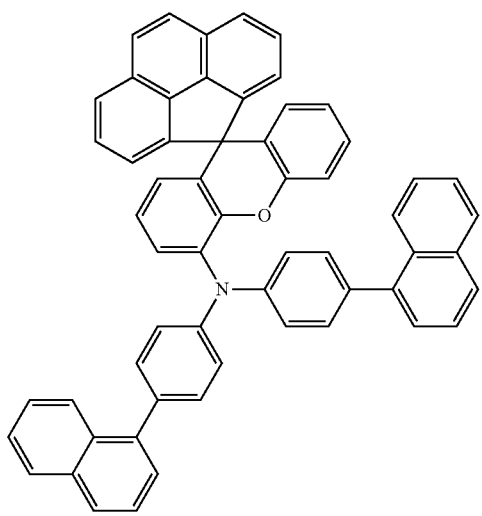
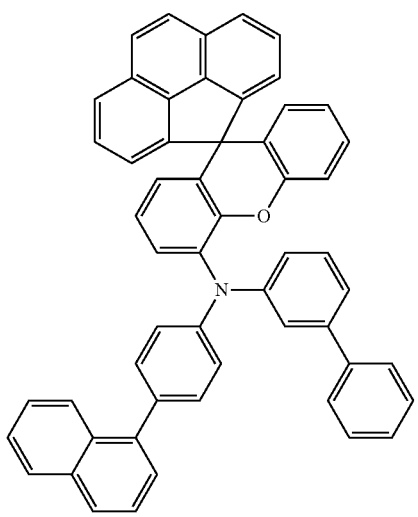

A-10
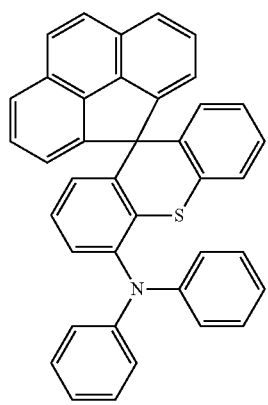
A-11
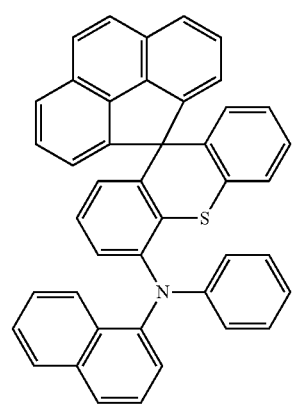
A-12
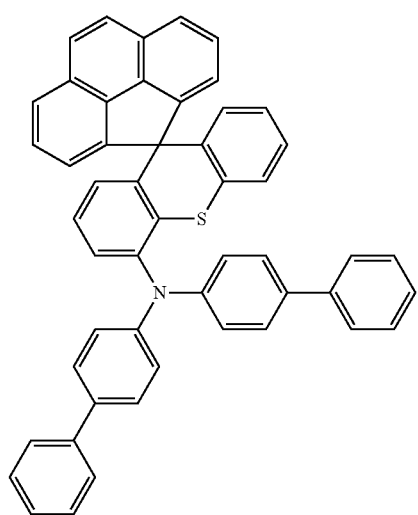
A-13
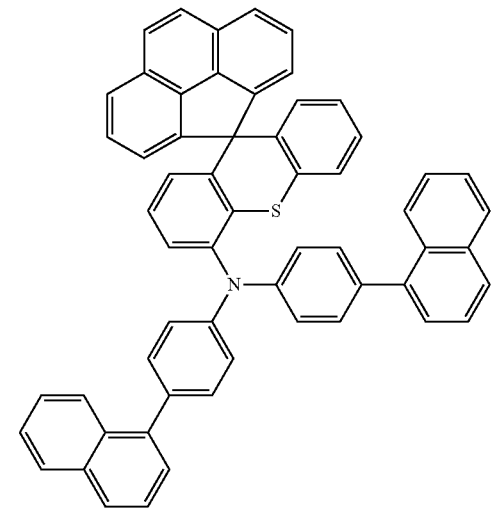
A-14
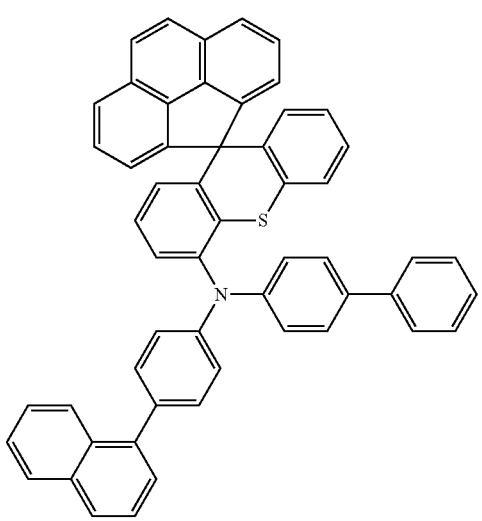
A-15
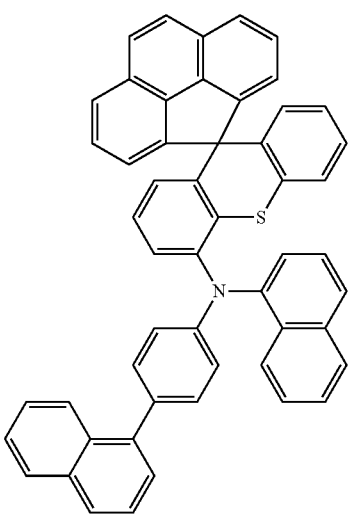

A-16
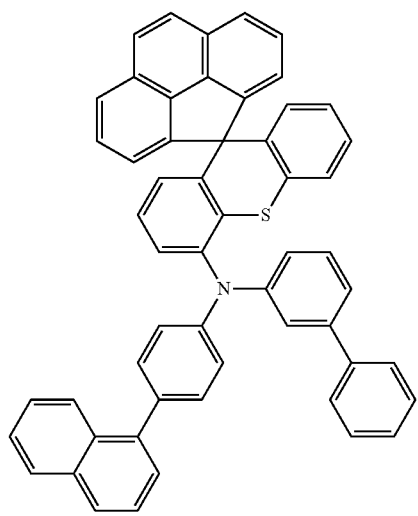
A-17
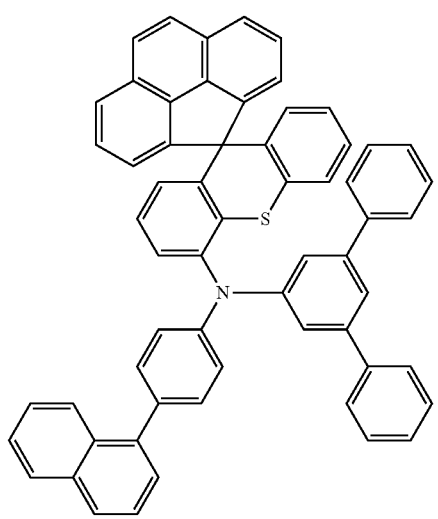
A-18
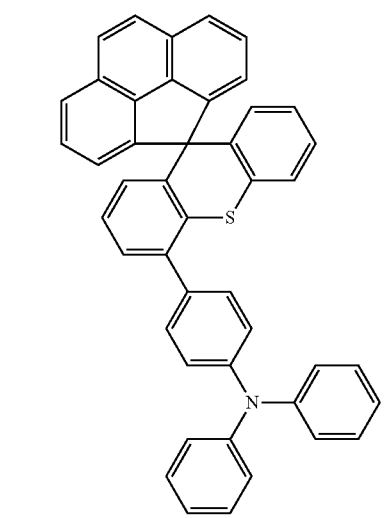
A-19
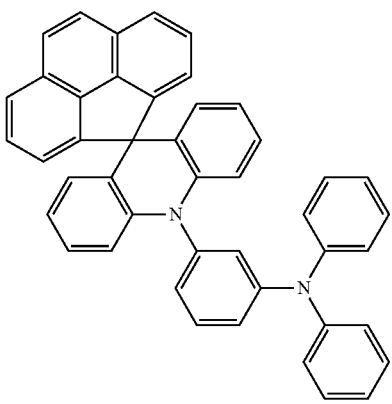
A-20
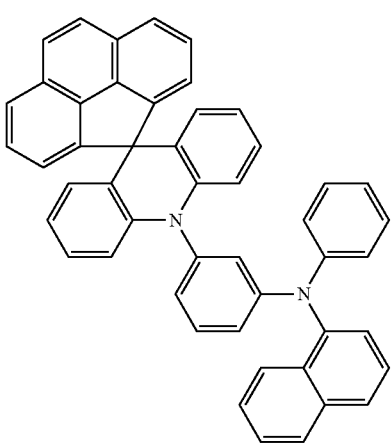
A-21
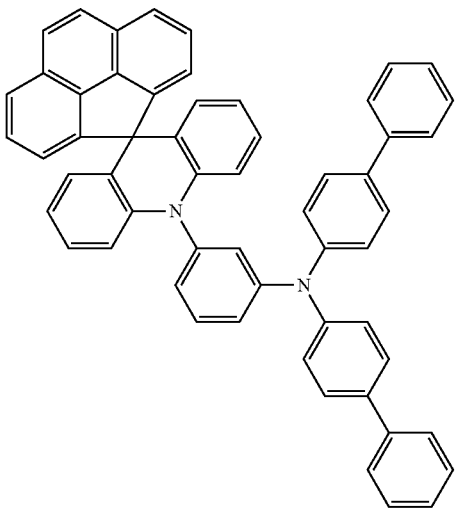
A-22
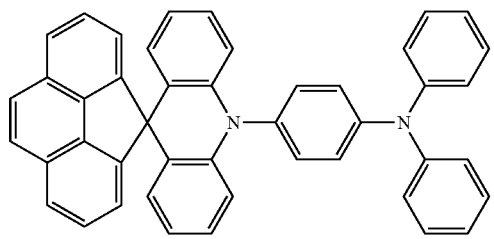

-continued

A-23

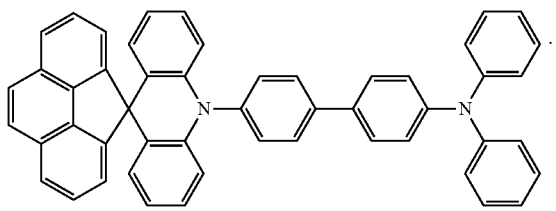

In Formula 1, A may be represented by Formula 2-1. In this case, Formula 1 may be represented by the following Formula 1-1:

Formula 1-1

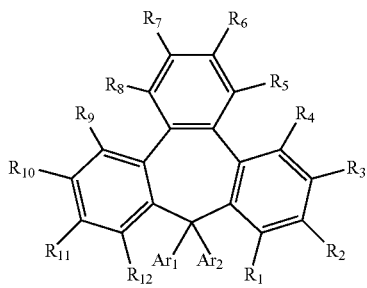

In Formula 1, A may be represented by Formula 2-1 and $Ar_1$ and $Ar_2$ may be each independently substituted or unsubstituted aryl group having 6 to 20 carbon atoms for forming a ring, or substituted or unsubstituted heteroaryl group having 3 to 10 carbon atoms for forming a ring, and $Ar_1$ and $Ar_2$ may be combined with each other to form a ring.

In Formula 1, A may be represented by Formula 2-1, and $Ar_1$ and $Ar_2$ may be each independently substituted or unsubstituted phenyl group, substituted or unsubstituted anthracenyl group, substituted or unsubstituted pyrenyl group, substituted or unsubstituted phenanthryl group, substituted or unsubstituted chrysenyl group, substituted or unsubstituted triphenylenyl group, substituted or unsubstituted carbazolyl group, or substituted or unsubstituted pyridyl group, where $Ar_1$ and $Ar_2$ may combine with each other to form a ring.

In Formula 1, A may be represented by Formula 2-1, and at least one of $Ar_1$ and $Ar_2$ may be substituted or unsubstituted phenyl group. $Ar_1$ and $Ar_2$ may be each independently substituted or unsubstituted phenyl group. $Ar_1$ and $Ar_2$ may combine with each other to form fluorenyl group. One of $Ar_1$ and $Ar_2$ may be substituted or unsubstituted phenyl group, and the remaining one may be substituted or unsubstituted aryl group having a three- or four-membered ring.

In Formula 1, A may be represented by Formula 2-1 and $Ar_1$ and $Ar_2$ may be each independently substituted or unsubstituted pyridyl group. In Formula 1, A may be represented by Formula 2-1, and $Ar_1$ and $Ar_2$ may be each independently substituted or unsubstituted carbazolyl group. In Formula 1, A may be represented by Formula 2-1, and $Ar_1$ and $Ar_2$ may be each independently carbazole substituted with phenyl group. In Formula 1, A may be represented by Formula 2-1, and $Ar_1$ and $Ar_2$ may be each independently N-phenylcarbazole.

The polycyclic compound of Formula 1 may be represented by the following Formula 6:

Formula 6

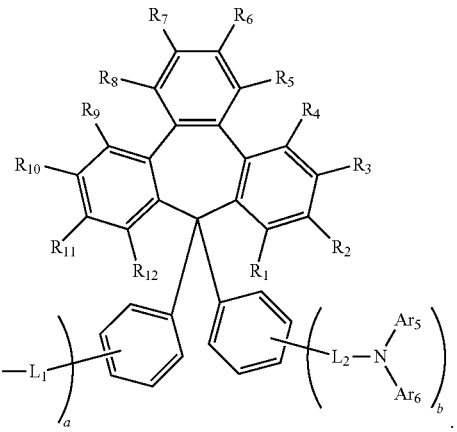

In Formula 6, $L_1$ and $L_2$ may each independently be selected from a direct linkage, substituted or unsubstituted arylene group having 6 to 30 carbon atoms for forming a ring, and substituted or unsubstituted heteroarylene group having 2 to 30 carbon atoms for forming a ring; $Ar_3$ to $Ar_6$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; a and b may each independently be 0 or 1, where the sum of a and b is not 0 (a+b≠0); and $R_1$ to $R_{12}$ are the same as described above.

In Formula 6, a and b may each independently be 1, and $Ar_3$ to $Ar_6$ may be each independently substituted or unsubstituted aryl group having 6 to 30 carbon atoms for forming a ring. For example, $Ar_1$ and $Ar_2$ in Formula 1 may be each independently phenyl group substituted with arylamine group directly or via a linker (e.g., $L_1$ or $L_2$ in Formula 6).

In Formula 6, $Ar_3$ to $Ar_6$ may be each independently substituted or unsubstituted aryl group having 6 to 20 carbon atoms for forming a ring. $Ar_3$ to $Ar_6$ may be each independently unsubstituted aryl group having 6 to 20 carbon atoms for forming a ring. $Ar_3$ to $Ar_6$ may be each independently substituted or unsubstituted phenyl group, substituted or unsubstituted biphenyl group, or substituted or unsubstituted naphthyl group.

A in Formula 1 may be represented by Formula 2-1, and $Ar_1$ and $Ar_2$ in Formula 1 may be the same. For example, $Ar_3$ to $Ar_6$ in Formula 6 may be the same. Alternatively, $Ar_3$ and $Ar_5$ may be the same, and $Ar_4$ and $Ar_6$ may be the same. In this case, $Ar_3$ and $Ar_4$ may be different from each other, and $Ar_5$ and $Ar_6$ may be different from each other. However, an embodiment is not limited thereto, and $Ar_1$ and $Ar_2$ may be different from each other.

In Formula 6, the sum of a and b may equal to 1 (a+b=1). For example, Formula 6 may be represented by the following Formula 6-1:

Formula 6-1

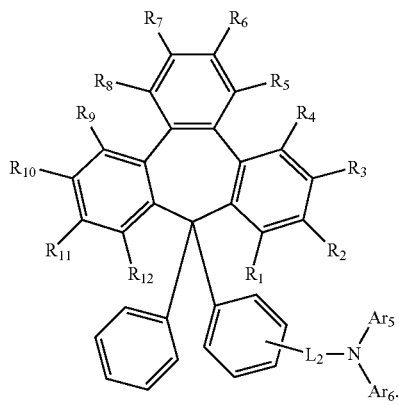

In Formula 6-1, $R_1$ to $R_{12}$, $L_2$, $Ar_5$ and $Ar_6$ are the same as described above.

The polycyclic compound of Formula 1 may be represented by the following Formula 7:

Formula 7

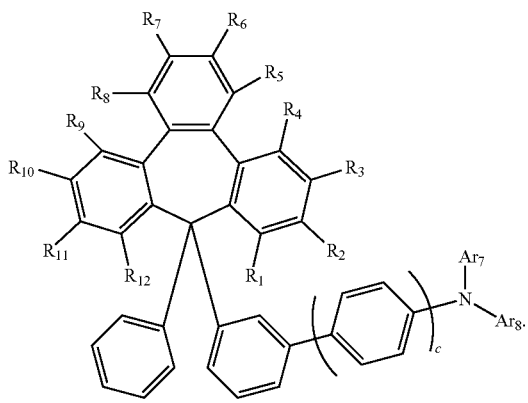

In Formula 7, $Ar_7$ and $Ar_8$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; c may be 0 or 1; and $R_1$ to $R_{12}$ are the same as described above.

In Formula 7, $Ar_7$ and $Ar_8$ may be each independently substituted or unsubstituted aryl group having 6 to 30 carbon atoms for forming a ring. $Ar_7$ and $Ar_8$ may be each independently substituted or unsubstituted aryl group having 6 to 20 carbon atoms for forming a ring. $Ar_7$ and $Ar_8$ may be each independently unsubstituted aryl group having 6 to 20 carbon atoms for forming a ring. For example, $Ar_7$ and $Ar_8$ may be each independently substituted or unsubstituted phenyl group, substituted or unsubstituted biphenyl group, or substituted or unsubstituted naphthyl group. $Ar_7$ and $Ar_8$ may be each independently unsubstituted phenyl group or phenyl group substituted with naphthyl group, substituted or unsubstituted biphenyl group, substituted or unsubstituted naphthyl group.

The polycyclic compound of Formula 1 may be represented by the following Formula 8:

Formula 8

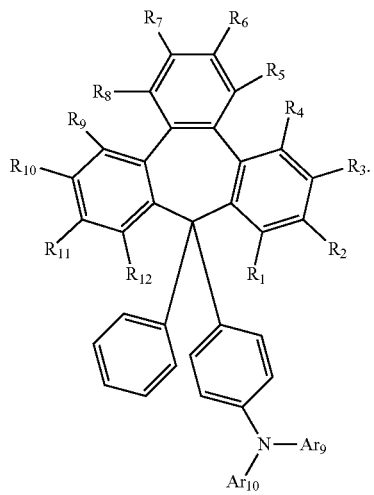

In Formula 8, $Ar_9$ and $Ar_{10}$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; and $R_1$ to $R_{12}$ are the same as described above.

In Formula 8, $Ar_9$ and $Ar_{10}$ may be each independently substituted or unsubstituted aryl group having 6 to 30 carbon atoms for forming a ring. $Ar_9$ and $Ar_{10}$ may be each independently substituted or unsubstituted aryl group having 6 to 20 carbon atoms for forming a ring. $Ar_9$ and $Ar_{10}$ may be each independently unsubstituted aryl group having 6 to 20 carbon atoms for forming a ring. For example, $Ar_9$ and $Ar_{10}$ may be each independently substituted or unsubstituted phenyl group, substituted or unsubstituted biphenyl group, or substituted or unsubstituted naphthyl group. $Ar_9$ and $Ar_{10}$ may be each independently unsubstituted phenyl group or phenyl group substituted with naphthyl group, substituted or unsubstituted biphenyl group, substituted or unsubstituted naphthyl group.

The polycyclic compound of Formula 1 may be represented by the following Formula 9:

Formula 9

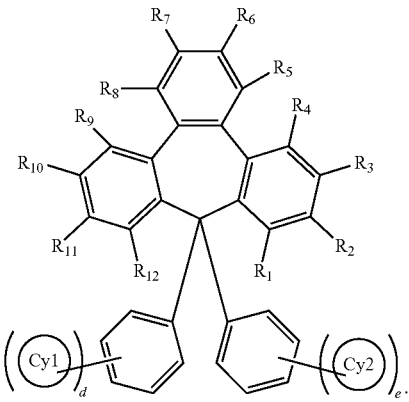

In Formula 9, Cy1 and Cy2 may each independently be substituted or unsubstituted heteroaryl group including 1 to 3 N atoms as heteroatoms and having 2 to 30 carbon atoms for forming a ring; d and e may each independently be 0 or 1, where the sum of d and e is not 0 (d+e≠0); and $R_1$ to $R_{12}$ are the same as described above.

In Formula 9, Cy1 and Cy2 may be each independently substituted or unsubstituted pyridyl group, substituted or unsubstituted pyrimidyl group, substituted or unsubstituted triazinyl group, substituted or unsubstituted carbazolyl group, substituted or unsubstituted pyrido indolyl group, or substituted or unsubstituted isoquinolinyl group.

In Formula 9, Cy1 and Cy2 may be each independently one selected from the following formulae:

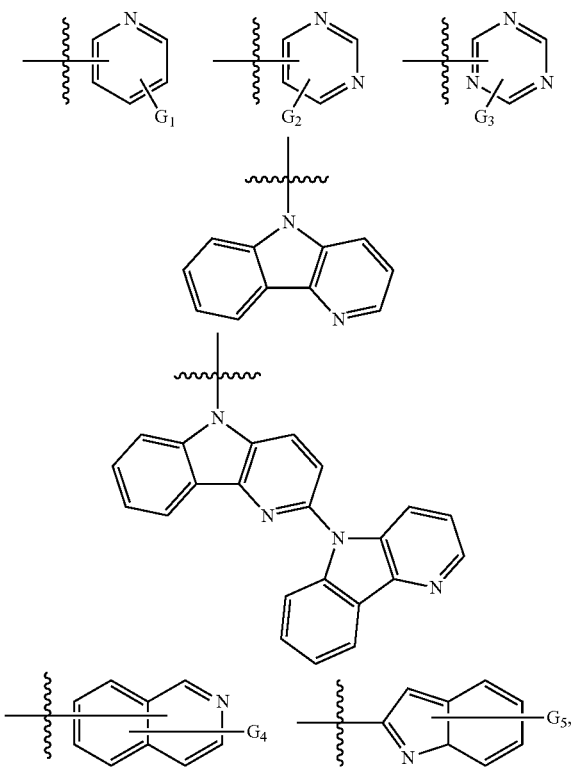

where $G_1$ to $G_5$ may be each independently selected from hydrogen, deuterium, and substituted or unsubstituted aryl group having 6 to 30 carbon atoms for forming a ring. A plurality of each of $G_1$ to $G_5$ may be present. $G_1$ to $G_5$ may be each independently hydrogen or substituted or unsubstituted phenyl group.

In Formula 9, d and e may be each independently 1. However, an embodiment is not limited thereto, and the sum of d and e (d+e) may be 1.

As described above, in Formula 1, $Ar_1$ and $Ar_2$ may combine with each other to form a ring. In Formula 1, A may be represented by Formula 2-1, and $Ar_1$ and $Ar_2$ may combine with each other to form a substituted or unsubstituted aromatic hydrocarbon ring (e.g., aromatic hydrocarbon cyclic group). $Ar_1$ and $Ar_2$ may combine with each other to form substituted or unsubstituted fluorenyl group. For example, the polycyclic compound of Formula 1 may be represented by the following Formula 10:

Formula 10

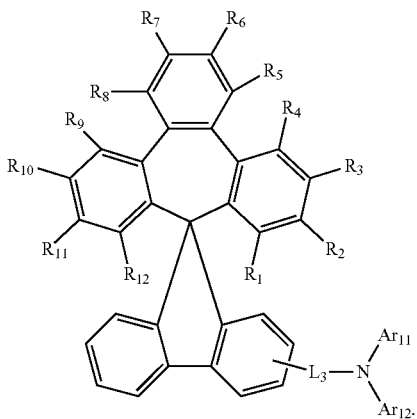

In Formula 10, $Ar_{11}$ and $Ar_{12}$ may each independently be selected from hydrogen, deuterium, substituted or unsubstituted aryl group having 6 to 30 carbon atoms for forming a ring, and substituted or unsubstituted heteroaryl group having 2 to 30 carbon atoms for forming a ring; $L_3$ may be a direct linkage, substituted or unsubstituted arylene group having 6 to 30 carbon atoms for forming a ring, or substituted or unsubstituted heteroarylene group having 2 to 30 carbon atoms for forming a ring; and $R_1$ to $R_{12}$ are the same as described above.

In Formula 10, $Ar_{11}$ and $Ar_{12}$ may be each independently substituted or unsubstituted aryl group having 6 to 30 carbon atoms for forming a ring. $Ar_{11}$ and $Ar_{12}$ may be each independently substituted or unsubstituted aryl group having 6 to 20 carbon atoms for forming a ring. $Ar_{11}$ and $Ar_{12}$ may be each independently unsubstituted aryl group having 6 to 20 carbon atoms for forming a ring. For example, $Ar_{11}$ and $Ar_{12}$ may be each independently substituted or unsubstituted phenyl group, substituted or unsubstituted biphenyl group, or substituted or unsubstituted naphthyl group. $Ar_{11}$ and $Ar_{12}$ may be each independently unsubstituted phenyl group or phenyl group substituted with naphthyl group, substituted or unsubstituted biphenyl group, substituted or unsubstituted naphthyl group.

In Formula 10, $L_3$ may be a direct linkage, or substituted or unsubstituted arylene group having 6 to 30 carbon atoms for forming a ring. $L_3$ may be a direct linkage, or substituted or unsubstituted arylene group having 6 to 20 carbon atoms for forming a ring. $L_3$ may be a direct linkage, or substituted or unsubstituted phenylene group. $L_3$ may be a direct linkage, or substituted or unsubstituted 1,4-phenylene group.

The polycyclic compound of Formula 1 may be represented by the following Formula 11:

Formula 11

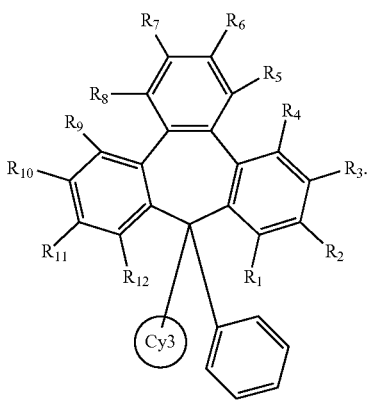

In Formula 11, Cy3 may be substituted or unsubstituted aryl group having a three- or four-membered ring; and $R_1$ to $R_{12}$ are the same as described above.

For example, Cy3 may be selected from substituted or unsubstituted anthracenyl group, substituted or unsubstituted pyrenyl group, substituted or unsubstituted phenanthryl group, substituted or unsubstituted chrysenyl group, and substituted or unsubstituted triphenylenyl group. Cy3 may be anthracenyl group substituted with at least one substituent selected from phenyl group, naphthyl group and arylamine group. Cy3 may be pyrenyl group substituted with at least one substituent selected from phenyl group, nitrile group and arylamine group. Cy3 may be phenanthryl group substituted with at least one substituent selected from naphthyl group and nitrile group. Cy3 may be chrysenyl group substituted with at least one substituent selected from phenyl group and arylamine group. Cy3 may be triphenylenyl group substituted with at least one nitrile or unsubstituted triphenylenyl group.

In Formula 2-1, $R_1$ to $R_{12}$ may be each independently hydrogen. However, an embodiment is not limited thereto, and at least one of $R_1$ to $R_{12}$ may be a substituent other than hydrogen.

As described above, in Formula 2-1, adjacent groups selected from $R_1$ to $R_{12}$ may combine to form a ring. For example, Formula 1 may be represented by the following Formula 12:

Formula 12

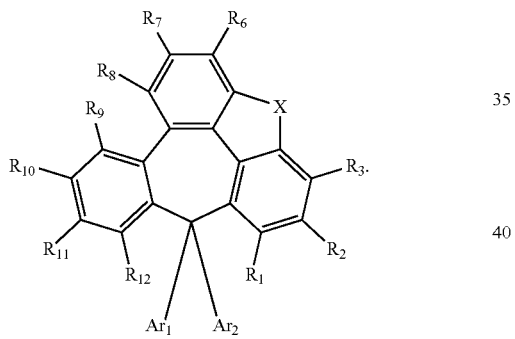

In Formula 12, X may be O, S, $NR_{13}$, $CR_{14}R_{15}$, or $SiR_{16}R_{17}$; $R_{13}$ to $R_{17}$ may each independently be selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; and $Ar_1$, $Ar_2$, $R_1$ to $R_3$, and $R_6$ to $R_{12}$ are the same as described above.

X may be O or S. X may be O. X may be S.

X may be $CR_{14}R_{15}$, or $SiR_{16}R_{17}$, and $R_{14}$ to $R_{17}$ may be each independently substituted or unsubstituted alkyl group having 1 to 20 carbon atoms. X may be $CR_{14}R_{15}$, or $SiR_{16}R_{17}$, and $R_{14}$ to $R_{17}$ may be each independently substituted or unsubstituted alkyl group having 1 to 10 carbon atoms. X may be $CR_{14}R_{15}$, or $SiR_{16}R_{17}$, and $R_{14}$ to $R_{17}$ may be each independently methyl group or ethyl group. X may be $CR_{14}R_{15}$, or $SiR_{16}R_{17}$, and $R_{14}$ to $R_{17}$ may be methyl group.

X may be $NR_{13}$. X may be $NR_{13}$ and $R_{13}$ may be hydrogen or substituted or unsubstituted aryl group having 6 to 30 carbon atoms. X may be $NR_{13}$ and $R_{13}$ may be hydrogen or substituted or unsubstituted aryl group having 6 to 20 carbon atoms. X may be $NR_{13}$ and $R_{13}$ may be hydrogen or substituted or unsubstituted phenyl group. X may be $NR_{13}$ and $R_{13}$ may be hydrogen or unsubstituted phenyl group.

In Formula 12, $R_1$ to $R_3$ and $R_6$ to $R_{12}$ may be each independently hydrogen or a nitrogen-containing substituent group. For example, in Formula 12, $R_1$ to $R_3$ and $R_6$ to $R_{12}$ may be each independently hydrogen or may be represented by one of the following structures:

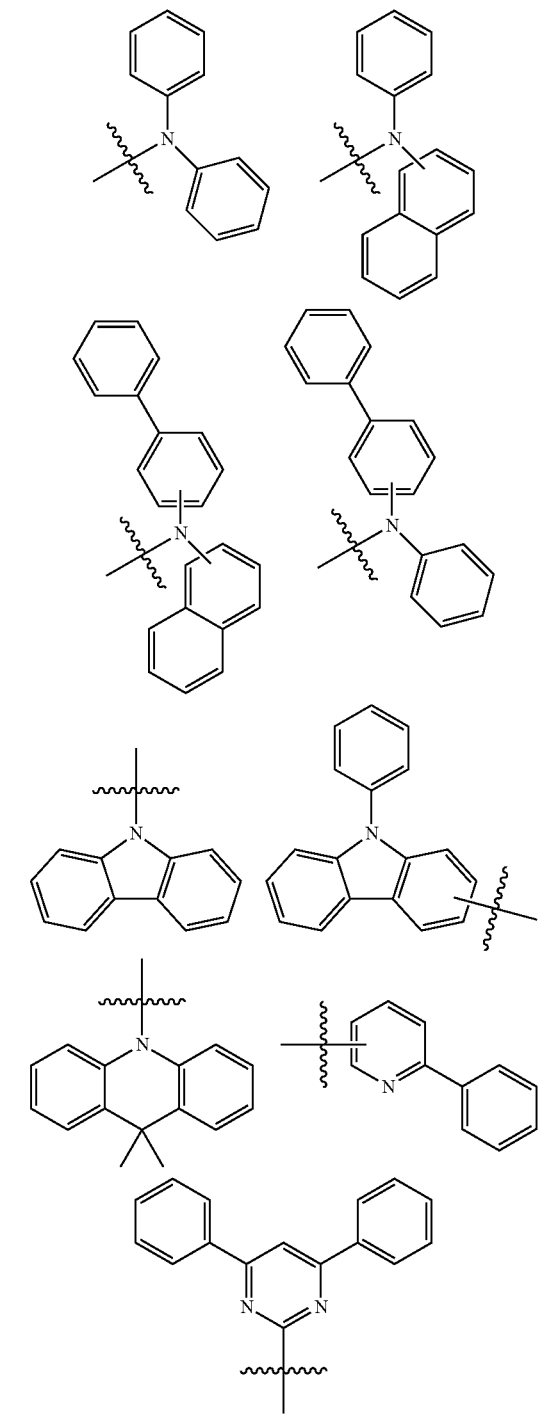

Formula 13

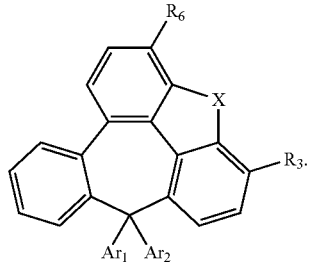

In Formula 13, $R_3$ and $R_6$ may each independently be selected from substituted or unsubstituted arylamine group, substituted or unsubstituted aryl group having 6 to 30 carbon atoms for forming a ring, and substituted or unsubstituted heteroaryl group having 2 to 30 carbon atoms for forming a ring; and X, $Ar_1$ and $Ar_2$ are the same as defined in Formula 12.

However, an embodiment is not limited thereto, and for example, at least three of $R_1$ to $R_3$ and $R_6$ to $R_{12}$ may be selected from substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, or adjacent groups selected from $R_1$ to $R_3$ and $R_6$ to $R_{12}$ may be combined to form a ring, and the rest of $R_1$ to $R_3$ and $R_6$ to $R_{12}$ may be hydrogen.

In some embodiments, any of $R_1$ to $R_{12}$ may partially combine with an adjacent group selected from $R_1$ to $R_{12}$ to form substituted or unsubstituted carbazole. Any of $R_1$ to $R_{12}$ may partially combine with an adjacent group selected from $R_1$ to $R_{12}$ to form N-aryl carbazole. Any of $R_1$ to $R_{12}$ may partially combine with an adjacent group selected from $R_1$ to $R_{12}$ to form N-phenyl carbazole. For example, Formula 12 may be represented by the following Formula 14:

Formula 14

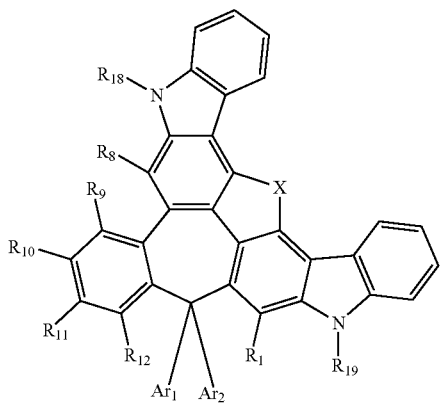

In Formula 14, $R_{18}$ and $R_{19}$ may be each independently selected from hydrogen, deuterium, substituted or unsubstituted aryl group having 6 to 30 carbon atoms for forming a ring, and substituted or unsubstituted heteroaryl group having 2 to 30 carbon atoms for forming a ring; and X, $Ar_1$, $Ar_2$, $R_1$, and $R_8$ to $R_{12}$ are the same as defined in Formula 8.

In Formula 14, $R_{18}$ and $R_{19}$ may be each independently substituted or unsubstituted aryl group having 6 to 30 carbon atoms for forming a ring. In Formula 10, $R_{18}$ and $R_{19}$ may be each independently N-aryl carbazole. $R_{16}$ and $R_{17}$ may be each independently N-phenyl carbazole.

In Formula 14, $R_1$ and $R_8$ to $R_{12}$ may be hydrogen.

Formula 12 may be represented by the following Formula 15:

-continued

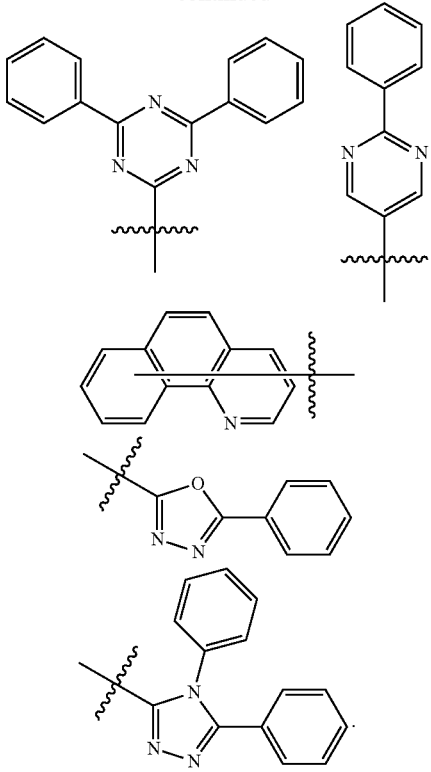

However, an embodiment is not limited thereto. For example, in Formula 12, $R_1$ to $R_3$ and $R_6$ to $R_{12}$ may be each independently hydrogen or may be represented by one of the following structures:

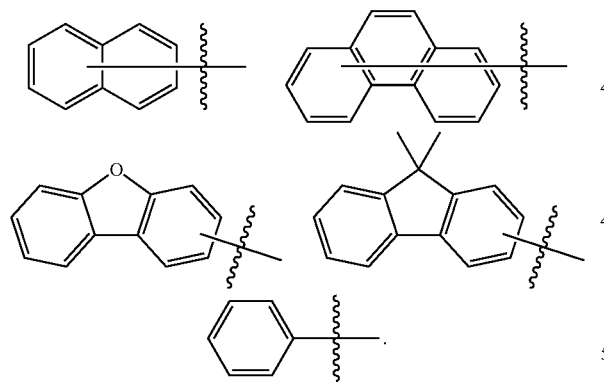

In Formula 12, at least two of $R_1$ to $R_3$ and $R_6$ to $R_{12}$ may be substituted or unsubstituted arylamine group, substituted or unsubstituted aryl group having 6 to 30 carbon atoms for forming a ring, or substituted or unsubstituted heteroaryl group having 2 to 30 carbon atoms for forming a ring, or adjacent groups selected from $R_1$ to $R_3$ and $R_6$ to $R_{12}$ may be combined to form a ring.

At least two of $R_1$ to $R_3$ and $R_6$ to $R_{12}$ may be substituted or unsubstituted arylamine group, substituted or unsubstituted aryl group having 6 to 30 carbon atoms for forming a ring, or substituted or unsubstituted heteroaryl group having 2 to 30 carbon atoms for forming a ring, or adjacent groups selected from $R_1$ to $R_3$ and $R_6$ to $R_{12}$ may be combined to form a ring, and the rest of $R_1$ to $R_3$ and $R_6$ to $R_{12}$ may be hydrogen. For example, Formula 12 may be represented by the following Formula 13:

Formula 15

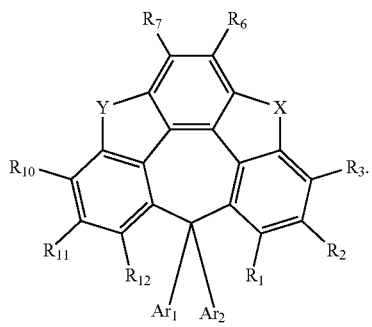

In Formula 15, Y may be O, S, $NR_{20}$, or substituted or unsubstituted phosphine oxide; $R_{20}$ may be hydrogen, deuterium, substituted or unsubstituted aryl group having 6 to 30 carbon atoms for forming a ring, or substituted or unsubstituted heteroaryl group having 2 to 30 carbon atoms for forming a ring; and X, $Ar_1$, $Ar_e$, $R_1$ to $R_3$, $R_6$, $R_7$, and $R_{10}$ to $R_{12}$ are the same as defined in Formula 12.

In Formula 15, Y may be phosphine oxide substituted with phenyl group. In Formula 15, Y may be $NR_{20}$, and $R_{20}$ may be phenyl group.

Formula 12 may be represented by the following Formula 16:

Formula 16

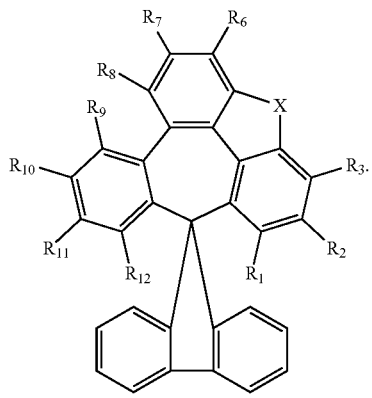

In Formula 16, X, $R_1$ to $R_3$ and $R_6$ to $R_{12}$ are the same as defined in Formula 12.

In Formula 16, $R_3$ and $R_6$ may be each independently substituted or unsubstituted arylamine group, substituted or unsubstituted aryl group having 6 to 30 carbon atoms for forming a ring, or substituted or unsubstituted heteroaryl group having 2 to 30 carbon atoms for forming a ring.

In Formula 16, $R_3$ and $R_6$ may be each independently substituted or unsubstituted arylamine group.

In Formula 16, $R_6$ and $R_7$ may combine with each other to form substituted or unsubstituted carbazole. In Formula 16, $R_6$ and $R_7$ may combine with each other to form N-aryl carbazole. In Formula 16, $R_6$ and $R_7$ may combine with each other to form N-phenyl carbazole.

In Formula 16, $R_2$ and $R_3$ may combine with each other to form substituted or unsubstituted carbazole. In Formula 16, $R_2$ and $R_3$ may combine with each other to form N-aryl carbazole. In Formula 16, $R_2$ and $R_3$ may combine with each other to form N-phenyl carbazole.

The polycyclic compound represented by Formula 1 may be one selected from Compounds 1 to 66 (collectively denoted as Compound Group 2). However, an embodiment is not limited thereto.

Formula Group 2

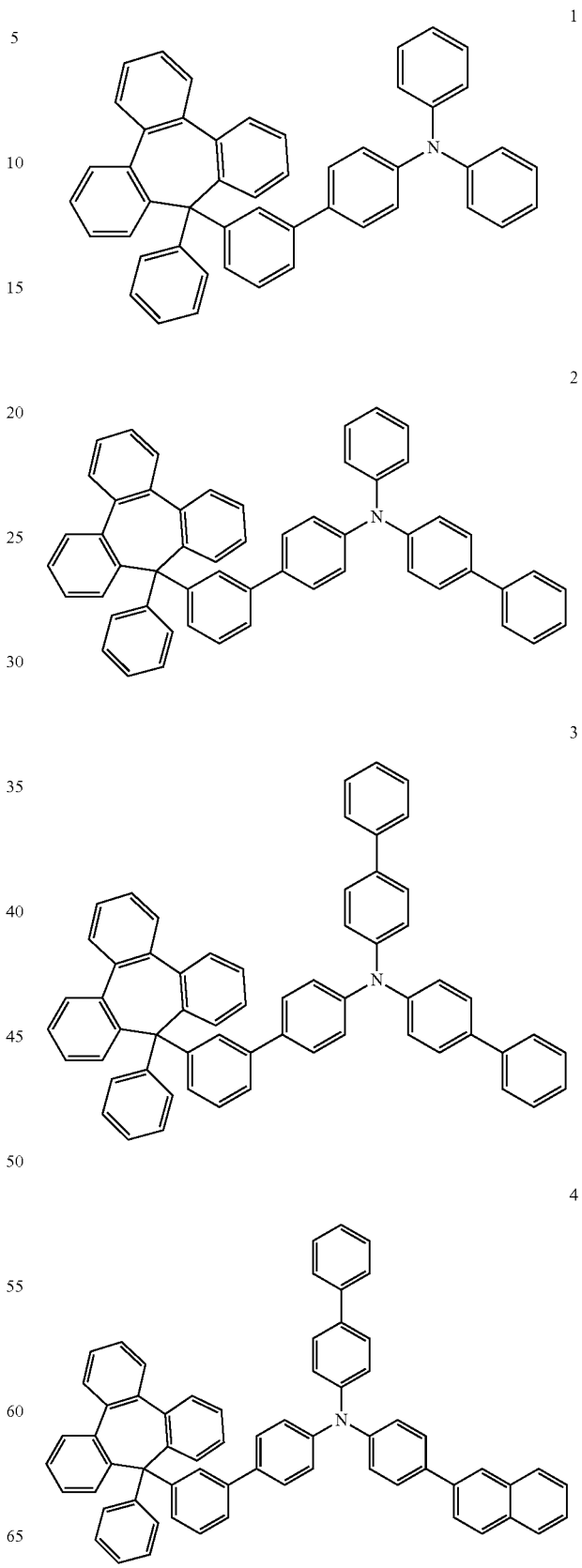

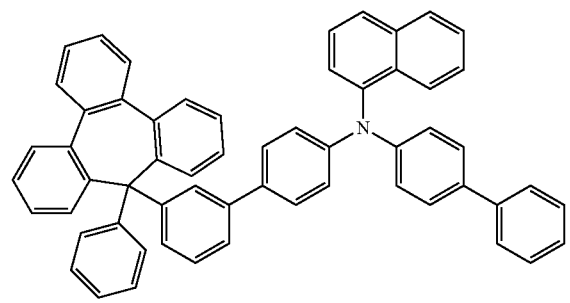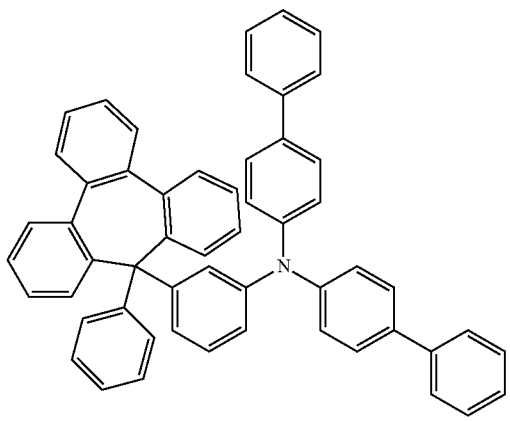

13
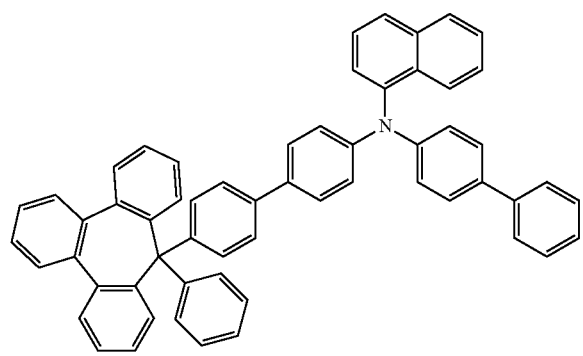
14
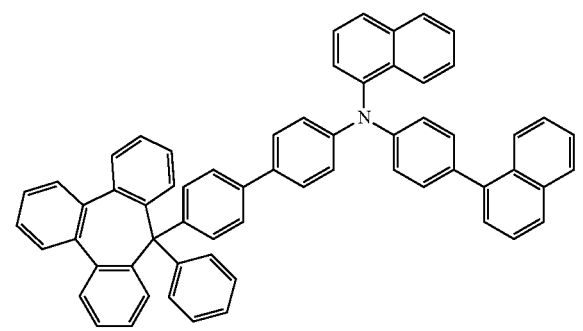
15
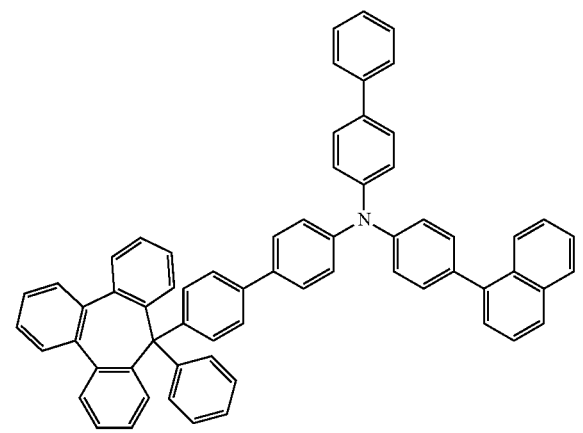
16
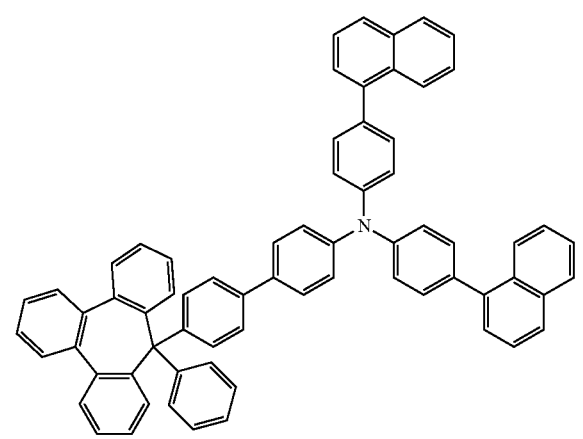
17
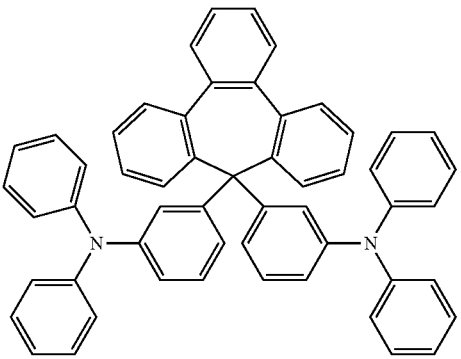
18
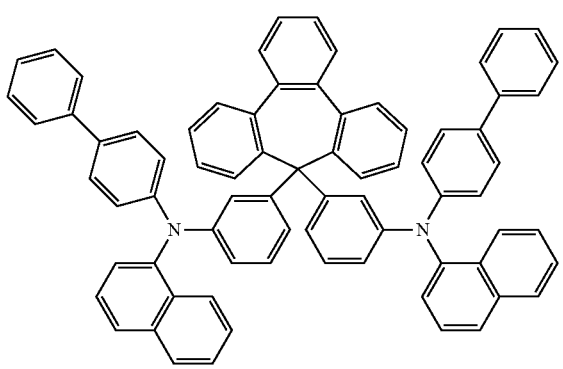
19
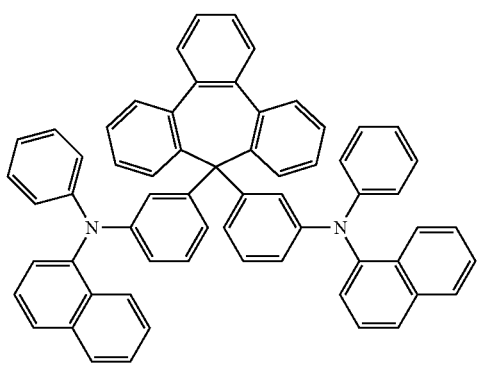
20
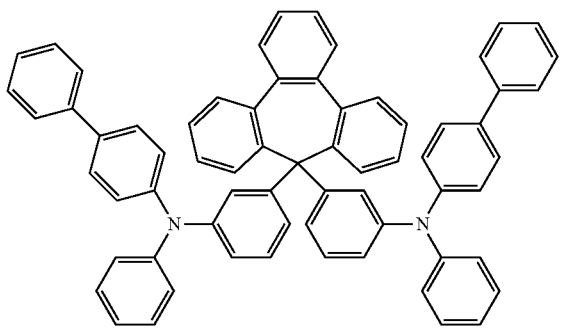

21
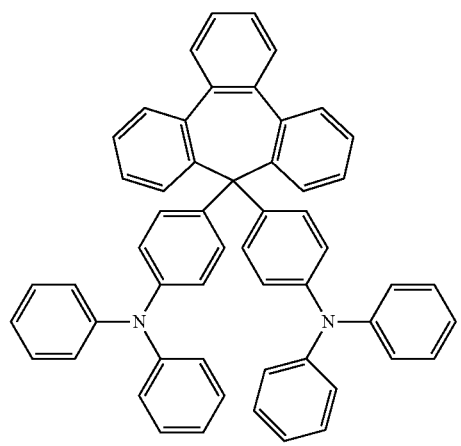
22
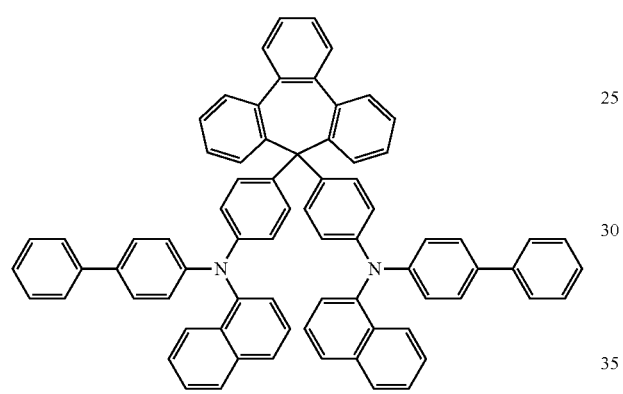
23
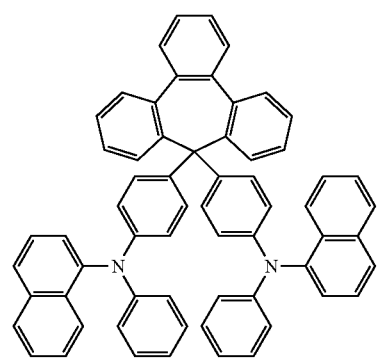
24
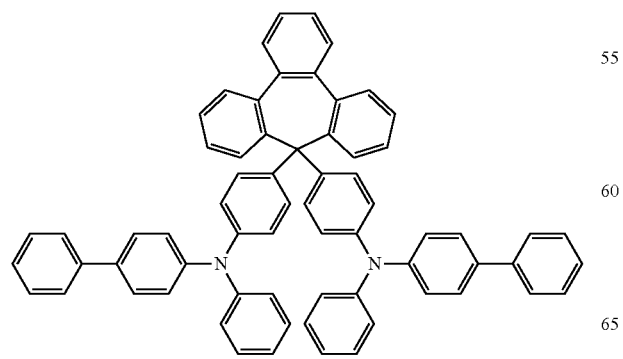
25
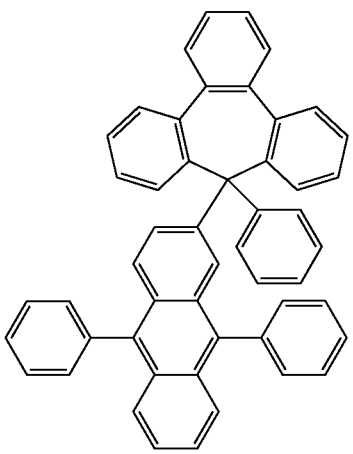
26
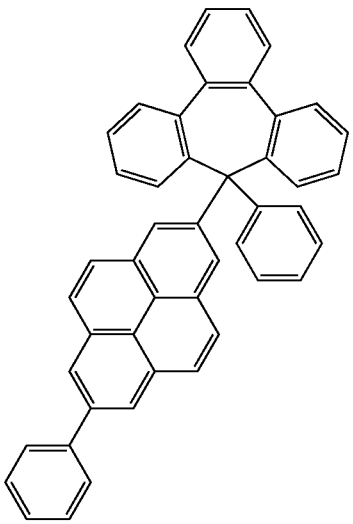
27
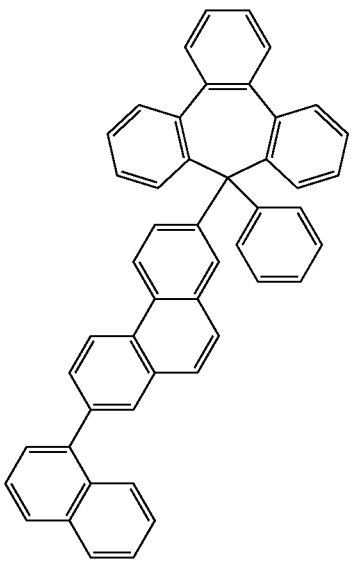

28
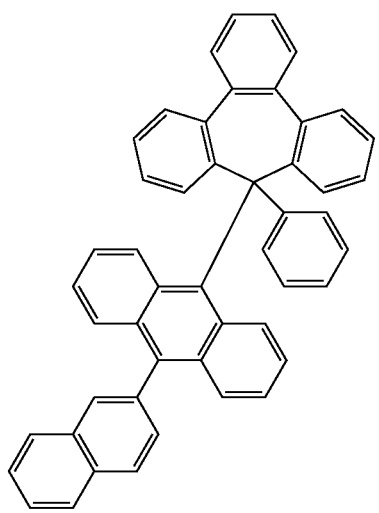
29
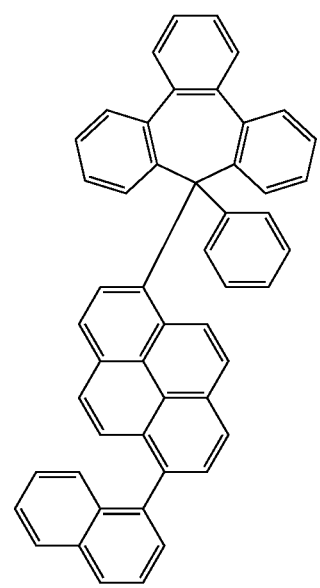
30
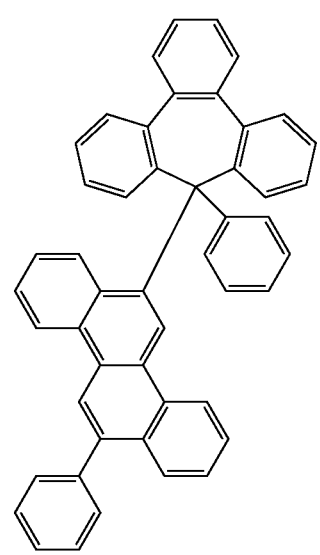
31
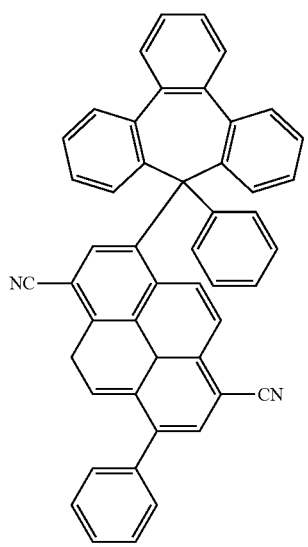
32
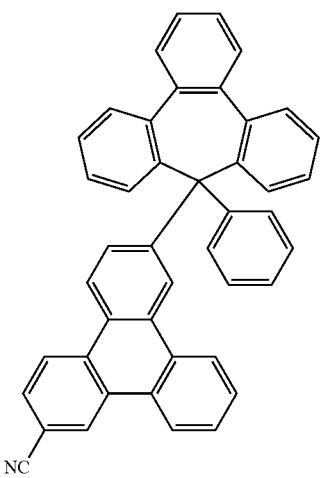
33
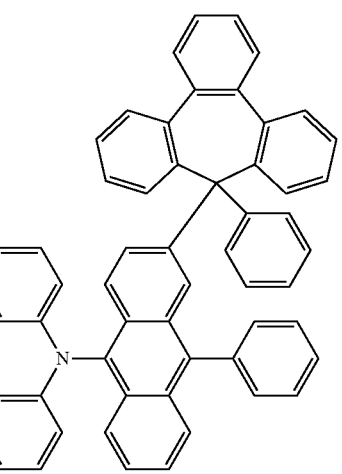

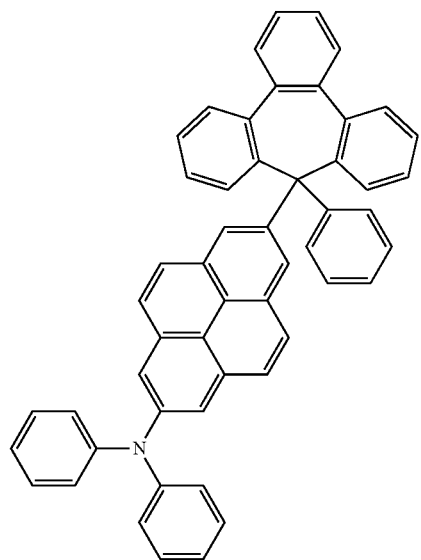
34
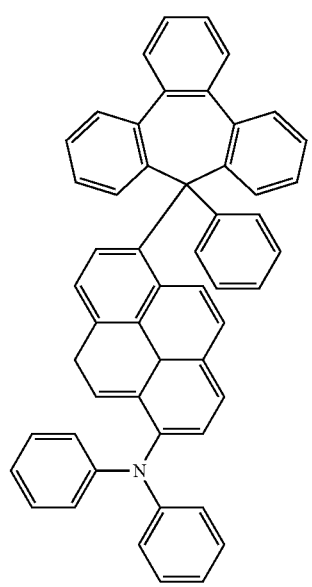
37
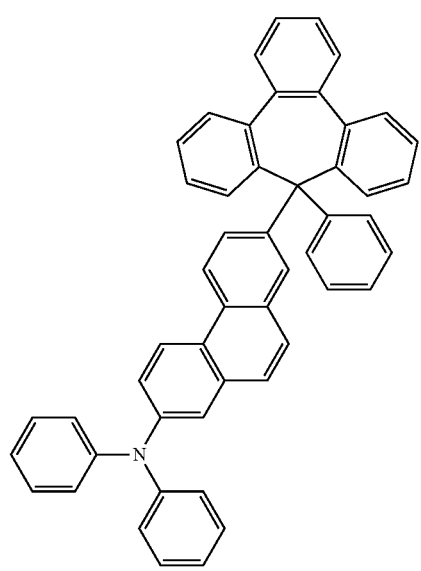
35
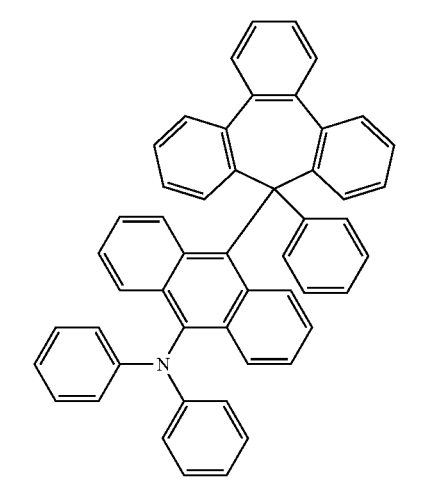
36
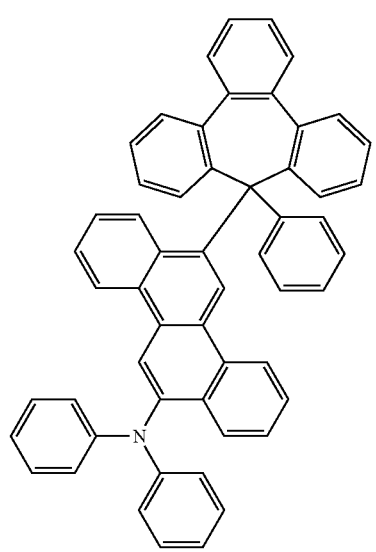
38

39
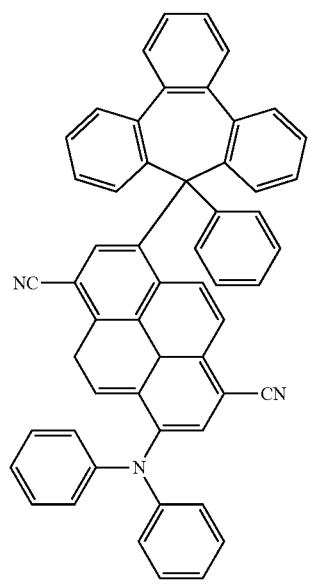
40
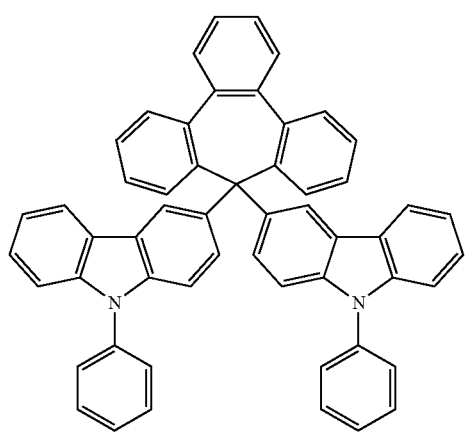
41
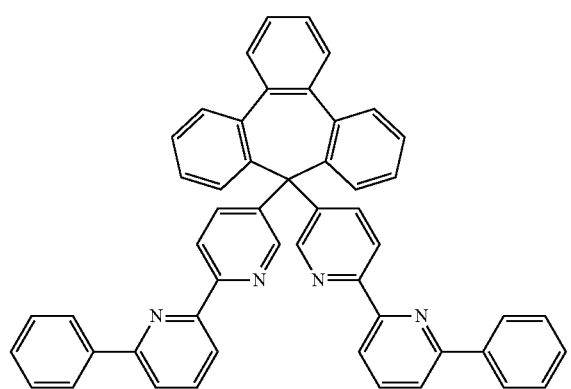
42
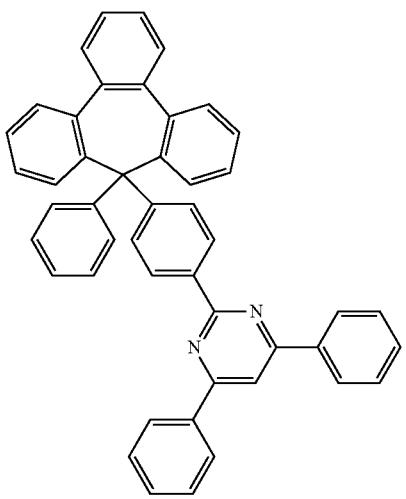
43
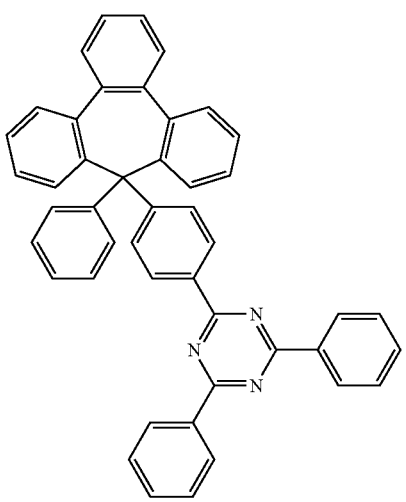
44
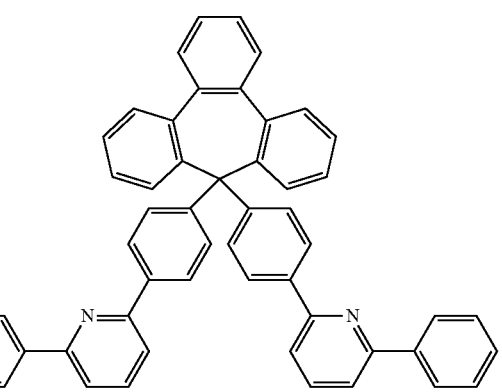

45
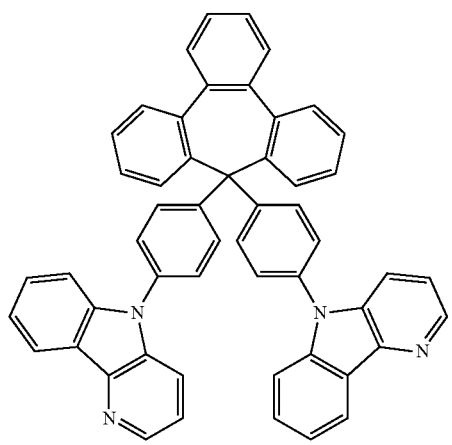
46
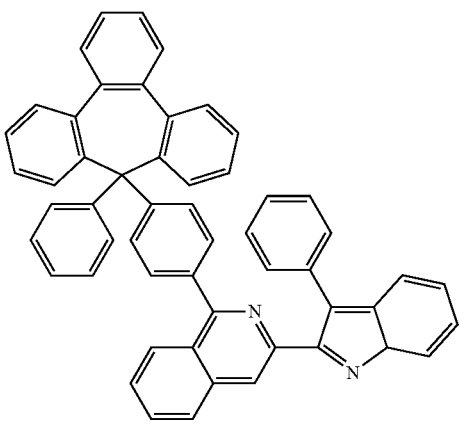
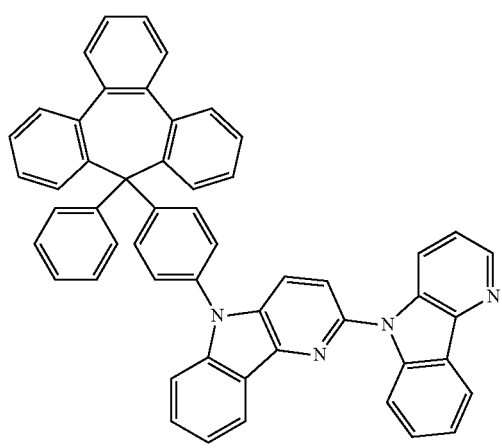
48
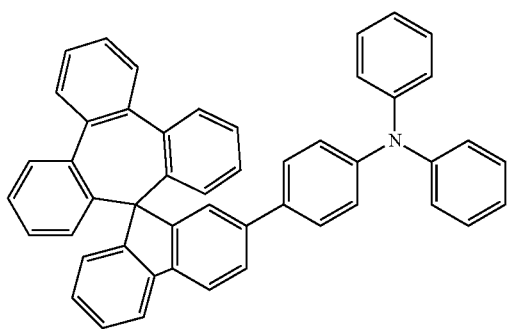
49
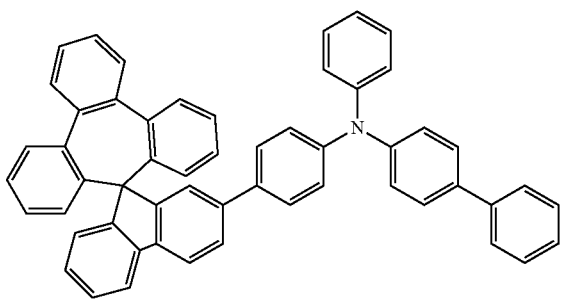
50
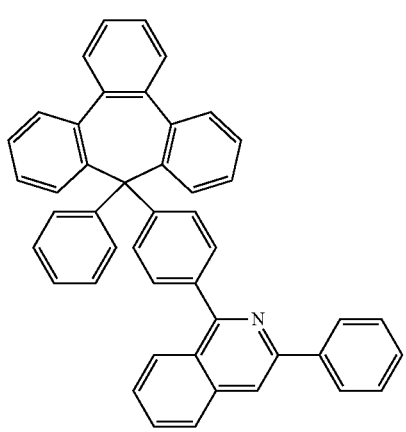
47
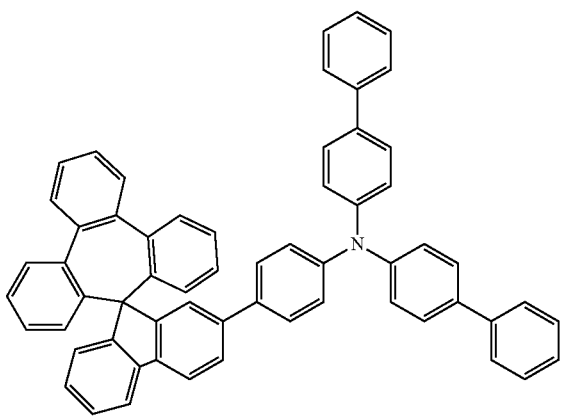
51

52
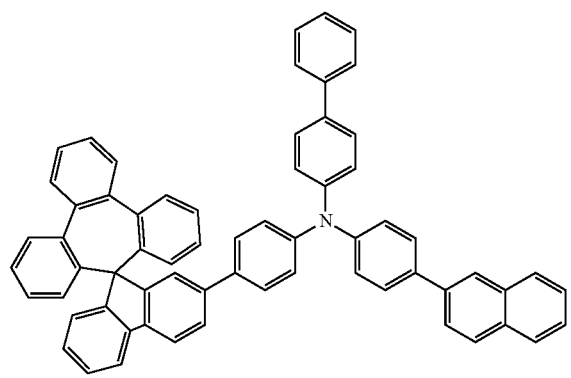
53
56
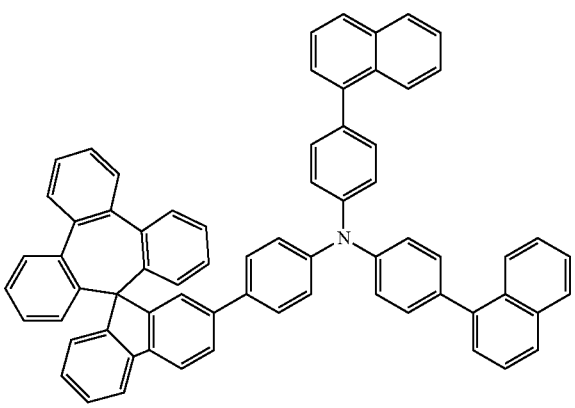
57
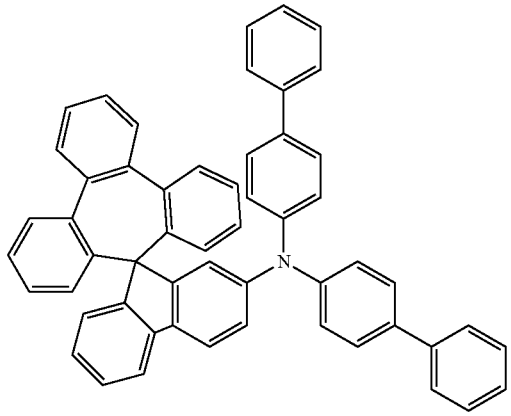
54
58
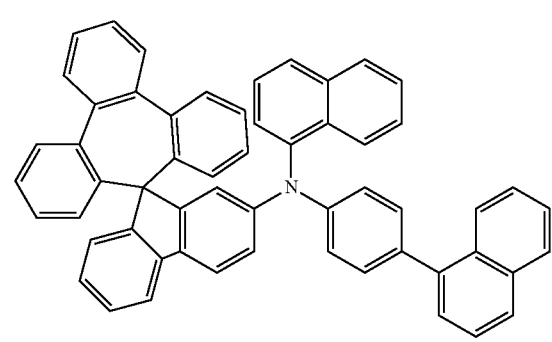
55
59
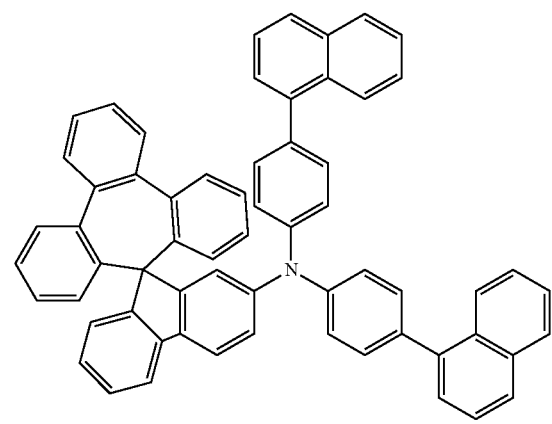

-continued
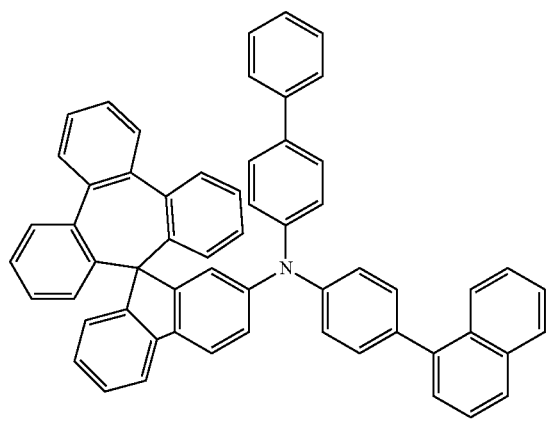
60
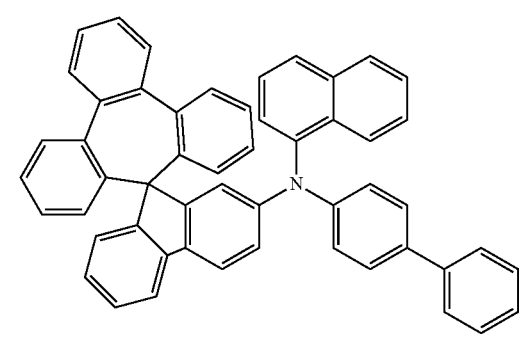
61
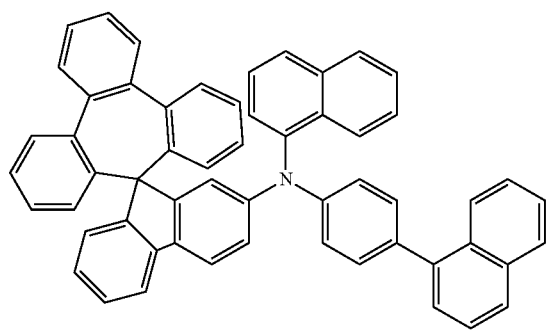
62
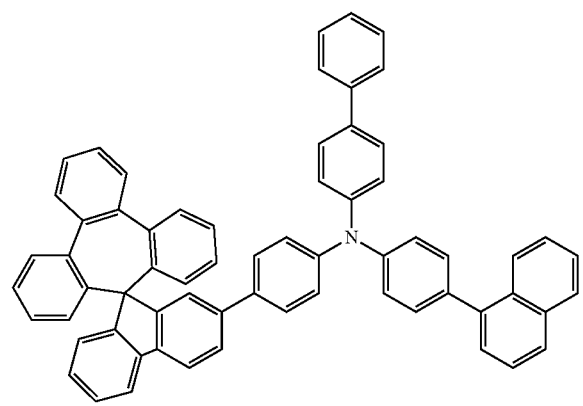
63
-continued
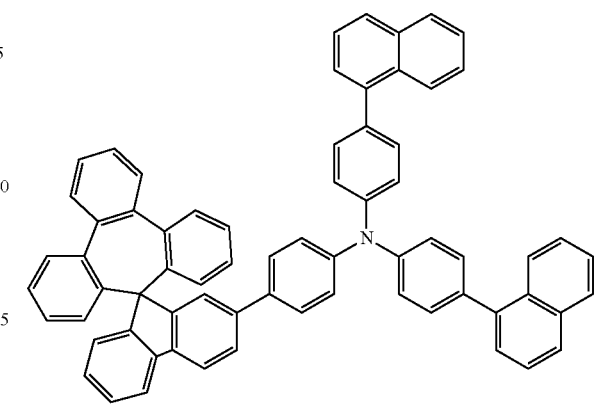
64
65
66
The polycyclic compound represented by Formula 1 may be one selected from Compounds 67 to 122 (collectively denoted as Compound Group 3). However, an embodiment is not limited thereto.

Formula Group 3
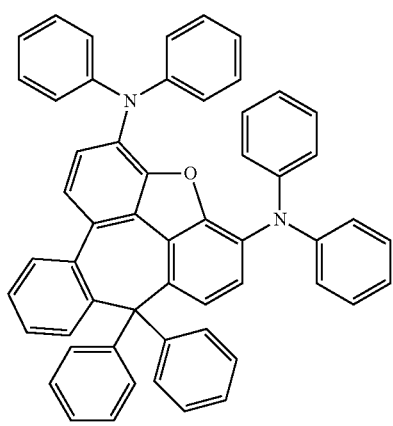
67
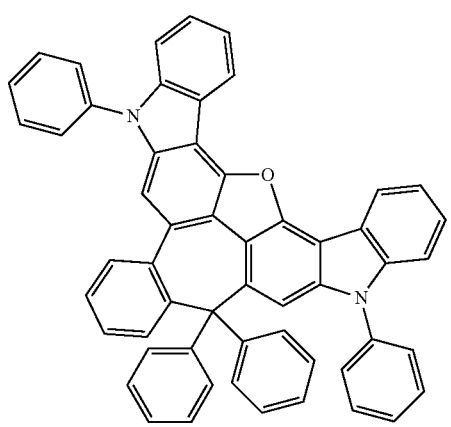
68
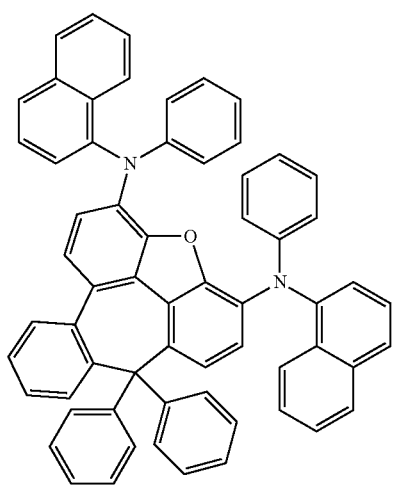
69
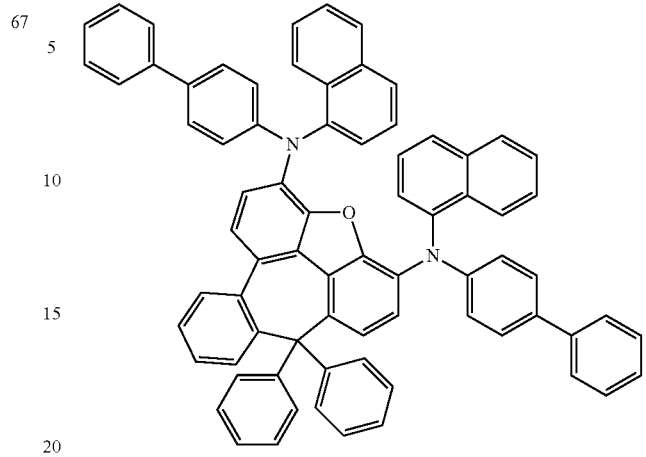
70
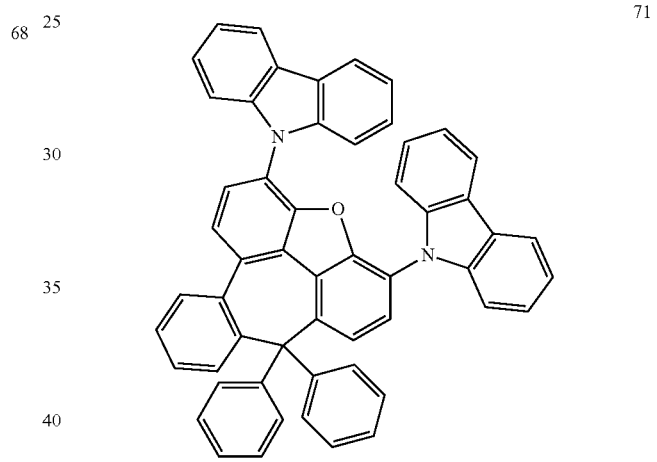
71
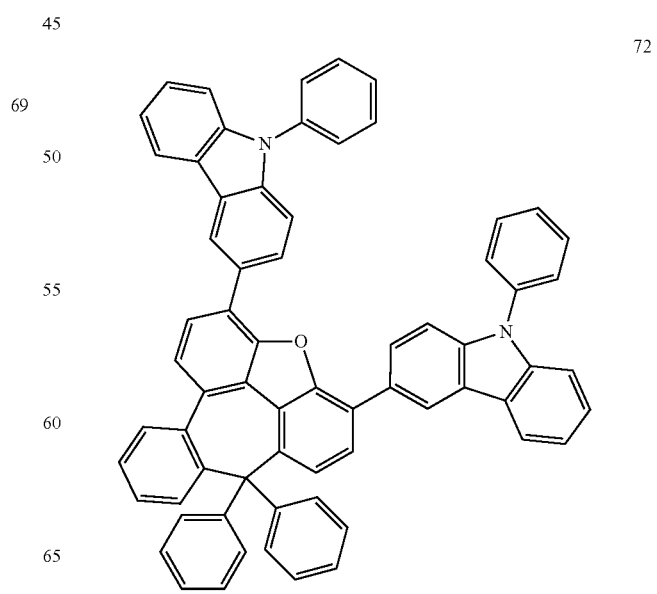
72

73
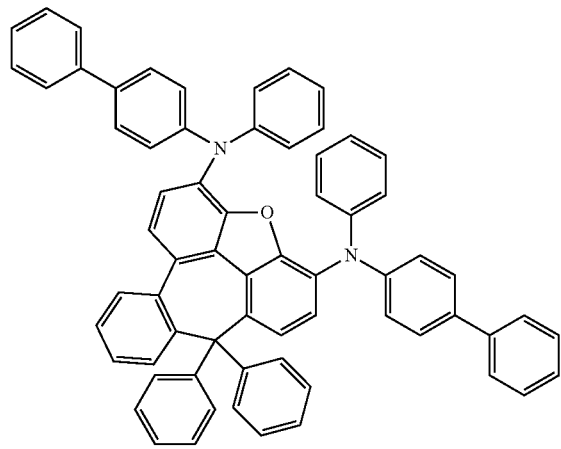
74
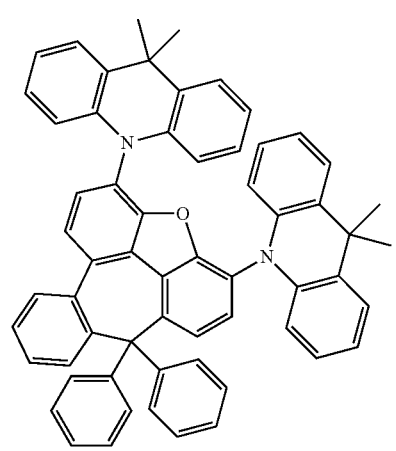
75
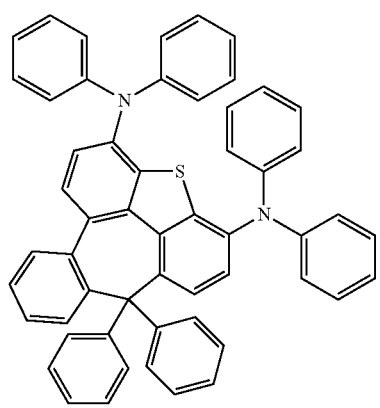
76
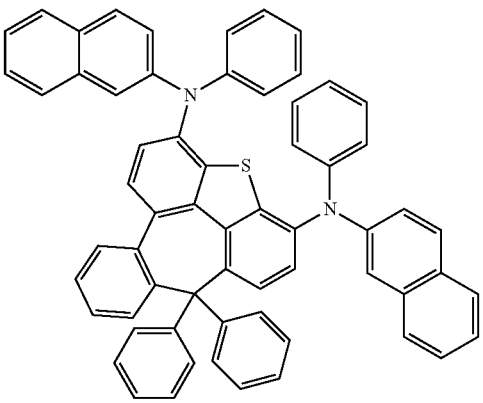
77
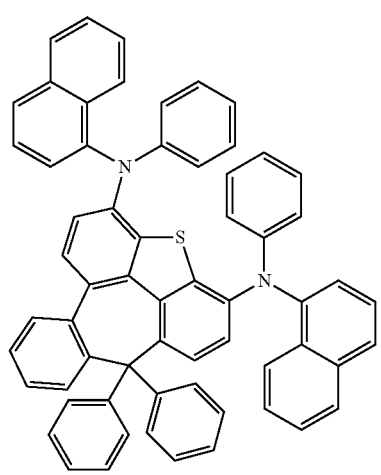
78
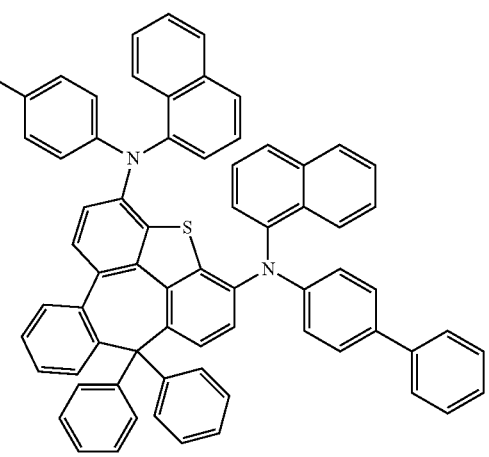

79
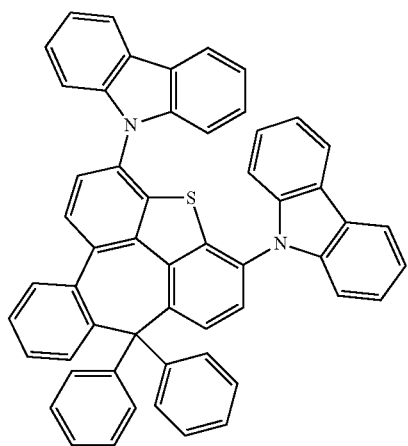
80
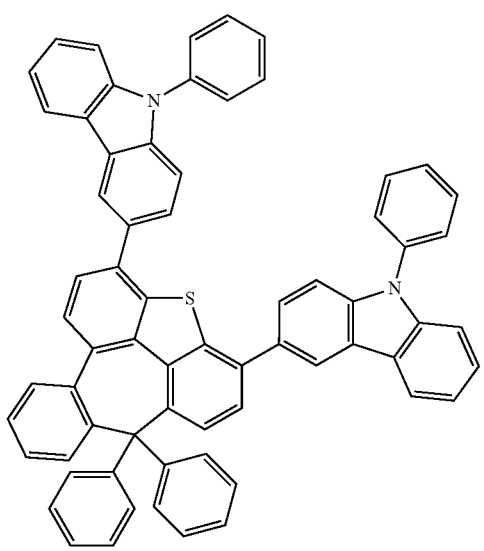
81
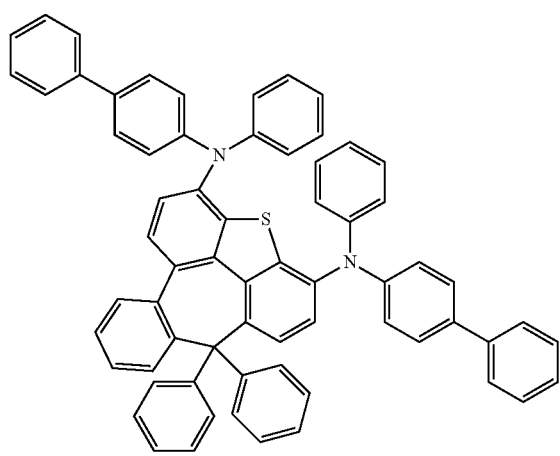
82
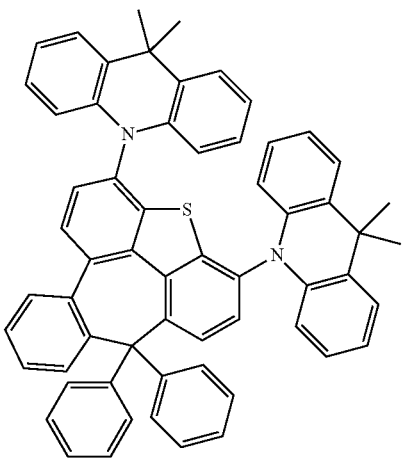
83
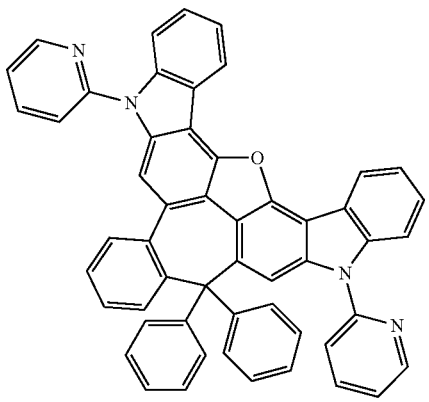
84
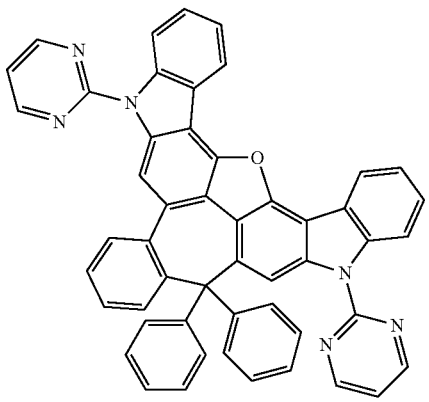

85
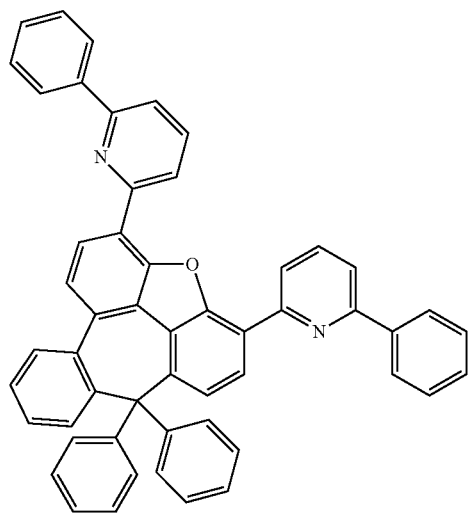
86
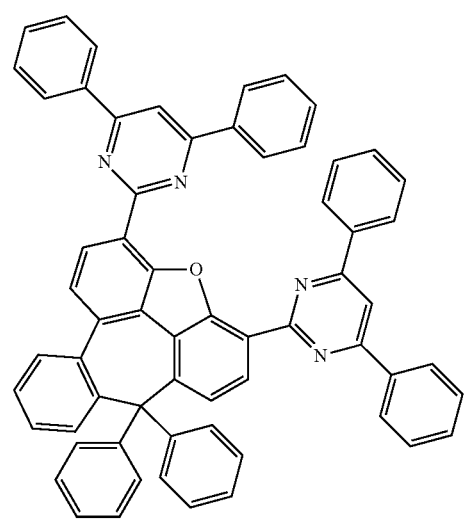
87
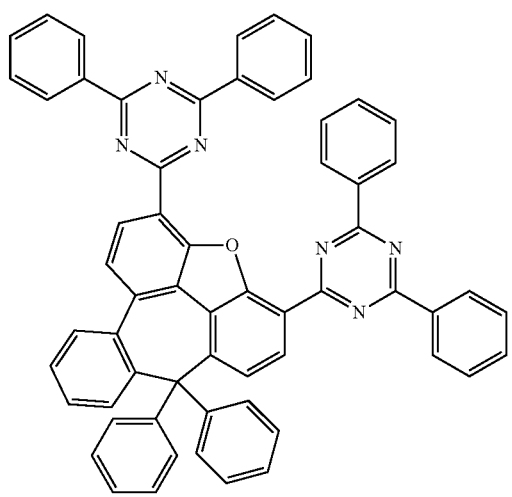
88
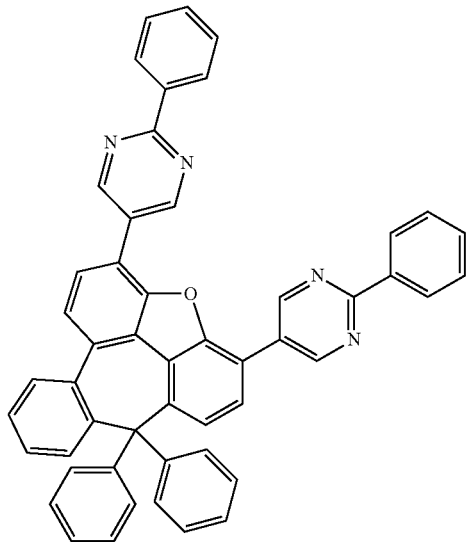
89
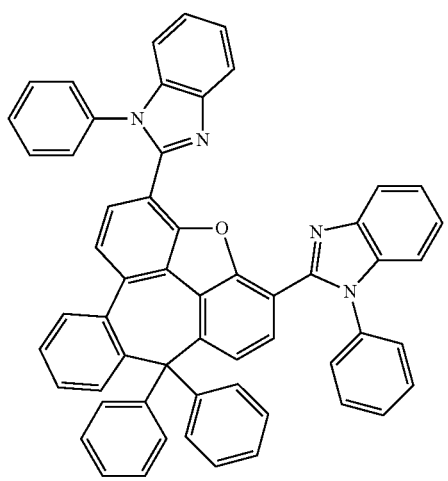
90
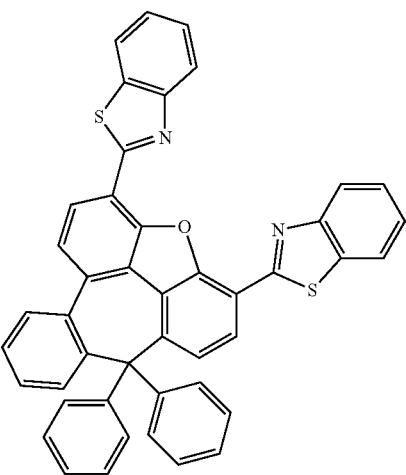

91
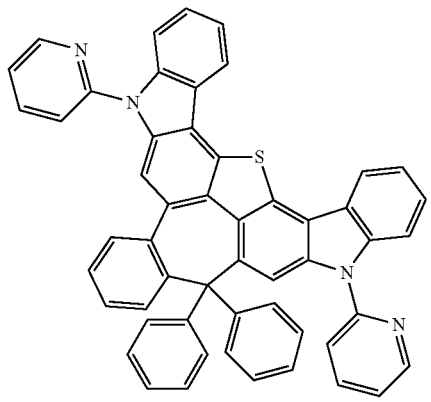
92
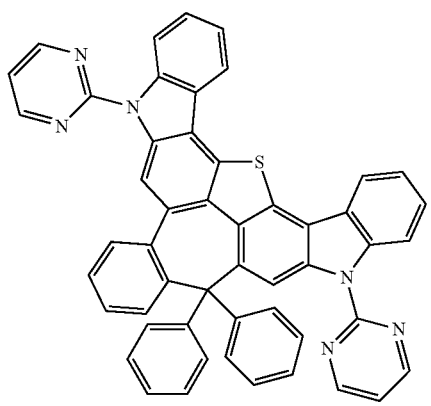
93
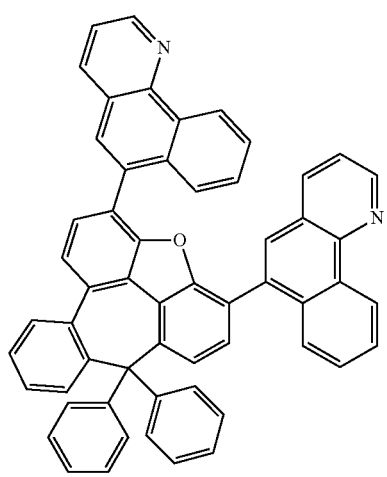
94
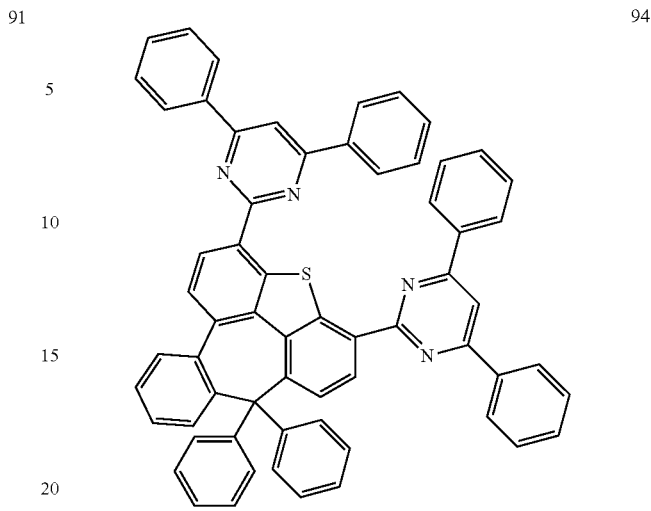
95
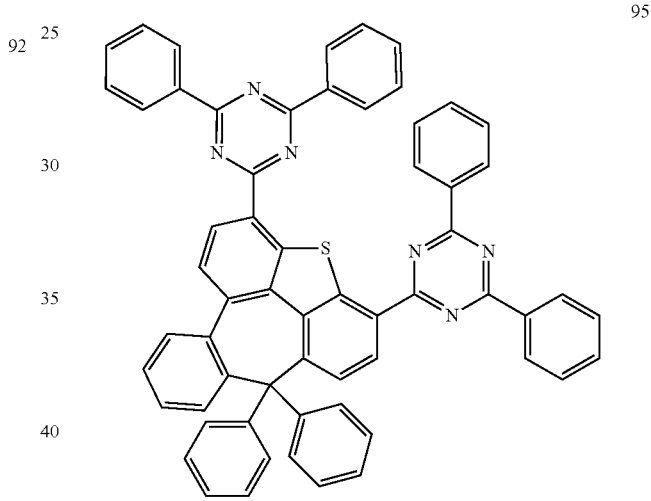
96
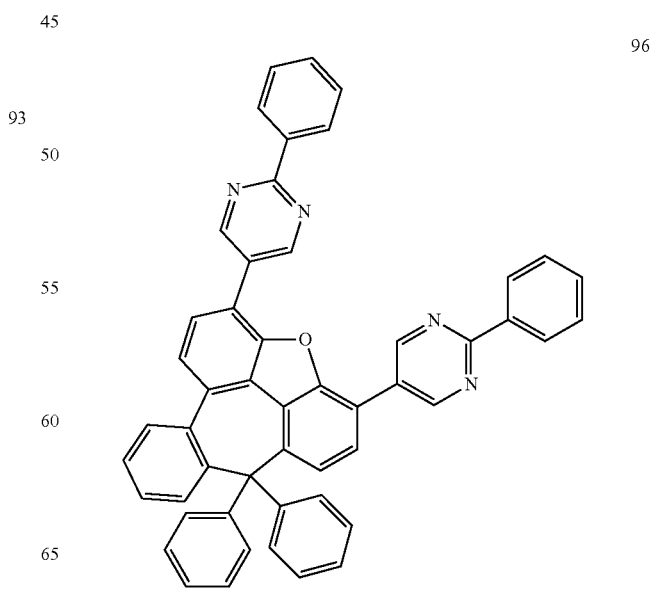

97
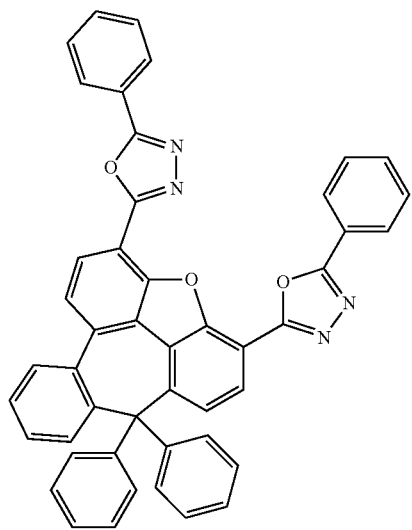
98
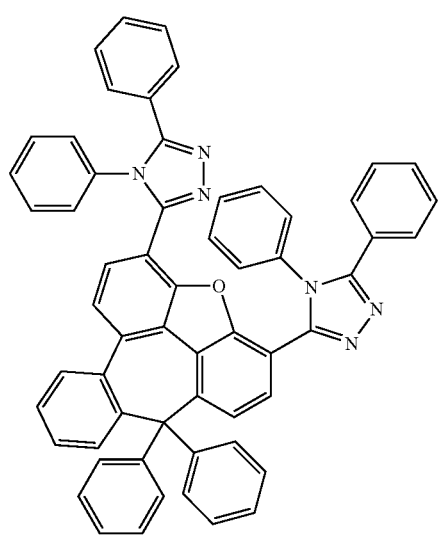
99
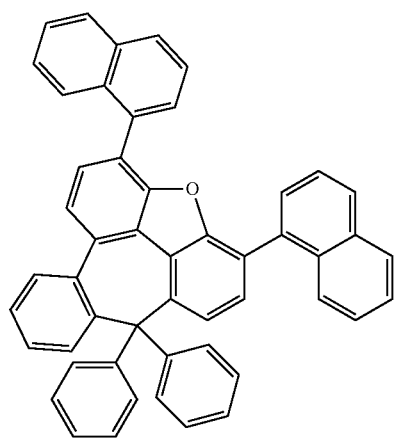
100
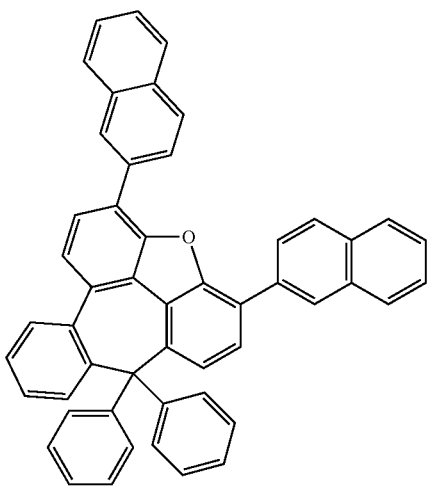
101
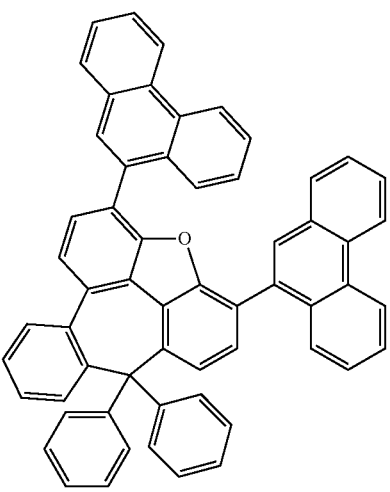
102
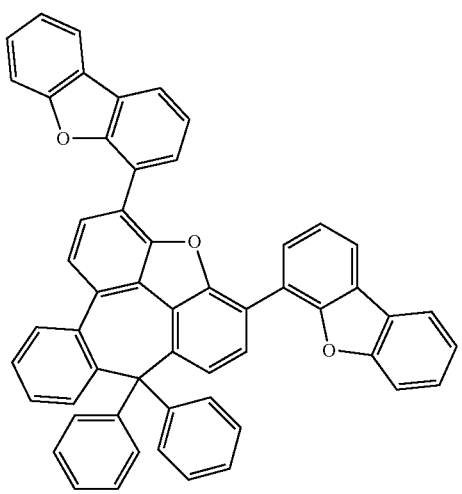

103
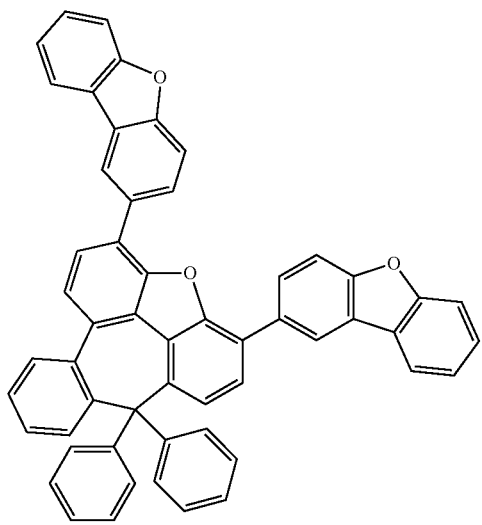
104
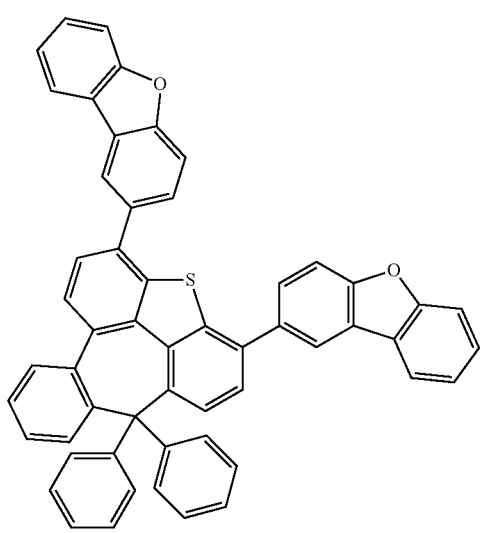
105
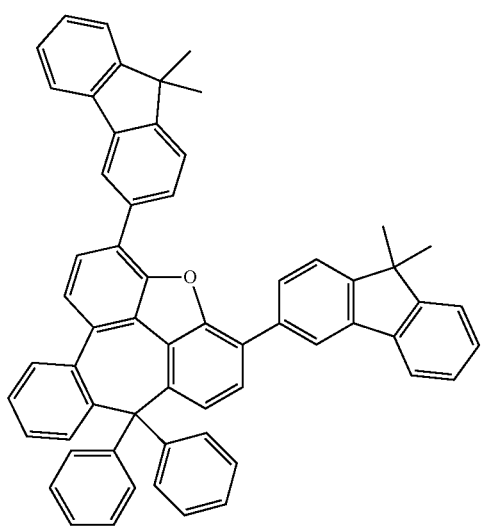
106
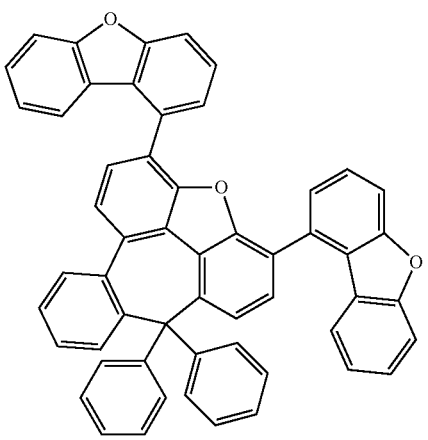
107
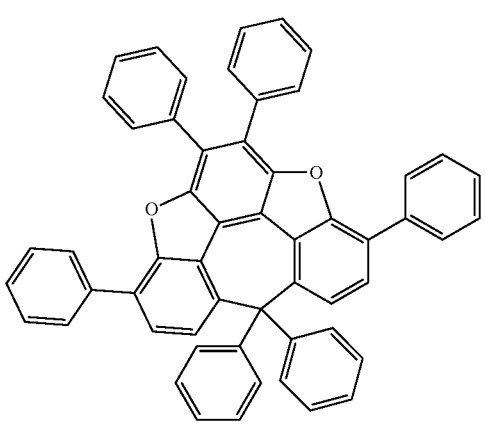
108
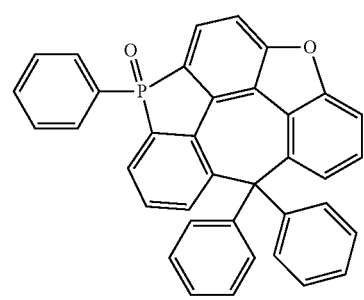
109
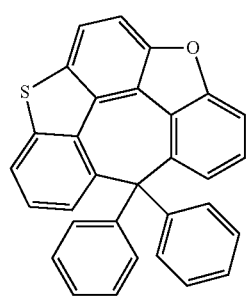

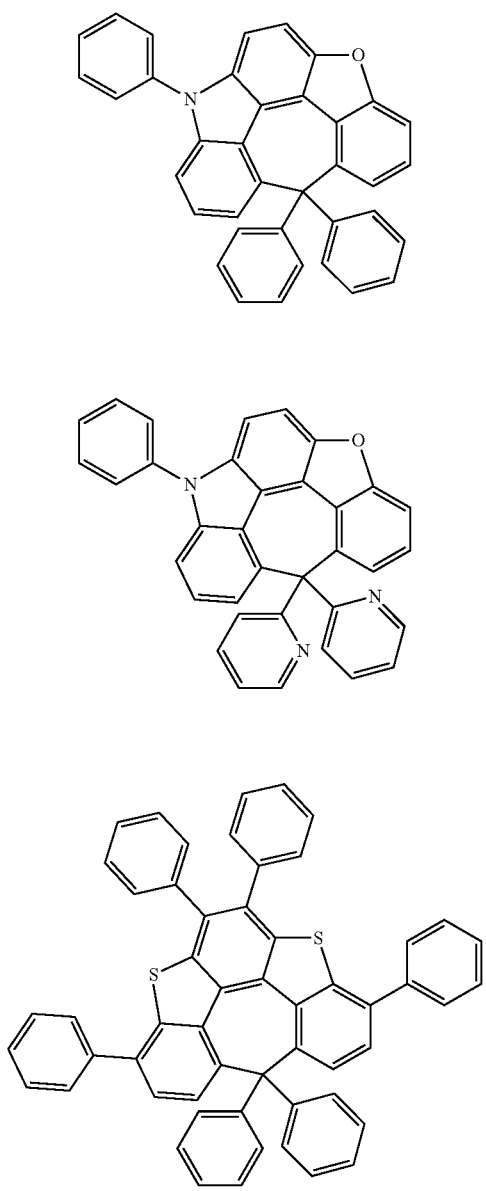

-continued

117
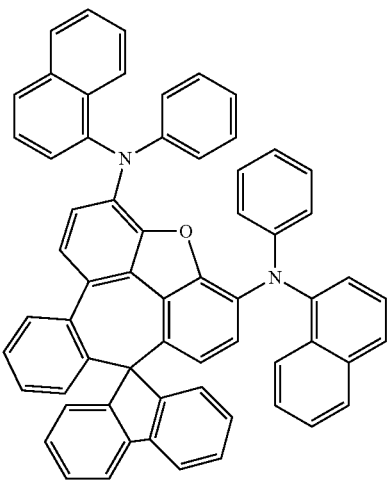

118
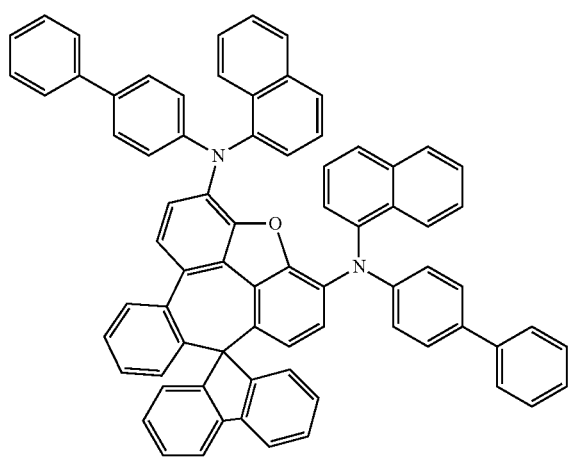

119
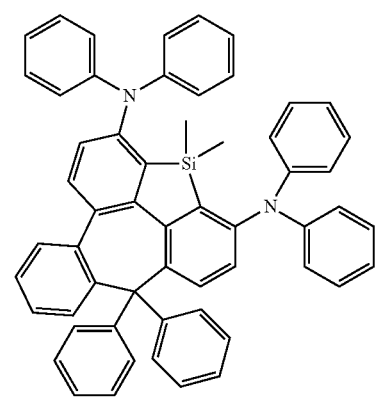

-continued

120
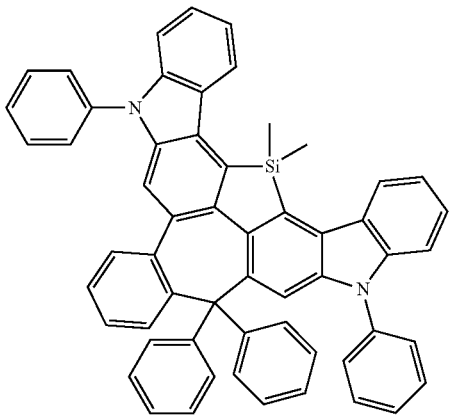

121
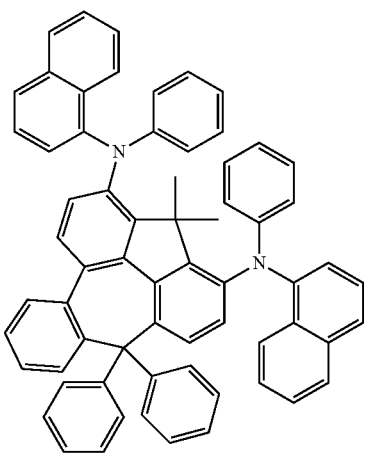

122
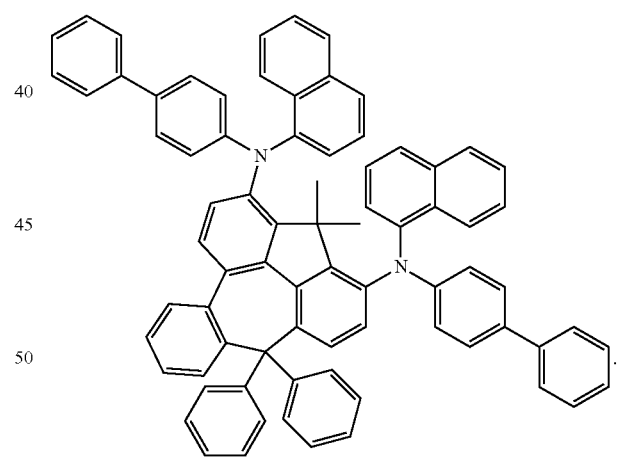

The polycyclic compound according to an embodiment of the inventive concept may be used as a material for an organic electroluminescence device. The polycyclic compound according to an embodiment of the inventive concept may improve the efficiency of an organic electroluminescence device. The polycyclic compound according to an embodiment of the inventive concept may increase the life of an organic electroluminescence device.

In the case where A of Formula 1 is represented by Formula 2-2, the polycyclic compound according to an embodiment of the inventive concept may include amine and may have strong electron tolerance. Amine and a spirophenanthrene-based compound may combine with each other, and the orbital diffusion of the highest occupied molecular orbital (HOMO) of the amine may be controlled, and the molecular symmetry may be collapsed to increase amorphous property. Accordingly, an organic electroluminescence device including the polycyclic compound according to an embodiment of the inventive concept may obtain long life and high emission efficiency.

In the case where A of Formula 1 is represented by Formula 2-1, the polycyclic compound according to an embodiment of the inventive concept includes tribenzocycloheptene moiety having high charge tolerance, and the life increase of an organic electroluminescence device may be attained. In addition, due to the large volume of the tribenzocycloheptene, the molecular symmetry may be collapsed, and the amorphous property may be improved, thereby improving the efficiency of an organic electroluminescence device. In addition, as shown in Formulae 12 to 16, in the case where two benzene rings of the tribenzocycloheptene moiety are connected via X, molecules may be fixed, and the charge tolerance may be improved.

Hereinafter, an organic electroluminescence device according to an embodiment of the inventive step will be explained in more detail. The following explanation will mainly focus on the differences between the above-described polycyclic compound and the compound according to the present embodiment of the inventive concept, and if a description of an element is not provided, the above-provided description of the corresponding element of the polycyclic compound according to an embodiment of the inventive concept will apply.

Figure 2:
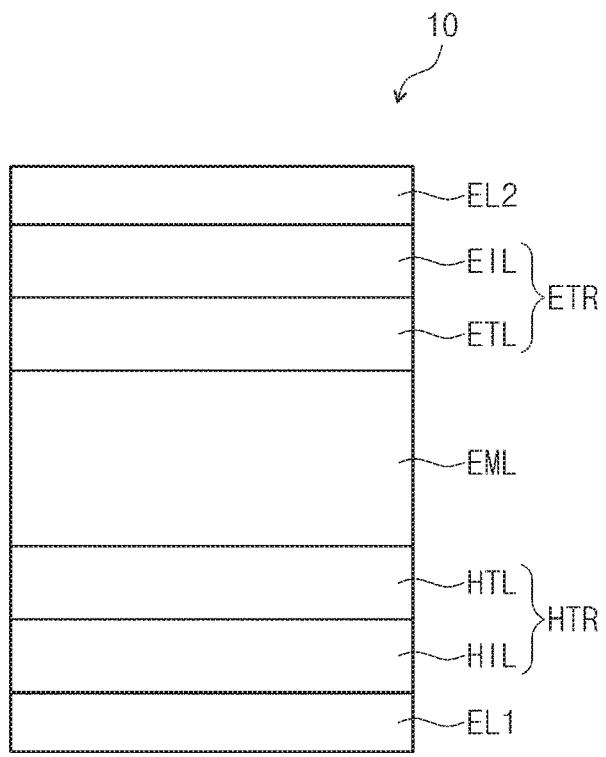
FIG. 2 is a cross-sectional view schematically illustrating an organic electroluminescence device according to an embodiment of the inventive concept.

FIG. 1 is a cross-sectional view schematically illustrating an organic electroluminescence device according to an embodiment of the inventive concept. FIG. 2 is a cross-sectional view schematically illustrating an organic electroluminescence device according to an embodiment of the inventive concept.

Referring to FIGS. 1 and 2, an organic electroluminescence device 10 according to an embodiment of the inventive concept may include a first electrode EL1, a hole transport region HTR, an emission layer EML, an electron transport region ETR, and a second electrode EL2.

The first electrode EL1 may be conductive. The first electrode EL1 may be a pixel electrode or an anode. The first electrode EL1 may be a transmissive electrode, a transflective electrode, or a reflective electrode. In the case where the first electrode EL1 is a transmissive electrode, the first electrode EL1 may be formed using a transparent metal oxide such as indium tin oxide (ITO), indium zinc oxide (IZO), zinc oxide (ZnO), and/or indium tin zinc oxide (ITZO). In the case where the first electrode EL1 is a transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). Also, the first electrode EL1 may include a plurality of layers including the reflective layer or transflective layer formed using (e.g., utilizing) any of the above materials, or a transparent conductive layer formed using ITO, IZO, ZnO, and/or ITZO.

Hereinafter, an embodiment in which the above-described polycyclic compound represented by Formula 1 according to an embodiment of the inventive concept is included in at least one of the hole transport region HTR and the emission layer EML will be explained. However, an embodiment is not limited thereto, and the polycyclic compound according to an embodiment of the inventive concept may be included in at least one organic layer provided between the first electrode EL1 and the second electrode EL2.

The hole transport region HTR is provided on the first electrode EL1. The hole transport region HTR may include at least one selected from a hole injection layer HIL, a hole transport layer HTL, a hole buffer layer, and an electron blocking layer. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL or a hole transport layer HTL, or may have a structure of a single layer formed using a hole injection material and a hole transport material. In some embodiments, the hole transport region HTR may have a structure of a single layer formed using a plurality of different materials, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation, where the layers are laminated on the first electrode in the stated order.

The hole transport region HTR may be formed using various methods such as a vacuum deposition method, a spin coating method, a cast method, a Langmuir-Blodgett (LB) method, an inkjet printing method, a laser printing method, and/or a laser induced thermal imaging (LITI) method.

The hole transport region HTR may include the above-described polycyclic compound according to an embodiment of the inventive concept. In particular, the hole transport region HTR may include the polycyclic compound represented by Formula 1:

Formula 1

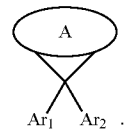

Descriptions of A, $Ar_1$, and $Ar_2$ are the same as those provided above.

The hole transport region HTR may include the polycyclic compound represented by Formula 3:

Formula 3

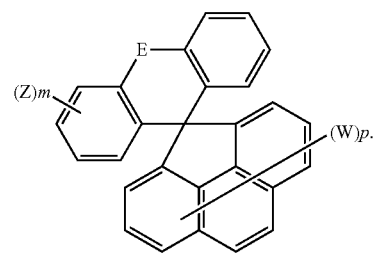

Descriptions of substituents in Formula 3 are the same as those provided above.

The hole transport region HTR may include the polycyclic compound represented by Formula 5:

Formula 5

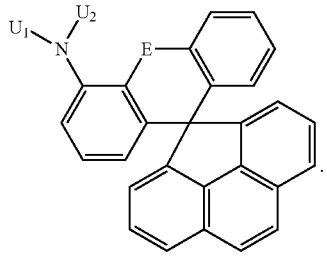

Descriptions of substituents in Formula 5 are the same as those provided above.

In the case where the hole transport region HTR includes the polycyclic compound represented by Formula 3 or 5, the polycyclic compound may include amine and may have strong electron tolerance. In addition, amine and a spirophenanthrene-based compound may combine with each other, and the orbital diffusion of the highest occupied molecular orbital (HOMO) of the amine may be controlled, and the molecular symmetry may be collapsed to increase amorphous property. Accordingly, an organic electroluminescence device according to an embodiment of the inventive concept may obtain the long life and high emission efficiency.

The hole transport region HTR may include the polycyclic compound represented by one of the above-described Formulae 6, 6-1, 7 and 8. In this case, the polycyclic compound may include a tribenzocycloheptene moiety and amine, and the life of an organic electroluminescence device may be increased due to the high charge tolerance of the tribenzocycloheptene. In addition, due to the large volume of the tribenzocycloheptene, the molecular symmetry may be collapsed, and the amorphous property may be improved, thereby improving the efficiency of an organic electroluminescence device.

Formula 6

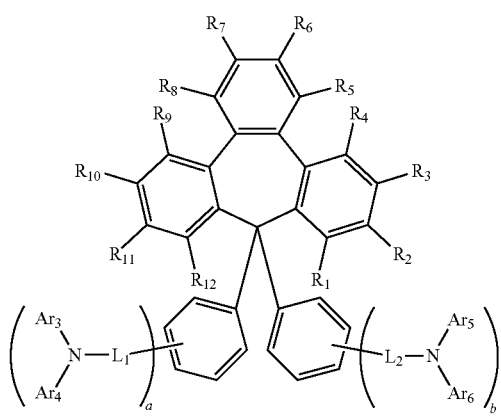

[Formula 6-1]

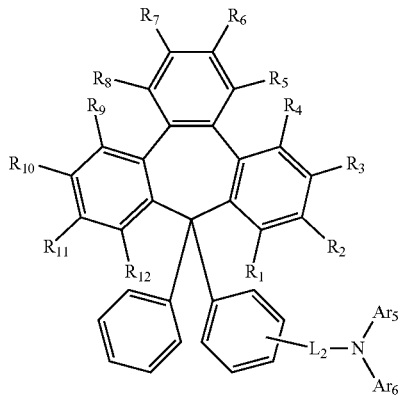

Formula 7

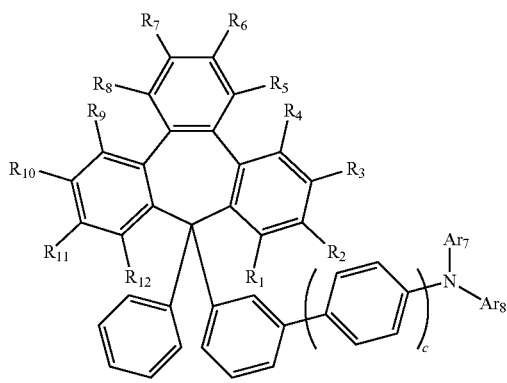

Formula 8

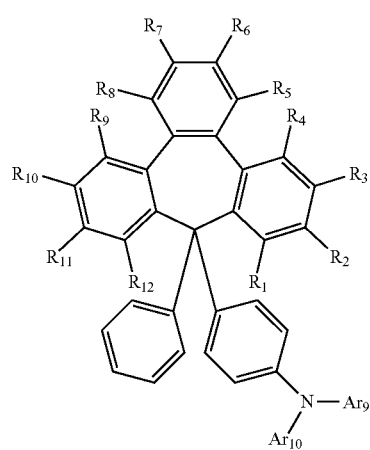

Descriptions of substituents in Formulae 6, 6-1, 7, and 8 are the same as those provided above.

The hole transport region HTR may include the polycyclic compound represented by Formula 10. In this case, the polycyclic compound may include a tribenzocycloheptene moiety and amine, and the high hole transport property of the amine may be maintained, and the life of an organic electroluminescence device may be increased due to the high charge tolerance of the tribenzocycloheptene. In addition, due to the large volume of the tribenzocycloheptene, the molecular symmetry may be collapsed, the amorphous property may be improved, and the efficiency may be improved.

Formula 10

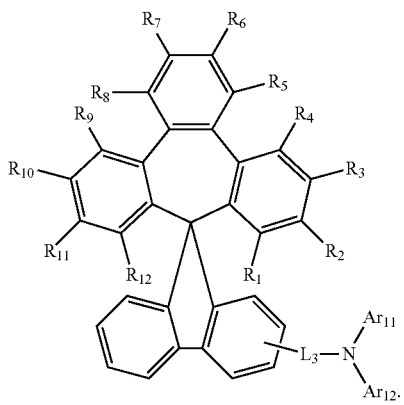

Descriptions of substituents in Formula 10 are the same as those provided above.

A layer including the above-described polycyclic compound represented by Formula 1 according to an embodiment of the inventive concept may be the hole transport layer HTL. The hole transport layer HTL may include at least one polycyclic compound represented by Formula 1. The hole transport layer HTL may further include any suitable material other than the polycyclic compound represented by Formula 1.

In the case where the hole transport layer HTL includes the polycyclic compound according to an embodiment of the inventive concept, the hole injection layer HIL may further include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, etc.

In the case where the hole transport layer HTL does not include the polycyclic compound represented by Formula 1 according to an embodiment of the inventive concept, the hole transport layer HTL may include any suitable material. For example, the hole transport layer HTL may include a carbazole derivative (such as N-phenyl carbazole and/or polyvinyl carbazole), a fluorine-based derivative, N,N'-bis(3-methylphenyl)-N,N'-diphenyl-[1,1-biphenyl]-4,4'-diamine (TPD), a triphenylamine-based derivative (such as 4,4',4''-tris(N-carbazolyl)triphenylamine (TCTA)), N,N'-di(1-naphthyl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, for example, from about 100 Å to about 1,000 Å. In the case where the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. When the thicknesses of the hole transport region HTR, the hole injection layer HIL, and the hole transport layer HTL satisfy any of the above-described ranges, satisfactory (or suitable) hole transport properties may be obtained without the substantial increase of a driving voltage.

The hole transport region HTR may further include a charge generating material, other than the above-described materials, to improve conductivity. The charge generating material may be dispersed in the hole transport region HTR uniformly or non-uniformly. The charge generating material may be, for example, a p-dopant. The p-dopant may be one selected from a quinone derivative, a metal oxide, and a cyano group-containing compound, without limitation. Non-limiting examples of the p-dopant may include a quinone derivative (such as tetracyanoquinodimethane (TCNQ) and/or 2,3,5,6-tetrafluoro-tetracyanoquinodimethane (F4-TCNQ)), a metal oxide (such as tungsten oxide and/or molybdenum oxide), without limitation.

As described above, the hole transport region HTR may further include one selected from the hole buffer layer and the electron blocking layer, in addition to the hole injection layer HIL and the hole transport layer HTL. The hole buffer layer may compensate for an optical resonance distance according to the wavelength of light emitted from the emission layer EML, and increase light emission efficiency. Any of the materials included in the hole transport region HTR may be used as materials included in the hole buffer layer. The electron blocking layer is a layer that may prevent or reduce electron injection from the electron transport region ETR to the hole transport region HTR.

The emission layer EML may be provided on the hole transport region HTR. The thickness of the emission layer EML may be, for example, from about 100 Å to about 300 Å. The emission layer EML may have a single layer formed using a single material, a single layer formed using a plurality of different materials, or a multilayer structure having a plurality of layers formed using a plurality of different materials.

The emission layer EML may include the polycyclic compound represented by Formula 1 according to an embodiment of the inventive concept. In this case, the hole transport region HTR may include or not include the polycyclic compound represented by Formula 1 according to an embodiment of the inventive concept. In some embodiments, the emission layer EML may include the compound represented by Formula 1 according to an embodiment of the inventive concept as a host.

The emission layer EML may include at least one polycyclic compound represented by Formula 1. The emission layer EML may further include any suitable material other than the polycyclic compound represented by Formula 1. For example, the emission layer EML may further include a fluorescent material including one selected from spiro-DPVBi, spiro-6P, distyryl-benzene (DSB), distyryl-arylene (DSA), a polyfluorene (PFO)-based polymer, and a poly(p-phenylene vinylene) (PPV)-based polymer. However, an embodiment is not limited thereto, and the emission layer EML may include a phosphorescent material.

The emission layer EML may include the polycyclic compound represented by Formula 11:

Formula 11

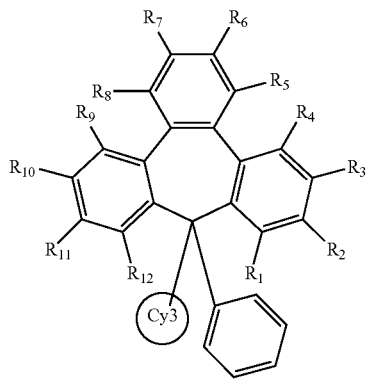

Descriptions of the substituents of Formula 11 are the same as those provided above.

When the polycyclic compound includes a tribenzocycloheptene moiety and an aryl group of three- or four-membered ring such as anthracenyl group (e.g., Cy3 may be anthracenyl group), good emission characteristic of anthracenyl group may be maintained and the life of the organic electroluminescence device may be further increased due to the high charge tolerance of the tribenzocycloheptene. In addition, due to the large volume of the tribenzocycloheptene, molecular symmetry may be collapsed and amorphous property may be improved, thereby improving the efficiency.

In the case where the polycyclic compound represented by Formula 1 according to an embodiment of the inventive concept is included in the emission layer EML, the emission layer EML may further include any suitable material. For example, the emission layer EML may include a carbazole derivative, a triarylamine derivative, a nitrogen-containing polycyclic derivative, a thiophene derivative, a furan derivative, an azacarbazole derivative, a diazacarbazole derivative, etc., as a dopant, and may include a condensed polycyclic aromatic compound as a dopant. For example, the EML may include an anthracene derivative, a naphthalene derivative, a phenanthrene derivative, a pyrene derivative, a tetracene derivative, a pentacene derivative, a chrysene derivative, a perylene derivative, a rubrene derivative, a vinyl anthracene derivative, a diaminocarbazole derivative, etc., as the dopant. However, a dopant material is not limited thereto. For example, the dopant material may include a copper complex, a platinum complex, and/or an iridium complex.

The emission layer EML may have a thickness, for example, from about 10 nm to about 60 nm.

The electron transport region ETR may be provided on the emission layer EML. The electron transport region ETR may include at least one selected from an electron blocking layer, an electron transport layer ETL, and an electron injection layer EIL, without limitation.

The electron transport region ETR may have a single layer formed using a single material, a single layer formed using a plurality of different materials, or a multilayer structure including a plurality of layers formed using a plurality of different materials.

For example, the electron transport region ETR may have the structure of a single layer such as the electron injection layer EIL or the electron transport layer ETL, or the structure of a single layer formed using an electron injection material and an electron transport material. In addition, the electron transport region ETR may have the structure of a single layer formed using a plurality of different materials, or a structure of electron transport layer ETL/electron injection layer EIL, or hole blocking layer/electron transport layer ETL/electron injection layer EIL, without limitation, where the layers are laminated on the first electrode EL1 in the stated order. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and/or a laser induced thermal imaging (LITI) method.

In the case where the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1, O8)-(1,1'-biphenyl-4-olato) aluminum (BAlq), beryllium bis(benzoquinolin-10-olate (Bebq2), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies any of the above-described ranges, satisfactory (or suitable) electron transport properties may be obtained without the substantial increase of a driving voltage.

In the case where the electron transport region ETR includes the electron injection layer EIL, a metal such as Al, Ag, Li, Mg, and/or Ca, and/or a mixture thereof may be included. However, an embodiment is not limited thereto. For example, the electron injection layer EIL may include LiF, lithium quinolate (LiQ), $Li_2O$, BaO, NaCl, CsF, a metal in lanthanides (such as Yb), or a metal halide (such as RbCl and/or RbI), without limitation. The electron injection layer EIL also may be formed using a mixture material of an electron transport material and an insulating organo-metal salt. The organo-metal salt may be a material having an energy band gap of about 4 eV or more. The organo-metal salt may include, for example, a metal acetate, a metal benzoate, a metal acetoacetate, a metal acetylacetonate, and/or a metal stearate. The thickness of the electron injection layer EIL may be from about 1 Å to about 100 Å, and from about 3 Å to about 90 Å. In the case where the thickness of the electron injection layer EIL satisfies any of the above described ranges, satisfactory (or suitable) electron injection properties may be obtained without inducing the substantial increase of a driving voltage.

The electron transport region ETR may include a hole blocking layer, as described above. The hole blocking layer may include, for example, at least one selected from 2,9-dimethyl-4,7-diphenyl-1,10-phenanthroline (BCP) and 4,7-diphenyl-1,10-phenanthroline (Bphen), without limitation.

The second electrode EL2 may be provided on the electron transport region ETR. The second electrode EL2 may be a common electrode or a cathode. The second electrode EL2 may be a transmissive electrode, a transflective electrode or a reflective electrode. In the case where the second electrode EL2 is a transmissive electrode, the second electrode EL2 may include a transparent metal oxide, for example, ITO, IZO, ZnO, ITZO, etc.

In the case where the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). The second electrode EL2 may have a multilayered structure including a reflective layer or a transflective layer formed using any of the above-described materials or a transparent conductive layer formed using ITO, IZO, ZnO, ITZO, etc.

Even though not shown, the second electrode EL2 may be connected (e.g., coupled) with an auxiliary electrode. If the second electrode EL2 is connected with the auxiliary electrode, the resistance of the second electrode EL2 may decrease.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and light may be emitted via the transition of the excitons from an excited state to a ground state.

In the case where the organic electroluminescence device 10 is a top emission type (e.g., top emission organic electroluminescence device), the first electrode EL1 may be a reflective electrode, and the second electrode EL2 may be a transmissive electrode or a transflective electrode. In the case where the organic electroluminescence device 10 is a bottom emission type (e.g., bottom emission organic electroluminescence device), the first electrode EL1 may be a transmissive electrode or a transflective electrode, and the second electrode EL2 may be a reflective electrode.

The organic electroluminescence device according to an embodiment of the inventive concept includes the polycyclic compound represented by Formula 1, thereby increasing emission efficiency and life. The polycyclic compound represented by Formula 1 may include a tribenzocycloheptene moiety as a core structure, and due to the high charge tolerance of the tribenzocycloheptene, the life of the organic electroluminescence device may be increased. In addition, due to the large volume of the tribenzocycloheptene, the amorphous property of the molecular structure may be improved, thereby attaining high efficiency.

Hereinafter, the inventive concept will be explained more particularly referring to particular preparation methods, embodiments and comparative embodiments. The following embodiments are only for illustration and to assist the understanding of the inventive concept, and the scope of the inventive concept is not limited thereto.

The polycyclic compound represented by Formula 1 according to an embodiment of the inventive concept may be synthesized, for example, according to the following method. However, an embodiment is not limited thereto.

Preparation Method

1. Synthesis of Compound 9

Synthesis of Compound A

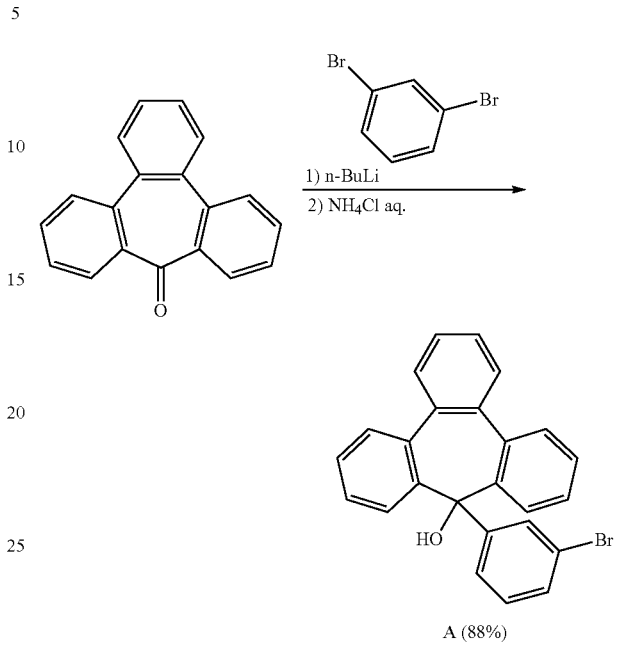

Under an argon (Ar) atmosphere, 5.00 g of 1,3-dibromobenzene was added to a 200 mL, three-necked flask, and the temperature was set to −78° C. in 40 mL of a THF solvent. Then, 13.3 mL of a hexane solution of n-BuLi (1.60 M) was slowly added thereto, followed by stirring the resulting mixture at about −78° C. for about 1 hour. After that, 50 mL of a THF solution with 5.43 g of 9H-tribenzo [a,c,e]cyclohepten-9-one was slowly added dropwise thereto, and the temperature was elevated to room temperature, followed by stirring for about 2 hours. An organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 7.70 g (yield 88%) of Compound A as a white solid.

The molecular weight of Compound A measured by FAB-MS (Fast Atom Bombardment-Mass Spectrometry) was 345.

Synthesis of Compound B

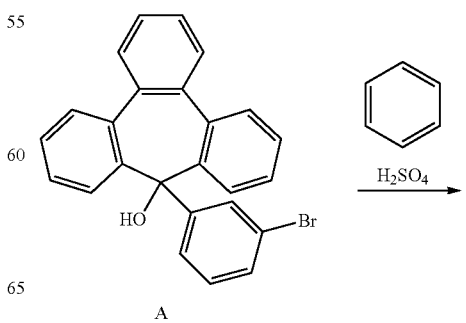

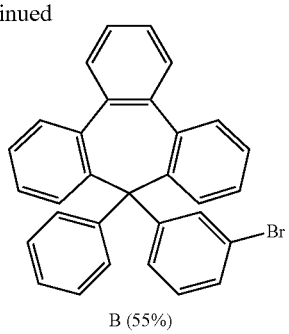

B (55%)

Under an argon (Ar) atmosphere, in a 100 mL of a three-necked flask, 4.13 g of Compound A was dissolved in 25 mL of benzene, and 0.8 mL of sulfuric acid ($H_2SO_4$) dissolved in 3 mL of benzene was added thereto, followed by stirring the resulting mixture at about 80° C. for about 5 hours. After air-cooling the obtained product, an $NaHCO_3$ aqueous solution was added thereto in order to adjust the pH to 7. An organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 2.60 g (yield 55%) of Compound B as a white solid.

The molecular weight of Compound B measured by FAB-MS was 473.

Synthesis of Compound 9

Under an argon (Ar) atmosphere, 2.37 g of Compound B, 1.61 g of bis(4-biphenylyl)amine, 0.264 g of bis(dibenzylideneacetone)palladium(0) ($Pd(dba)_2$), 0.33 g of tri-tert-butylphosphine (($t$-Bu)$_3$P), and 1.93 g of sodium tert-butoxide (NaOt-Bu) were added to a 200 mL, three-necked flask, followed by heating, refluxing and stirring the resulting mixture in 60 mL of a toluene solvent for about 8 hours. After air-cooling the obtained product, water was added thereto, an organic layer was separated therefrom, and solvents were distilled. The crude product thus obtained was separated by silica gel column chromatography (using a mixture solvent of dichloromethane and hexane), and then, recrystallized using a mixture solvent of toluene and hexane to obtain 2.50 g (yield 70%) of Compound 9 as a white solid.

The molecular weight of Compound 9 measured by FAB-MS was 714. In addition, the chemical shift values (δ) of Compound 9 measured by $^1$H-NMR (CDCl$_3$) were 8.12 (d, 2H, J=7.20 Hz), 7.93 (d, 1H, J=8.10 Hz), 7.89-7.82 (m, 5H), 7.80-7.74 (m, 4H), 7.72 (s, 1H), 7.71-7.63 (m, 4H), 7.48-7.41 (m, 12H).

2. Synthesis of Compound 10

Compound 10 was synthesized by the same (or substantially the same) method as the synthesis of Compound 9 except for using N-[4-(1-naphthalenyl)phenyl]-1-naphthalenamine instead of bis(4-biphenylyl)amine. The molecular weight of Compound 10 measured by FAB-MS was 738. In addition, the chemical shift values (δ) of Compound 10 measured by $^1$H-NMR (CDCl$_3$) were 8.09 (d, 2H, J=7.10 Hz), 7.96 (d, 1H, J=8.10 Hz) 7.89-7.85 (m, 9H), 7.80-7.74 (m, 5H), 7.73 (s, 1H), 7.71-7.66 (m, 3H), 7.48-7.21 (m, 18H).

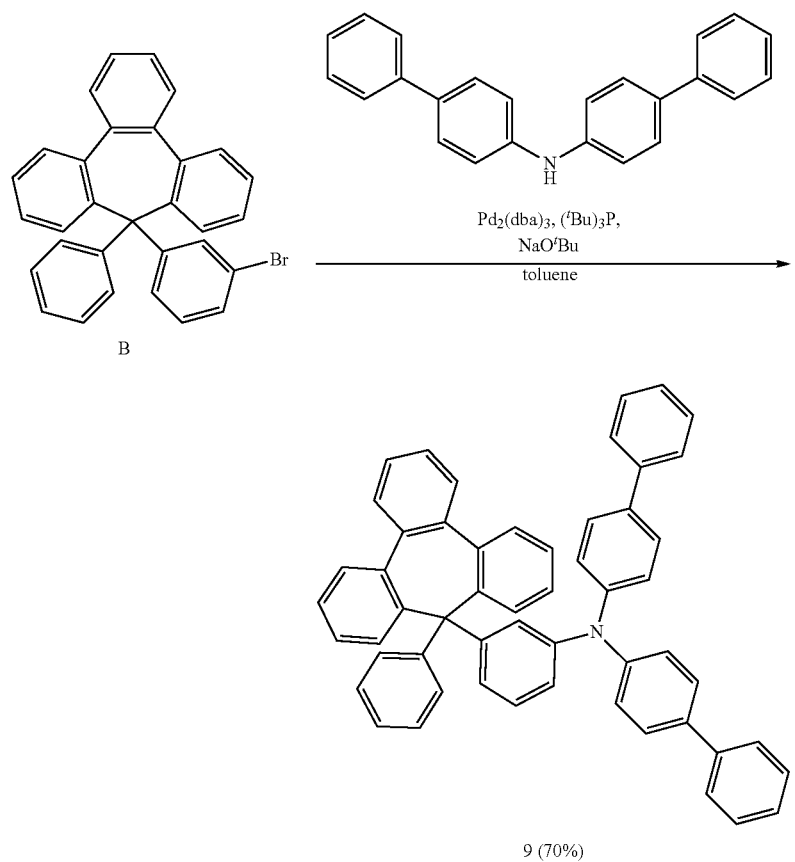

9 (70%)

3. Synthesis of Compound 28

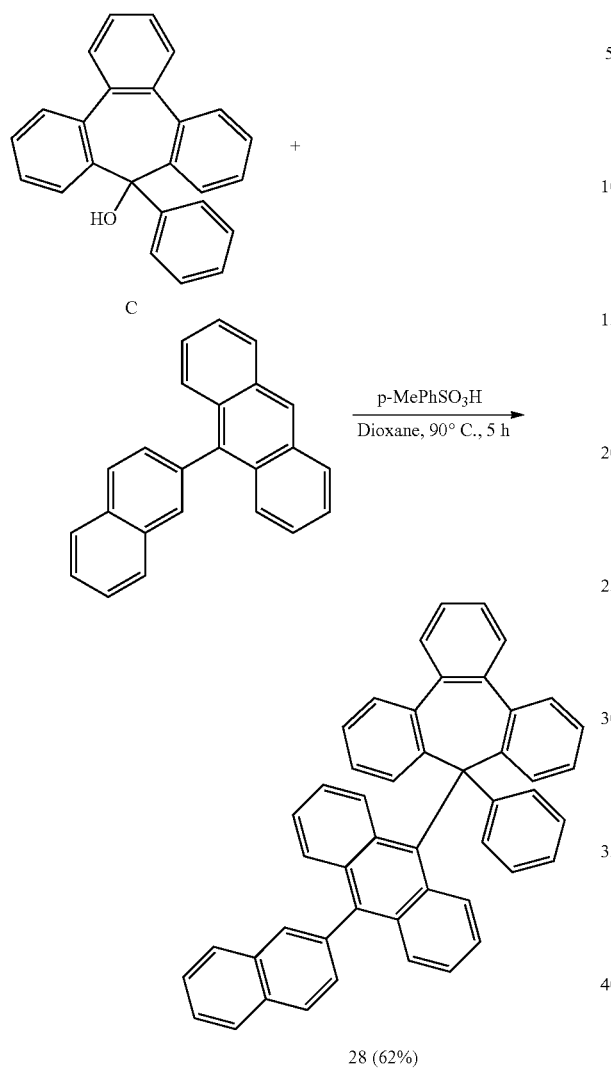

Under an argon (Ar) atmosphere, 3.41 g of Compound C, 3.05 g of 9-(2-naphthalenyl)-anthracene, 0.51 g of p-MePhSO₃H, and 45 mL of dioxane were added to a 100 mL, three-necked flask, followed by stirring the resulting mixture at about 90° C. for about 5 hours. After air-cooling the obtained product, an NaHCO₃ aqueous solution was added thereto in order to adjust the pH to 7. An organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 3.85 g (yield 62%) of Compound 28 as a white solid. The molecular weight of Compound 28 measured by FAB-MS was 621. In addition, the chemical shift values (δ) of Compound 28 measured by ¹H-NMR (CDCl₃) were 8.22-8.10 (m, 9H), 8.02 (d, 2H, J=7.20 Hz) 7.95 (d, 1H, J=8.10 Hz), 7.92 (s, 1H), 7.89-7.82 (m, 9H), 7.80-7.74 (m, 10H).

4. Synthesis of Compound 30

Compound 30 was synthesized by the same (or substantially the same) method as the synthesis of Compound 28 except for using 6-phenyl-chrysene instead of 9-(2-naphthalenyl)-anthracene. The molecular weight of Compound 30 measured by FAB-MS was 621. In addition, the chemical shift values (δ) of Compound 30 measured by ¹H-NMR (CDCl₃) were 8.20-8.10 (m, 9H), 8.02 (d, 2H, J=7.20 Hz) 7.90 (d, 1H, J=8.10 Hz), 7.87 (s, 1H), 7.82-7.77 (m, 10H), 7.70-7.54 (m, 9H).

5. Synthesis of Compound 36

Compound 36 was synthesized by the same (or substantially the same) method as the synthesis of Compound 28 except for using N,N-diphenyl-9-anthracenamine instead of 9-(2-naphthalenyl)-anthracene. The molecular weight of Compound 36 measured by FAB-MS was 662. In addition, the chemical shift values (δ) of Compound 36 measured by ¹H-NMR (CDCl₃) were 8.32 (s, 1H), 8.22-8.10 (m, 9H), 8.02 (d, 2H, J=7.20 Hz), 7.95 (d, 1H, J=8.10 Hz), 7.93 (d, 2H, J=8.10 Hz), 7.92 (s, 1H) 7.89-7.82 (m, 9H), 7.80-7.74 (m, 10H).

6. Synthesis of Compound 67

Synthesis of Compound D

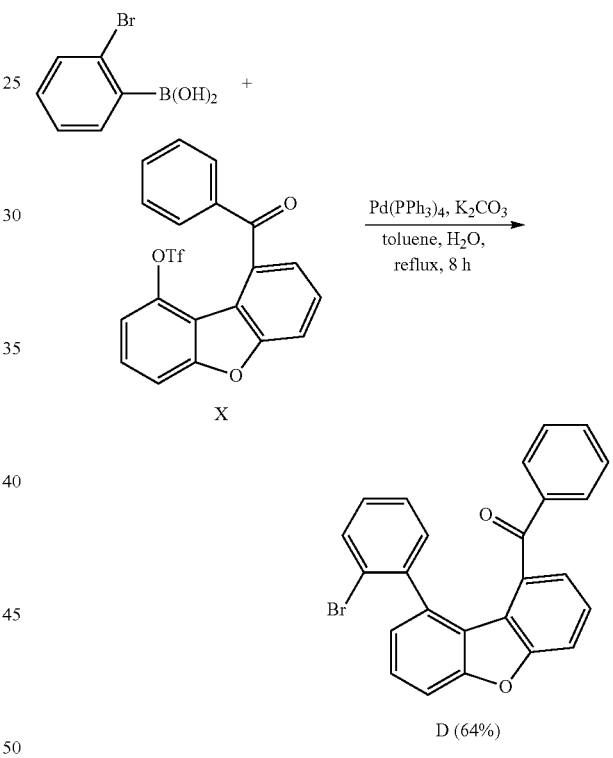

Under an argon (Ar) atmosphere, 2.00 g of 2-bromoboronic acid, 4.20 g of Compound X, 0.263 g of tetrakis (triphenylphosphine)palladium(0) (Pd(PPh₃)₄), and 3.86 g of potassium carbonate (K₂CO₃) were added to a 200 mL, three-necked flask, followed by heating, refluxing and stirring the resulting mixture in a mixture solvent of 50 mL of toluene and 20 mL of water for about 8 hours. After air-cooling the obtained product, water was added thereto, an organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 2.73 g (yield 64%) of Compound D as a white solid.

The molecular weight of Compound D measured by FAB-MS was 427.

(Synthesis of Compound E)

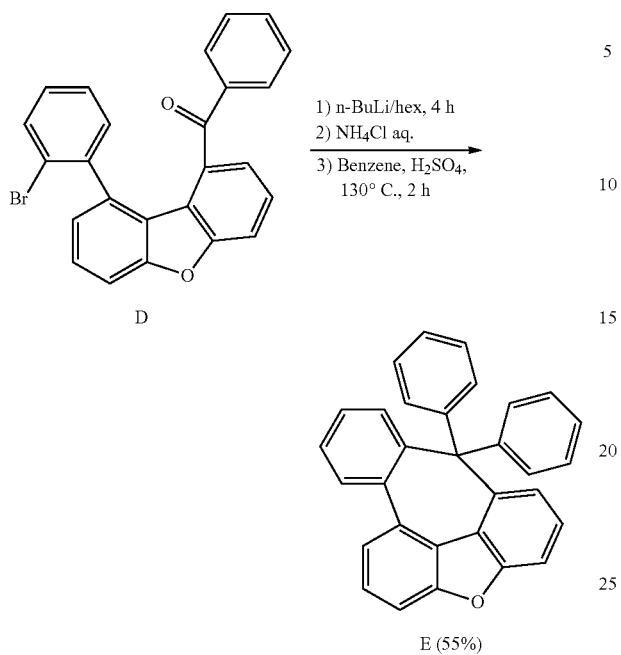

70 mL of a dehydrated THF solution of 4.27 g of Compound D was added to a 500 mL, three-necked flask, followed by stirring the resulting mixture at about −78° C. 6.75 mL of a hexane solution of 1.58 M of n-BuLi was added thereto dropwisely, followed by stirring for about 2.5 hours. Then, the reaction mixture was stirred at room temperature for about 3 hours. After finishing the reaction, a saturated NH$_4$Cl aqueous solution was added thereto, followed by stirring for about 1 hour. The reaction product was washed with water. An organic phase was concentrated to obtain a white solid. To a 500 mL, NAS-type flask, the syrup-like material thus obtained, 100 mL of benzene and 2.4 mL of sulfuric acid were added, and the resulting mixture was heated and stirred at about 130° C. for about 2 hours under a nitrogen atmosphere. After finishing the reaction, the reaction mixtures was added to 350 mL of water cooled with ice dropwisely. After white crystal precipitate was formed, the solid thus obtained was removed by filtering, and the filtrate was washed with methanol and dried. 2.24 g (yield 55%) of Compound E was obtained as a white powder.

The molecular weight of Compound E measured by FAB-MS was 408.

Synthesis of Compound F

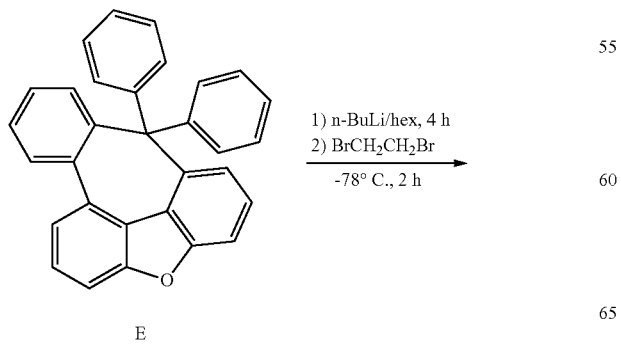

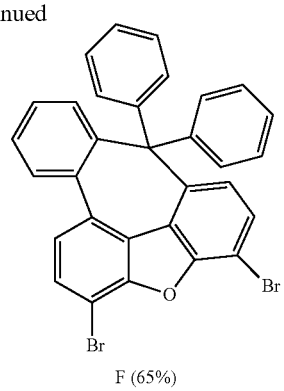

70 mL of a dehydrated THF solution with 4.08 g of Compound E was added to a 500 mL, three-necked flask, followed by stirring the resulting mixture at about −78° C. 6.98 mL of a hexane solution of 1.58 M of n-BuLi was added thereto dropwise, followed by stirring for about 2.5 hours. 85 mL of a dehydrated THF solution with 1.20 g of 1,2-dibromoethane was added thereto dropwise, followed by stirring the resulting mixture for about 2 hours and stirring at room temperature for about 3 hours. After finishing the reaction, 1 N of an aqueous hydrochloric solution was added to the mixture thus obtained and stirred for about 1 hour. The mixture thus obtained was washed with water, and an organic phase thus obtained was concentrated to obtain a white solid. The solid thus obtained was filtered, and the filtrate was washed with ethanol (EtOH)/hexane, and dried. 3.68 g (yield 65%) of Compound F was obtained as a white powder.

The molecular weight of Compound F measured by FAB-MS was 566.

Synthesis of Compound 67

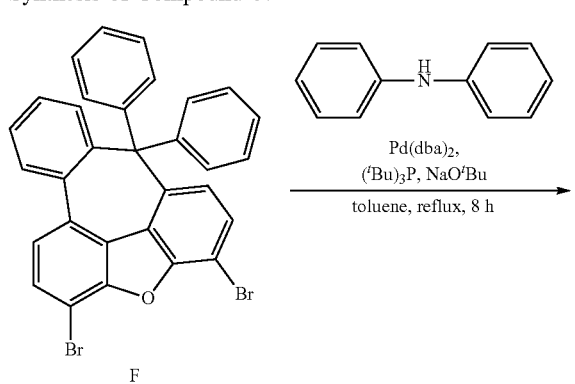

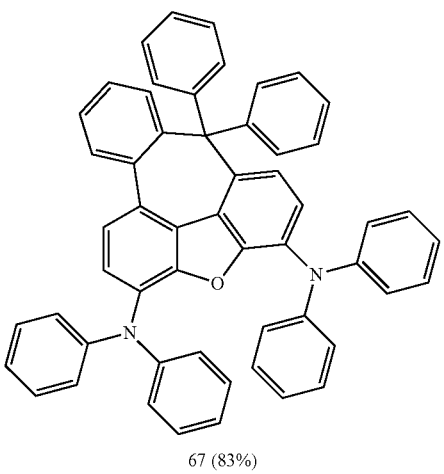

Under an argon (Ar) atmosphere, 5.66 g of Compound F, 3.40 g of diphenylamine, 0.11 g of bis(dibenzylideneacetone)palladium(0) (Pd(dba)₂), and 4.11 g of sodium tert-butoxide (NaOt-Bu) were added to a 200 mL, three-necked flask, followed by heating, refluxing and stirring the resulting mixture in 70 mL of a toluene solvent for about 8 hours. After cooling the obtained product, water was added thereto, an organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 6.17 g (yield 83%) of Compound 67 as a white solid.

The molecular weight of Compound 67 measured by FAB-MS was 743.

7. Synthesis of Compound 110
(Synthesis of Compound G)

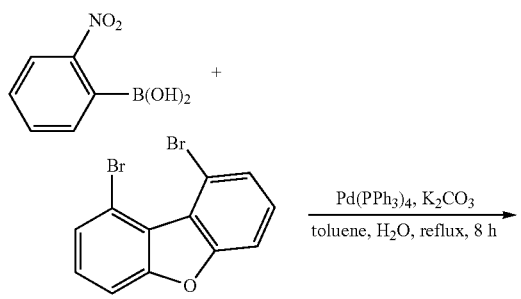

Under an argon (Ar) atmosphere, 1.67 g of 2-nitrophenylboronic acid, 3.26 g of 1,8-dibromodibenzofuran, 0.263 g of tetrakis(triphenylphosphine)palladium(0) (Pd(PPh₃)₄), and 3.86 g of potassium carbonate (K₂CO₃) were added to a 200 mL, three-necked flask, followed by heating, refluxing and stirring the resulting mixture in a mixture solvent of 50 mL of toluene and 20 mL of water for about 8 hours. After air-cooling the obtained product, water was added thereto, an organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 3.24 g (yield 88%) of Compound G as a white solid.

The molecular weight of Compound G measured by FAB-MS was 368.

Synthesis of Compound H

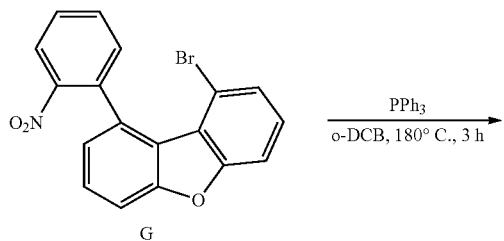

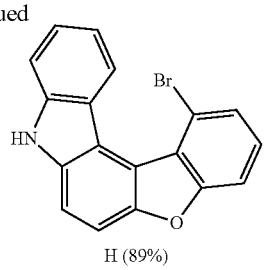

Under an argon (Ar) atmosphere, 1.84 g of Compound G, and 2.51 g of PPh₃ were added to a 200 mL, three-necked flask, followed by heating and stirring the resulting mixture in 80 mL of an o-DCB solvent at about 180° C. for about 3 hours. After air-cooling the obtained product, water was added thereto, an organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 1.50 g (yield 89%) of Compound H as a white solid.

The molecular weight of Compound H measured by FAB-MS was 336.

Synthesis of Compound I

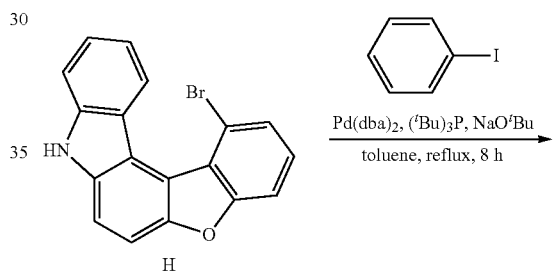

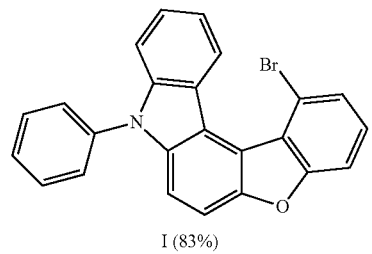

Under an argon (Ar) atmosphere, 3.36 g of Compound H, 1.00 g of iodobenzene, 0.243 g of bis(dibenzylideneacetone)palladium(0) (Pd(dba)₂), 0.13 g of (t-Bu)₃P, and 2.13 g of sodium tert-butoxide (NaOt-Bu) were added to a 200 mL, three-necked flask, followed by heating, refluxing and stirring the resulting mixture in 70 mL of a toluene solvent for about 8 hours. After air-cooling the obtained product, water was added thereto, an organic layer was separated therefrom, and solvents were distilled. The crude product thus obtained was separated by silica gel column chromatography (using a mixture solvent of toluene and hexane), and then, recrystallized using a mixture solvent of toluene and hexane to obtain 3.42 g (yield 83%) of Compound I as a white solid.

The molecular weight of Compound H measured by FAB-MS was 412.

Synthesis of Compound 110

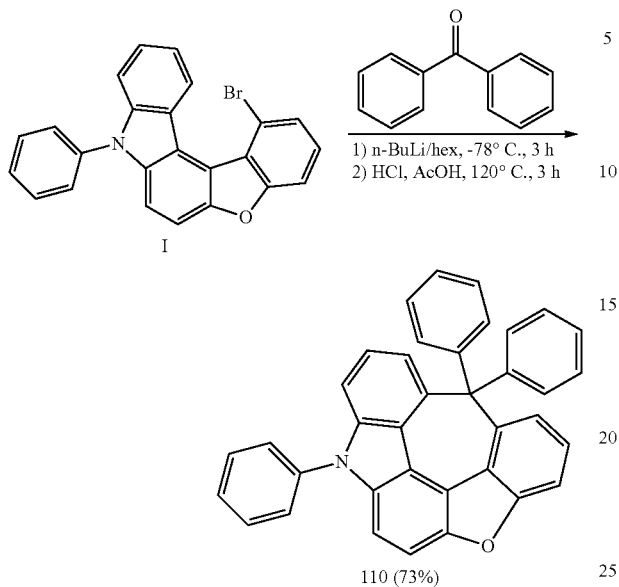

In a 300 mL, three-necked flask, 30 mL of a dehydrated THF solution of 4.12 g of Compound I was stirred at about −78° C. 6.3 mL of a hexane solution of 1.58 M of n-BuLi was added thereto dropwise and stirred for about 2.5 hours. 45 mL of a dehydrated THF solution of 1.60 g of benzophenone was added thereto dropwise, followed by stirring for about 2 hours and stirring at room temperature for about 3 hours. After finishing the reaction, 1 N hydrochloric acid aqueous solution was added to the mixture and stirred for about 1 hour. The reaction product thus obtained was washed with water, and the organic phase thus obtained was concentrated to obtain a viscous solid. To a 300 mL flask, the viscous solid, 30 mL of glacial acetic acid, and 1.4 mL of hydrochloric acid were added, followed by heating and stirring the resulting mixture for reaction at about 130° C. for about 2 hours under a nitrogen atmosphere. After finishing the reaction, the obtained reaction mixture was added to 150 mL of water cooled with ice dropwisely. After white crystal precipitate was formed, the solid was removed and the filtrate was washed with methanol and dried. At last, 3.64 g (yield 73%) of Compound 110 was obtained as a white powder.

The molecular weight of Compound 110 measured by FAB-MS was 498.

8. Synthesis of Compound 111

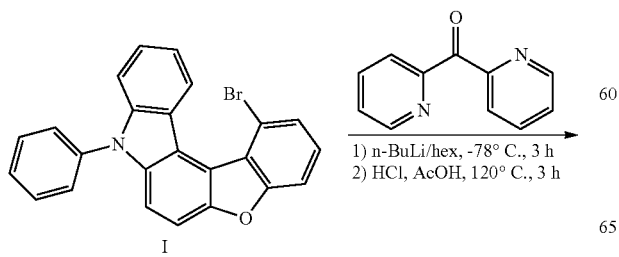

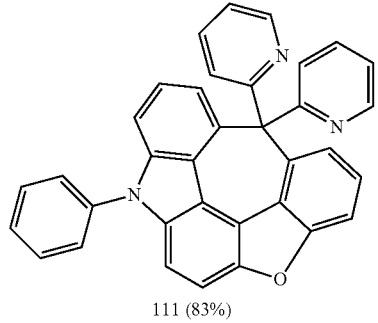

In a 300 mL, three-necked flask, 30 mL of a dehydrated THF solution of 4.12 g of Compound I was stirred at about −78° C. 6.3 mL of a hexane solution of 1.58 M of n-BuLi was added thereto dropwise and stirred for about 2.5 hours. 45 mL of a dehydrated THF solution of 1.64 g of di-2-pyridinyl-methanone was added thereto dropwise, followed by stirring for about 2 hours and then stirring again at room temperature for about 3 hours. After finishing the reaction, 1 N of hydrochloric acid aqueous solution was added to the mixture and stirred for about 1 hour. The reaction product thus obtained was washed with water, and the organic phase thus obtained was concentrated to obtain a viscous solid. To a 300 mL flask, the viscous solid, 30 mL of glacial acetic acid, and 1.4 mL of hydrochloric acid were added, followed by heating and stirring the resulting mixture for reaction at about 130° C. for about 2 hours under a nitrogen atmosphere. After finishing the reaction, the obtained reaction mixture was added to 150 mL of water cooled with ice dropwisely. After white crystal precipitate was formed, the solid thus obtained was removed and the filtrate was washed with methanol and dried. At last, 4.15 g (yield 83%) of Compound 111 was obtained as a white powder.

The molecular weight of Compound 111 measured by FAB-MS was 500.

EXPERIMENTAL EXAMPLES

1. Experimental Example 1

Organic electroluminescence devices of Examples 1 and 2 were manufactured respectively using Compounds 9 and 10 as hole transport materials.

Example Compounds

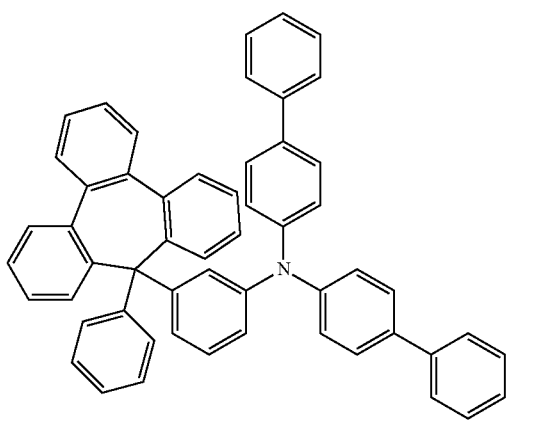

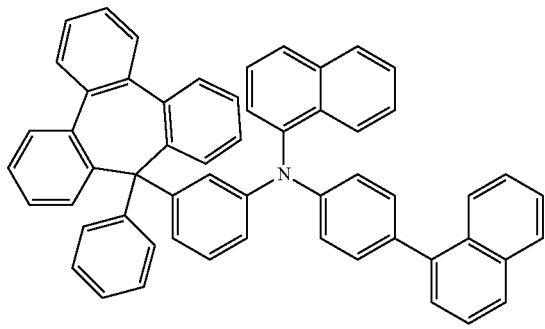

Organic electroluminescence devices of Comparative Examples 1 and 2 were manufactured respectively using Comparative Compounds X-1 and X-2 as hole transport materials.

Comparative Compounds

X-1

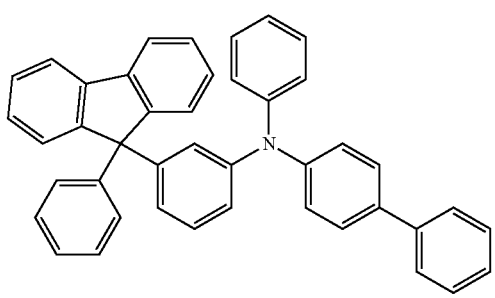

X-2

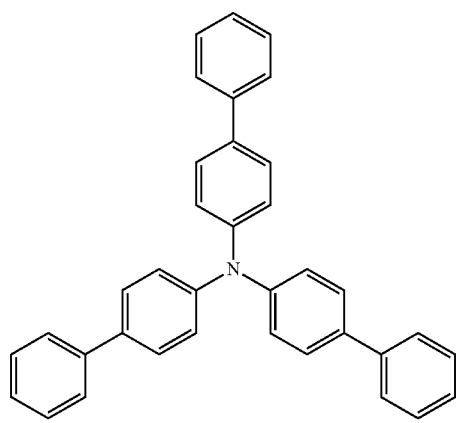

The organic electroluminescence devices of Examples 1 and 2 and Comparative Examples 1 and 2 were manufactured as follows. A first electrode having a thickness of about 150 nm was formed using ITO, a hole injection layer having a thickness of about 60 nm was formed using TNATA, a hole transport layer having a thickness of about 30 nm was formed using corresponding Example Compound or Comparative Compound, an emission layer having a thickness of about 25 nm was formed using ADN doped with 3% TBP, an electron transport layer having a thickness of about 25 nm was formed using Alq3, an electron injection layer having a thickness of about 1 nm was formed using LiF, and a second electrode having a thickness of about 100 nm was formed using Al. Each layer was formed by a deposition method in vacuum.

Then, the driving voltage, emission efficiency and half life of the organic electroluminescence devices thus manufactured were evaluated. The evaluation results are shown in the following Table 1. The driving voltage and emission efficiency in each of the examples and comparative examples are measured values at a current density of about 10 mA/cm$^2$. In addition, the half life is measured with respect to an initial luminance of about 1,000 cd/m$^2$.

The measurement was conducted using a source meter of 2400 series of Keithley Instruments, a CS-200 luminance colorimeter (Konica Minolta Holdings Co., Ltd., measurement angle 1°), and PC program LabVIEW8.2 for measurement (National Instruments Co., Ltd. in Japan) in a dark room.

TABLE 1

| | Hole transport layer | Driving voltage (V) | Emission efficiency (cd/A) | Half Life LT50 (h) |
| --- | --- | --- | --- | --- |
| Example 1 | Example Compound 9 | 5.4 | 6.5 | 2,100 |
| Example 2 | Example Compound 10 | 5.5 | 6.5 | 2,050 |
| Comparative Example 1 | Comparative Compound X-1 | 6.3 | 5.2 | 1,500 |
| Comparative Example 2 | Comparative Compound X-2 | 6.5 | 5.0 | 1,450 |

Referring to the results shown in Table 1, it is found that the organic electroluminescence devices of Examples 1 and 2 have increased life and efficiency when compared to those of Comparative Examples 1 and 2. Each of Example Compound 9 used in Example 1 and Example Compound 10 used in Example 2 has a structure including a tribenzocycloheptene moiety and an amine, and the good hole transport property of the amine may be maintained and the life of the device may be increased at the same time, due to the high charge tolerance of the tribenzocycloheptene. In addition, due to the large volume of the tribenzocycloheptene, the molecular symmetry may be collapsed, the amorphous property may be improved, and high device efficiency may be attained. In contrast, Comparative Compound X-1 used in Comparative Example 1 has a structure including a fluorenyl moiety and an amine. Since the volume of the fluorenyl is insufficient, crystallinity may be high and amorphous property may be insufficient. Thus, low efficiency and short life may result. Comparative Compound X-2 used in Comparative Example 2 has high degree of planarity of an entire molecule, high crystallinity, and insufficient amorphous property. Thus, low efficiency and short life may be attained.

2. Experimental Example 2

Organic electroluminescence devices of Examples 3 to 5 were manufactured respectively using Compounds 28, 30 and 36 as the host materials in an emission layer.

Example Compounds

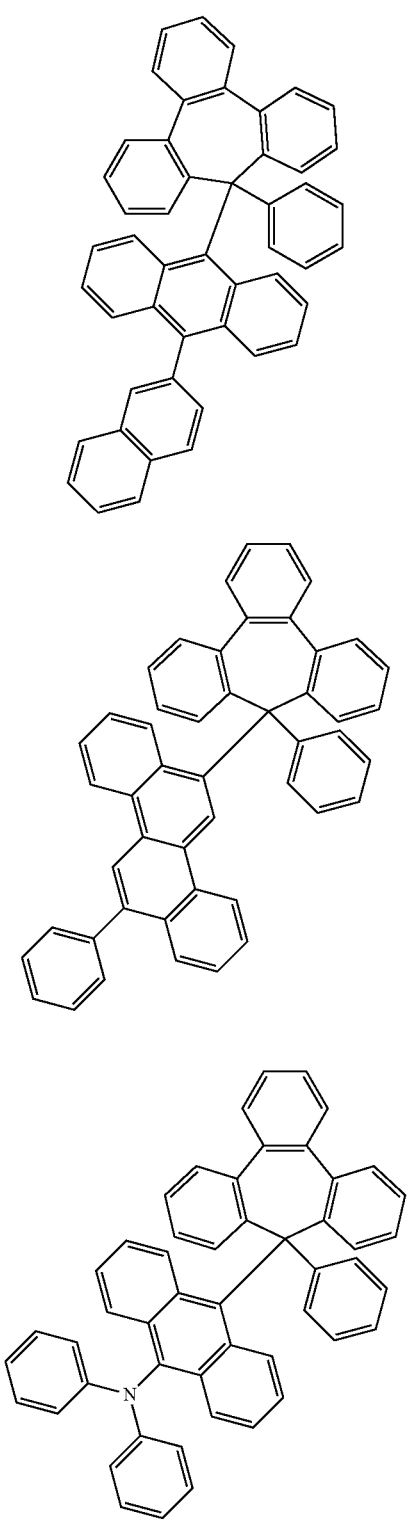

Organic electroluminescence devices of Comparative Examples 3 and 4 were manufactured respectively using the following Comparative Compounds X-3 and X-4 as the host materials in an emission layer.

Comparative Compounds

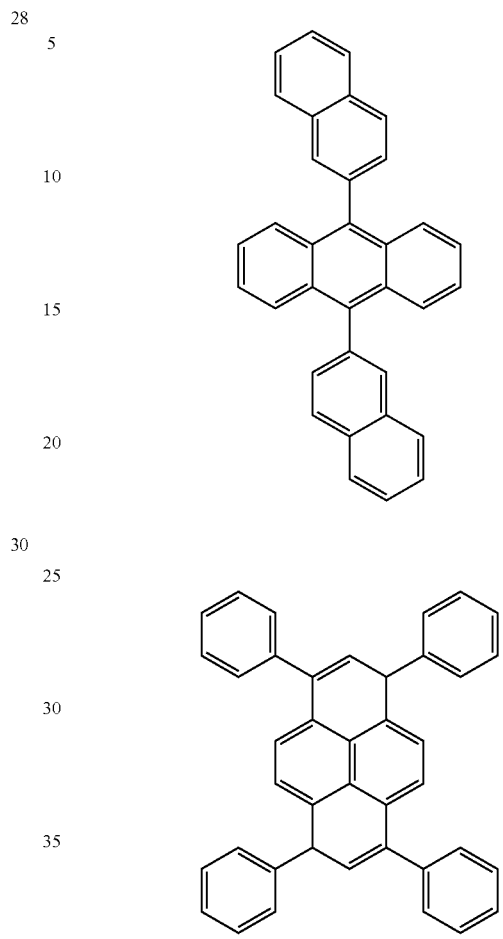

The organic electroluminescence devices of Examples 3 to 5 and Comparative Examples 3 and 4 were manufactured as follows. A first electrode having a thickness of about 150 nm was formed using ITO, a hole injection layer having a thickness of about 60 nm was formed using TNATA, a hole transport layer having a thickness of about 30 nm was formed using α-NPD, an emission layer having a thickness of about 25 nm and doped with 3% TBP was formed using corresponding Example Compound or Comparative Compound, an electron transport layer having a thickness of about 25 nm was formed using Alq3, an electron injection layer having a thickness of about 1 nm was formed using LiF, and a second electrode having a thickness of about 100 nm was formed using Al. Each layer was formed by a deposition method in vacuum.

Then, the driving voltage, emission efficiency and half life of the organic electroluminescence devices thus manufactured were evaluated. The evaluation results are shown in the following Table 2. The driving voltage and emission efficiency in each of the examples and comparative examples are measured values at a current density of about 10 mA/cm$^2$. In addition, the half life is measured with respect to an initial luminance of about 1,000 cd/m$^2$.

The measurement was conducted using a source meter of 2400 series of Keithley Instruments, a CS-200 luminance colorimeter (Konica Minolta Holdings Co., Ltd., measurement angle 1°), and PC program LabVIEW8.2 for measurement (National Instruments Co., Ltd. in Japan) in a dark room.

TABLE 2

|  | Host material in emission layer | Driving voltage (V) | Emission efficiency (cd/A) | Half Life LT50 (h) |
|---|---|---|---|---|
| Example 3 | Example Compound 28 | 5.7 | 6.2 | 2,000 |
| Example 4 | Example Compound 30 | 5.6 | 6.3 | 2,050 |
| Example 5 | Example Compound 36 | 5.7 | 6.2 | 1,950 |
| Comparative Example 3 | Comparative Compound X-3 | 6.5 | 5.2 | 1,600 |
| Comparative Example 4 | Comparative Compound X-4 | 6.6 | 4.8 | 1,650 |

Referring to the results shown in Table 2, it is found that the organic electroluminescence devices of Examples 3 to 5 have increased life and efficiency when compared to those of Comparative Examples 3 and 4. Each of Example Compound 28 used in Example 3, Example Compound 30 used in Example 4, and Example Compound 36 used in Example 5 has a structure including a tribenzocycloheptene moiety coupled to an aryl group having a three- or four-membered ring, and the good hole transport property of a polycyclic aryl group may be maintained and the life of the device may be increased at the same time, due to the high charge tolerance of the tribenzocycloheptene. In addition, due to the large volume of the tribenzocycloheptene, the molecular symmetry may be collapsed, the amorphous property may be improved, and high device efficiency may be attained. In contrast, Comparative Compound X-3 used in Comparative Example 3 has a structure in which naphthalene is substituted at positions 9 and 10 of anthracene, and the compound has high planarity and symmetric properties. Accordingly, crystallinity may be high, amorphous property may be insufficient, and low efficiency and short life may result. Since Comparative Compound X-4 used in Comparative Example 4 also has a molecular structure with high planarity and symmetric properties, high crystallinity, and insufficient amorphous property, low efficiency and short life may similarly result.

From the results shown in Tables 1 and 2, it can be found that efficiency and life of the organic electroluminescence device may be increased by using the polycyclic compound according to an embodiment of the inventive concept.

3. Experimental Example 3

Organic electroluminescence devices of Examples 6 and 7 were manufactured respectively using Compounds 67 and 110 as hole transport materials.

Example Compounds

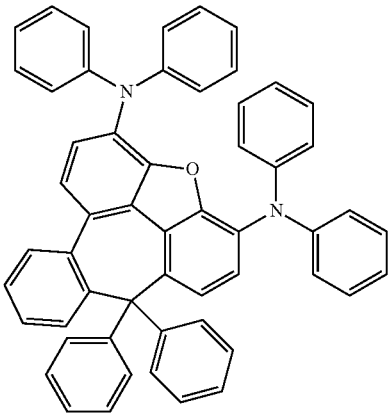

67

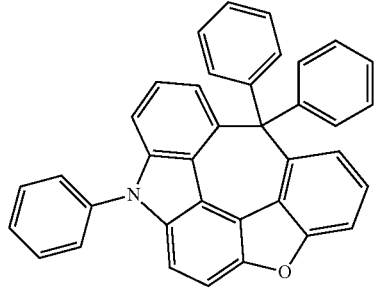

110

Organic electroluminescence devices of Comparative Examples 5 and 6 were manufactured respectively using Comparative Compounds X-5 and X-6 as hole transport materials.

Comparative Compounds

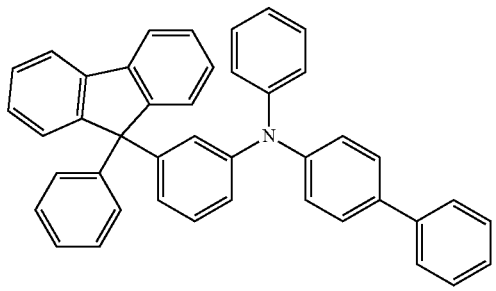

X-5

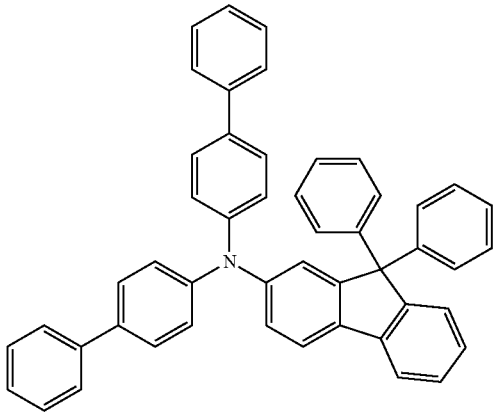

X-6

The organic electroluminescence devices of Examples 6 and 7 and Comparative Examples 5 and 6 were manufactured as follows. A first electrode having a thickness of about 150 nm was formed using ITO, a hole injection layer having a thickness of about 60 nm was formed using TNATA, a hole transport layer having a thickness of about 30 nm was formed using corresponding Example Compound or Comparative Compound, an emission layer having a thickness of about 25 nm was formed using ADN doped with 3% TBP, an electron transport layer having a thickness of about 25 nm was formed using Alq3, an electron injection layer having a thickness of about 1 nm was formed using LiF, and a second electrode having a thickness of about 100 nm was formed using Al. Each layer was formed by a deposition method in vacuum.

Then, the driving voltage, emission efficiency and half life of the organic electroluminescence devices thus manufactured were evaluated. The evaluation results are shown in the following Table 3. The driving voltage and emission efficiency in each of the examples and comparative examples are measured values at a current density of about 10 mA/cm². In addition, the half life is measured with respect to an initial luminance of about 1,000 cd/m².

The measurement was conducted using a source meter of 2400 series of Keithley Instruments, a CS-200 luminance colorimeter (Konica Minolta Holdings Co., Ltd., measurement angle 1°), and PC program LabVIEW8.2 for measurement (National Instruments Co., Ltd. in Japan) in a dark room.

TABLE 3

| | Hole transport layer | Driving voltage (V) | Emission efficiency (cd/A) | Half Life LT50 (h) |
|---|---|---|---|---|
| Example 6 | Example Compound 67 | 5.4 | 6.5 | 2,100 |
| Example 7 | Example Compound 110 | 5.5 | 6.5 | 2,050 |
| Comparative Example 5 | Comparative Compound X-5 | 6.3 | 5.2 | 1,500 |
| Comparative Example 6 | Comparative Compound X-6 | 6.5 | 5.0 | 1,550 |

Referring to the results shown in Table 3, it is found that the organic electroluminescence devices of Examples 6 and 7 have increased life and efficiency when compared to those of Comparative Examples 5 and 6. In each of Example Compound 67 used in Example 6 and Example Compound 110 used in Example 7, the good emission property of a polycyclic aryl group may be maintained and the life of the device may be increased at the same time, due to the high charge tolerance of the tribenzocycloheptene. In addition, due to the large volume of the tribenzocycloheptene, the molecular symmetry may be collapsed, the amorphous property may be improved, and high device efficiency may be attained. Since Comparative Compound X-5 used in Comparative Example 5 and Comparative Compound X-6 used in Comparative Example 6 have insufficient amorphous property, low efficiency and short life may result.

4. Experimental Example 4

An organic electroluminescence device of Example 8 was manufactured using Compound 111 as the host material in an emission layer.

Example Compound

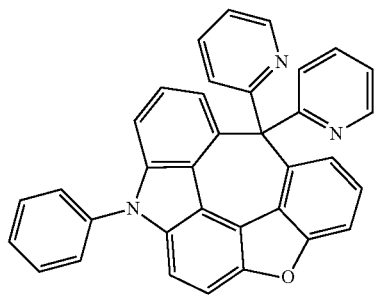

111

Organic electroluminescence devices of Comparative Examples 7 and 8 were manufactured respectively using Comparative Compounds X-7 and X-8 as the host materials in an emission layer.
Comparative Compounds

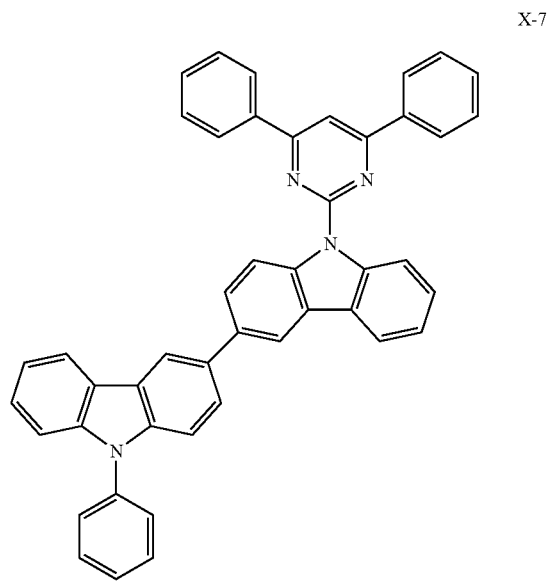

X-7

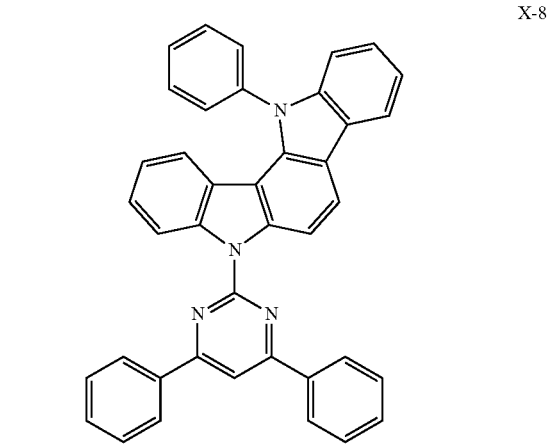

X-8

The organic electroluminescence devices of Example 8 and Comparative Examples 7 and 8 were manufactured as follows. A first electrode having a thickness of about 150 nm was formed using ITO, a hole injection layer having a thickness of about 60 nm was formed using TNATA, a hole transport layer having a thickness of about 30 nm was formed using 4,4'-bis(N,N'-(3-tolyl)amino)-3,3'-dimethylbiphenyl, an emission layer having a thickness of about 25 nm and doped with 20% Ir(ppy)$_3$ was formed using corresponding Example Compound or Comparative Example Compound, an electron transport layer having a thickness of about 25 nm was formed using Alq3, an electron injection layer having a thickness of about 1 nm was formed using LiF, and a second electrode having a thickness of about 100 nm was formed using Al. Each layer was formed by a deposition method in vacuum.

Then, the driving voltage, emission efficiency and half life of the organic electroluminescence devices thus manufactured were evaluated. The evaluation results are shown in the following Table 4. The driving voltage and emission efficiency in each of the examples and comparative examples are measured values at a current density of about 10 mA/cm$^2$. In addition, the half life is measured with respect to an initial luminance of about 1,000 cd/m$^2$.

The measurement was conducted using a source meter of 2400 series of Keithley Instruments, a CS-200 luminance colorimeter (Konica Minolta Holdings Co., Ltd., measurement angle 1°), and PC program LabVIEW8.2 for measurement (National Instruments Co., Ltd. in Japan) in a dark room.

TABLE 4

| | Host material in emission layer | Driving voltage (V) | Emission efficiency (cd/A) | Half Life LT50 (h) |
|---|---|---|---|---|
| Example 8 | Example Compound 111 | 4.0 | 35.3 | 2,300 |
| Comparative Example 7 | Comparative Compound X-7 | 4.9 | 29.2 | 1,500 |
| Comparative Example 8 | Comparative Compound X-8 | 5.5 | 28.8 | 1,450 |

Referring to the results shown in Table 4, it is found that the organic electroluminescence device of Example 8 has increased life and efficiency when compared to those of Comparative Examples 7 and 8.

From the results of Tables 1 to 4, it can be found that by using the polycyclic compound represented by Formula 1 according to an embodiment of the inventive concept in an organic electroluminescence device, efficiency and life may be increased.

The polycyclic compound represented by Formula 1 according to an embodiment of the inventive concept may be synthesized, for example, as follows. However, an embodiment is not limited thereto.

Preparation Method
9. Synthesis of Compound A-3
Synthesis of Compound J

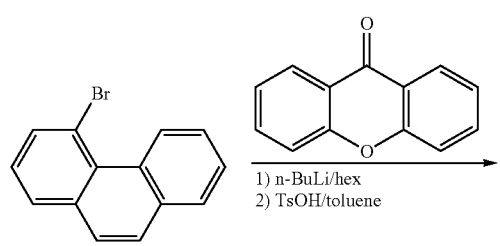

Under an argon (Ar) atmosphere, 1.3 g of 4-bromonaphthalene was dissolved in 30 mL of tetrahydrofuran (THF) in a 200 mL, three-necked flask, followed by cooling to about 0° C. 1.6 M of n-butyllithium and 3.1 mL of a hexane solution were added thereto dropwise. 30 mL of a THF solution containing 0.98 g of 9H-xanthene-9-one was added thereto, followed by stirring for about 2 hours. Water was added to the reaction product, an organic layer was separated therefrom, and solvents were distilled. To the product thus obtained, 30 mL of toluene containing 0.86 g of p-toluenesulfonic acid was added, followed by heating the resulting mixture at about 110° C. for about 1 hour. After air-cooling the obtained product, water was added to the reaction product, an organic layer was separated therefrom, and solvents were distilled. The crude product thus obtained was separated by silica gel column chromatography (toluene and hexane) to obtain 0.71 g (yield 40%) of Compound J as a white solid. The molecular weight of Compound J was measured by FAB-MS and was obtained as 356 (C$_{27}$H$_{16}$O).

Synthesis of Compound K

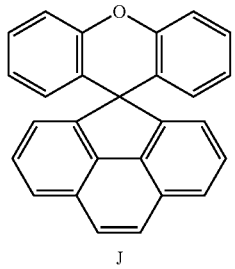

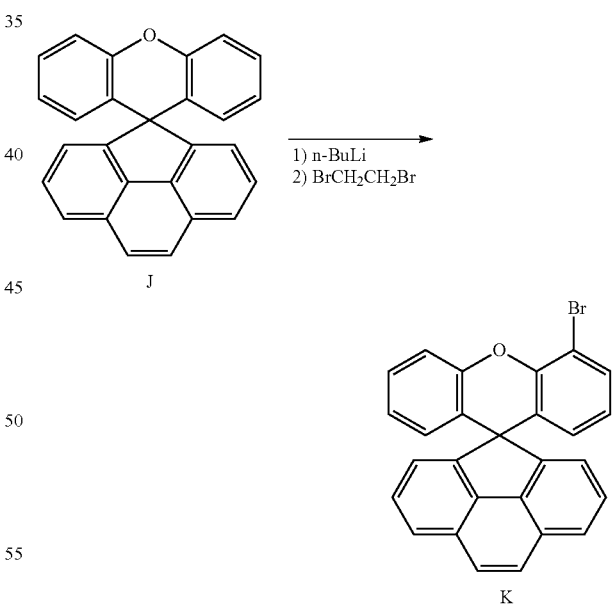

Under an argon (Ar) atmosphere, 1.78 g of Compound J was dissolved in 30 mL of THF in a 200 mL, three-necked flask, followed by cooling to about 0° C. 1.6 M of n-butyllithium and 3.1 mL of a hexane solution were added thereto dropwise. 30 mL of a THF solution containing 1.00 g of 1,2-dibromomethane was added thereto, followed by stirring the resulting mixture for about 5 hours. Water was added to the reaction product, an organic layer was separated therefrom, and solvents were distilled. The crude product thus obtained was separated by silica gel column chromatography (toluene and hexane) to obtain 1.30 g (yield 60%) of Compound K as a white solid. The molecular weight of Compound K was measured by FAB-MS and was obtained as 434 ($C_{27}H_{15}OBr$).

Synthesis of Compound A-3

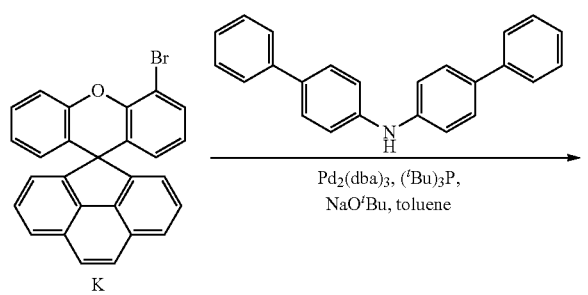

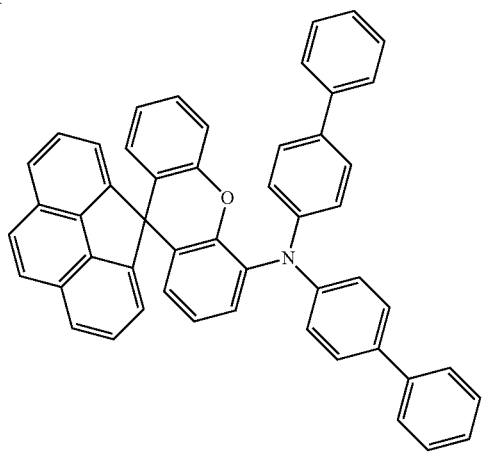

A-3

Under an argon (Ar) atmosphere, 2.18 g of Compound K, 1.61 g of bis(1,1'-biphenyl)-4-ylamine, 0.46 g of tris(dibenzylideneacetone)dipalladium(0), 0.16 g of tri-tert-butylphosphine, and 1.93 g of sodium tert-butoxide were added to a 200 mL, three-necked flask, followed by heating and refluxing the resulting mixture in 60 mL of a toluene solvent for about 7 hours. After air-cooling the obtained reaction product, water was added to the reaction product, an organic layer was separated therefrom, and solvents were distilled. The crude product thus obtained was separated by silica gel column chromatography (toluene and hexane) to obtain 2.36 g (yield 70%) of Compound A-3 as a white solid. The molecular weight of Compound A-3 was measured by FAB-MS and was obtained as 675 ($C_{51}H_{33}NO$). FAB-MS was measured using JMS-700 manufactured by JEOL Co.

10. Synthesis of Compound A-12

Synthesis of Compound L

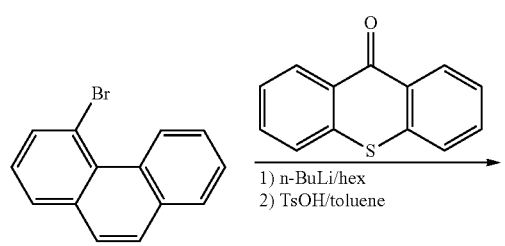

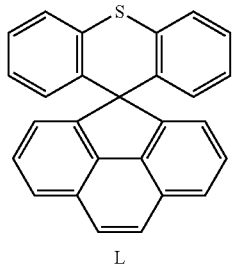

L

Under an argon (Ar) atmosphere, 1.3 g of 4-bromophenanthrene was dissolved in 30 mL of THF in a 200 mL, three-necked flask, followed by cooling the resulting mixture to about 0° C. 1.6 M of n-butyllithium and 3.1 mL of a hexane solution were added thereto dropwise. 30 mL of a THF solution containing 1.06 g of 9H-thiaxanthene-9-one was added thereto, followed by stirring for about 2 hours. Water was added to the reaction product, an organic layer was separated therefrom, and solvents were distilled. To the product thus obtained, 30 mL of toluene containing 0.86 g of p-toluenesulfonic acid was added, followed by heating the resulting mixture at about 110° C. for about 1 hour. After air-cooling the obtained reaction product, water was added to the reaction product, an organic layer was separated therefrom, and solvents were distilled. The crude product thus obtained was separated by silica gel column chromatography (toluene and hexane) to obtain 0.73 g (yield 39%) of Compound L as a white solid. The molecular weight of Compound L was measured by FAB-MS and was obtained as 372 ($C_{27}H_{16}S$). FAB-MS was measured using JMS-700 manufactured by JEOL Co.

Synthesis of Compound M

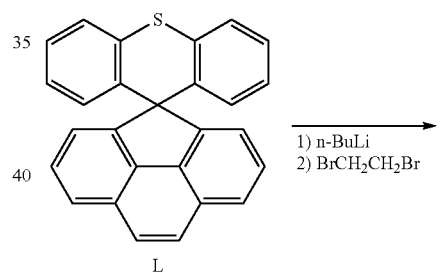

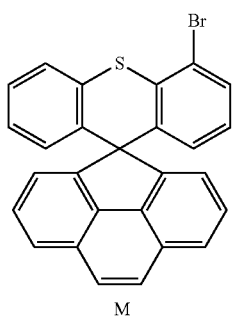

M

Under an argon (Ar) atmosphere, 1.86 g of Compound L was dissolved in 30 mL of THF in a 200 mL, three-necked flask, followed by cooling the resulting mixture to about 0° C. 1.6 M of n-butyllithium and 3.1 mL of a hexane solution were added thereto dropwise. 30 mL of a THF solution containing 1.00 g of 1,2-dibromomethane was added thereto, followed by stirring the resulting mixture for about 5 hours. Water was added to the reaction product, an organic layer was separated therefrom, and solvents were distilled. The crude product thus obtained was separated by silica gel column chromatography (toluene and hexane) to obtain 1.24 g (yield 55%) of Compound M as a white solid. The molecular weight of Compound M was measured by FAB-MS and was obtained as 450 ($C_{27}H_{15}SBr$). FAB-MS was measured using JMS-700 manufactured by JEOL Co.

Synthesis of Compound A-12

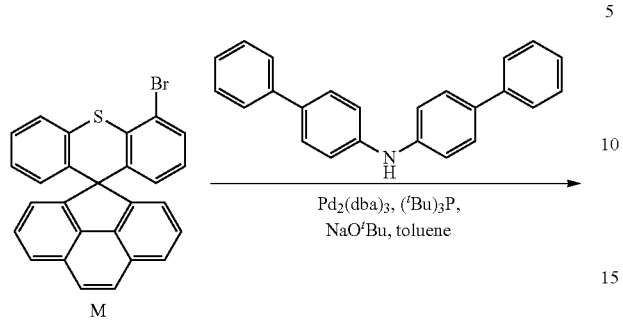

M

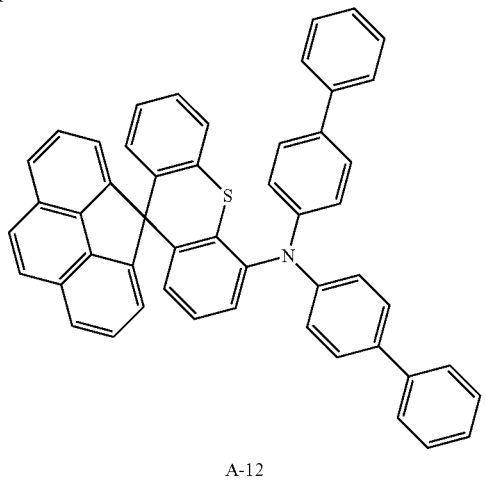

A-12

Under an argon (Ar) atmosphere, 2.26 g of Compound M, 1.61 g of bis(1,1'-biphenyl)-4-ylamine, 0.46 g of tris(dibenzylideneacetone)dipalladium(0), 0.16 g of tri-tert-butylphosphine, and 1.93 g of sodium tert-butoxide were added to a 200 mL, three-necked flask, followed by heating and refluxing the resulting mixture in 60 mL of a toluene solvent for about 7 hours. After air-cooling the obtained product, water was added to the reaction product, an organic layer was separated therefrom, and solvents were distilled. The crude product thus obtained was separated by silica gel column chromatography (toluene and hexane) to obtain 2.30 g (yield 66%) of Compound A-12 as a white solid. The molecular weight of Compound A-12 was measured by FAB-MS and was obtained as 691 ($C_{51}H_{33}NS$). FAB-MS was measured using JMS-700 manufactured by JEOL Co.

11. Synthesis of Compound A-21

Synthesis of Compound N

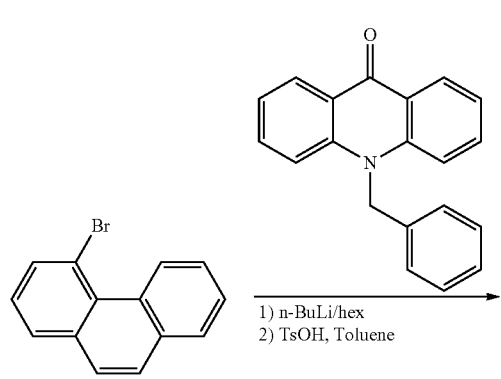

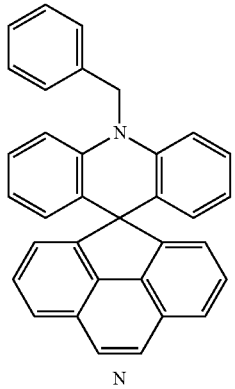

N

Under an argon (Ar) atmosphere, 1.3 g of 4-bromonaphthalene was dissolved in 30 mL of THF in a 200 mL, three-necked flask, followed by cooling the resulting mixture to about 0° C. 1.6 M of n-butyllithium and 3.1 mL of a hexane solution were added thereto dropwise. 30 mL of a THF solution containing 1.42 g of 10-benzylacridine-9 (10H)-one was added thereto, followed by stirring the resulting mixture for about 2 hours. Water was added to the reaction product, an organic layer was separated therefrom, and solvents were distilled. To the product thus obtained, 30 mL of toluene containing 0.86 g of p-toluenesulfonic acid was added, followed by heating the resulting mixture at about 110° C. for about 1 hour. After air-cooling the obtained reaction product, water was added to the reaction product, an organic layer was separated therefrom, and solvents were distilled. The crude product thus obtained was separated by silica gel column chromatography (toluene and hexane) to obtain 0.78 g (yield 35%) of Compound N as a white solid. The molecular weight of Compound N was measured by FAB-MS and was obtained as 445 ($C_{34}H_{23}N$). FAB-MS was measured using JMS-700 manufactured by JEOL Co.

Synthesis of Compound O

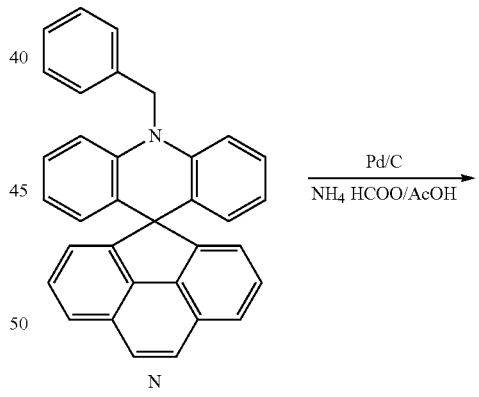

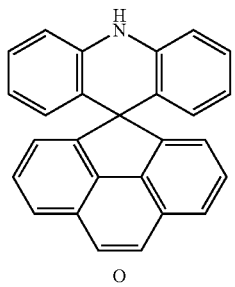

O 2.22 g of Compound N and 2.2 g of Pd/C were added to a 200 mL, three-necked flask, and 60 mL of acetic acid and 2 g of ammonium formate were added thereto, followed by refluxing the resulting mixture for about 48 hours. The reaction product was cooled in the air, filtered and washed with chloroform. Water was added to the resulting product, and 2 M of NaOH aqueous solution was added thereto for neutralization. An organic layer was separated therefrom and concentrated. The crude product thus obtained was separated by silica gel column chromatography (toluene and hexane) to obtain 1.33 g (yield 75%) of Compound O as a white solid. The molecular weight of Compound O was measured by FAB-MS and was obtained as 355 ($C_{27}H_{17}N$). FAB-MS was measured using JMS-700 manufactured by JEOL Co.

Synthesis of Compound A-21

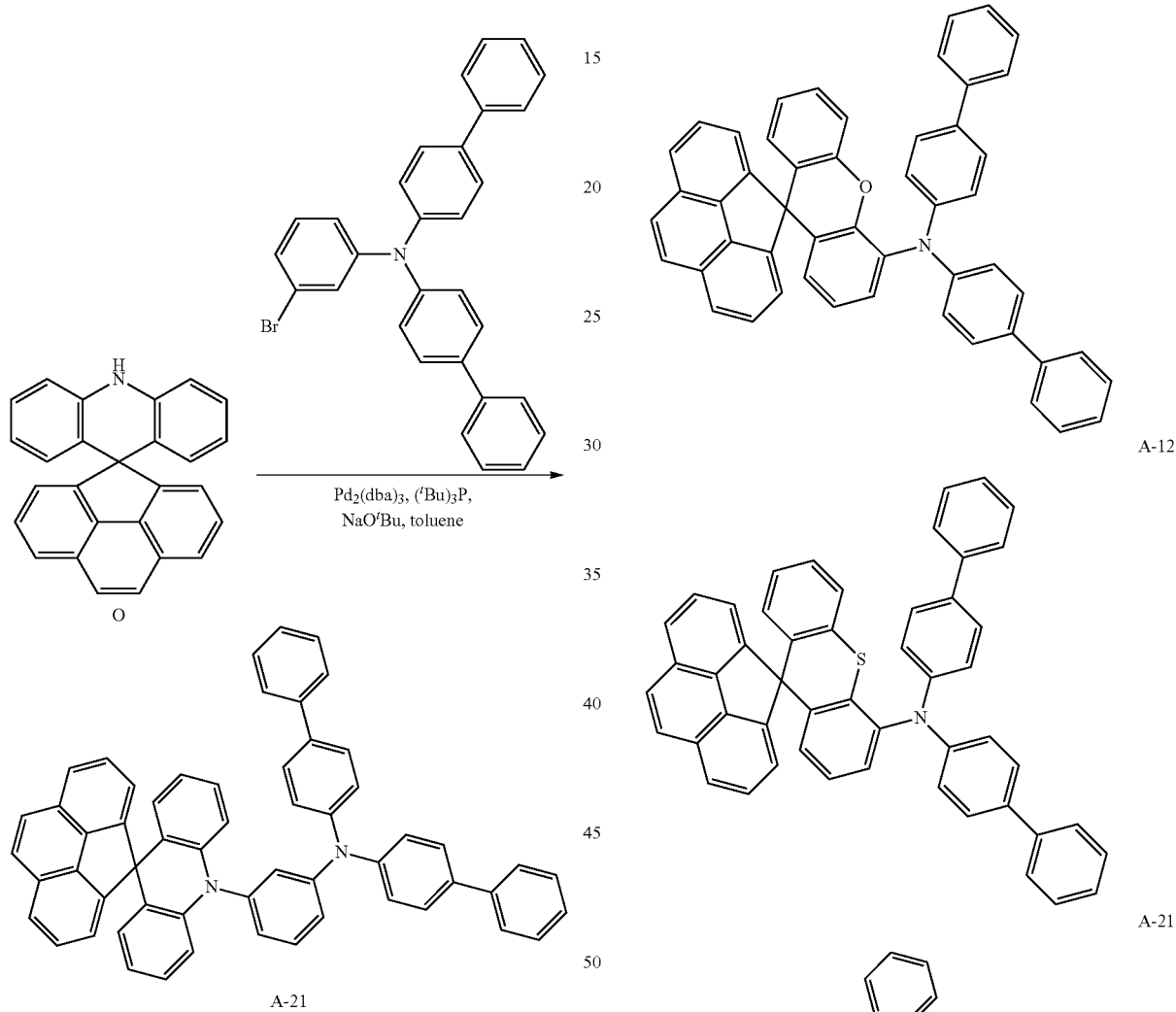

Under an argon (Ar) atmosphere, 1.78 g of Compound O, 2.34 g of N-([1,1'-biphenyl]-4-yl)-N-(3-bromophenyl)-[1,1'-biphenyl]-4-amine, 0.46 g of tris(dibenzylideneacetone)dipalladium(0), 0.16 g of tri-tert-butylphosphine, and 1.93 g of sodium tert-butoxide were added to a 200 mL, three-necked flask, followed by heating and refluxing the resulting mixture in 60 mL of a toluene solvent for about 7 hours. After air-cooling the obtained reaction product, water was added to the reaction product, an organic layer was separated therefrom, and solvents were distilled. The crude product thus obtained was separated by silica gel column chromatography (toluene and hexane) to obtain 2.82 g (yield 75%) of Compound A-21 as a white solid. The molecular weight of Compound A-21 was measured by FAB-MS and was obtained as 750 ($C_{57}H_{38}N_2$). FAB-MS was measured using JMS-700 manufactured by JEOL Co.

Experimental Example

5. Experimental Example 5

Organic electroluminescence devices of Examples 9 to 11 were manufactured respectively using Compounds A-3, A-12, and A-21 as hole transport materials.

Example Compounds

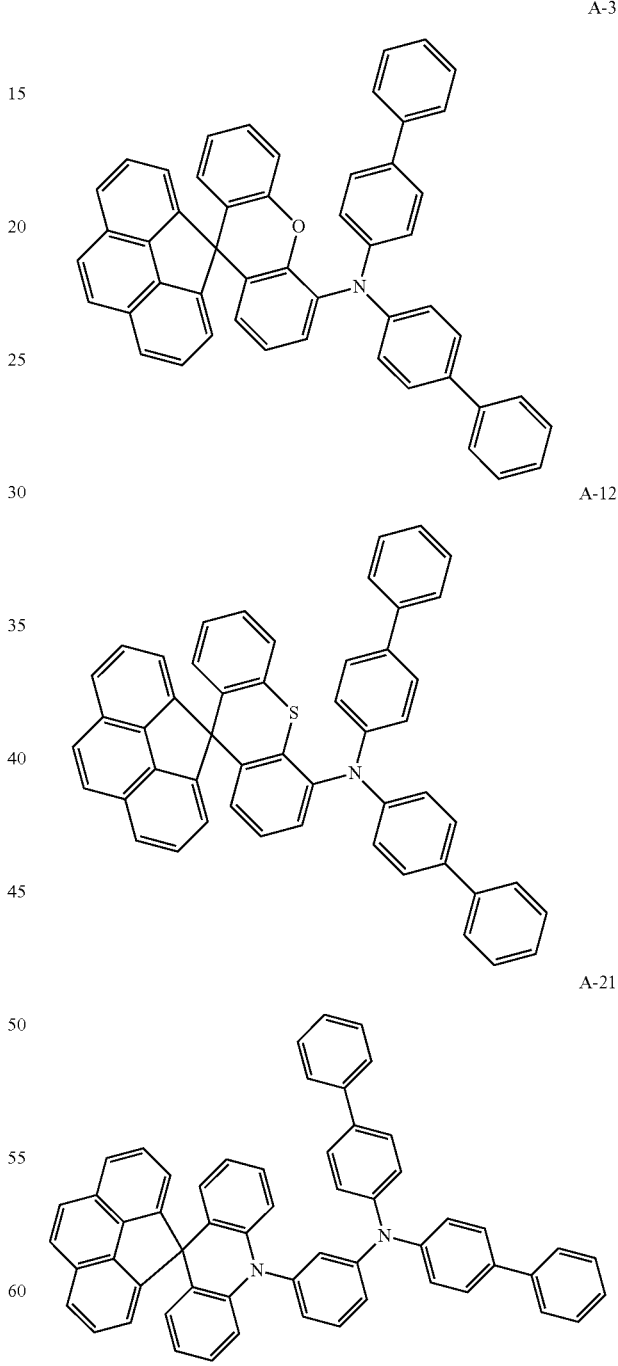

Organic electroluminescence devices of Comparative Examples 9 and 10 were manufactured respectively using Comparative Compounds X-9 and X-10 as hole transport materials.

Comparative Compounds

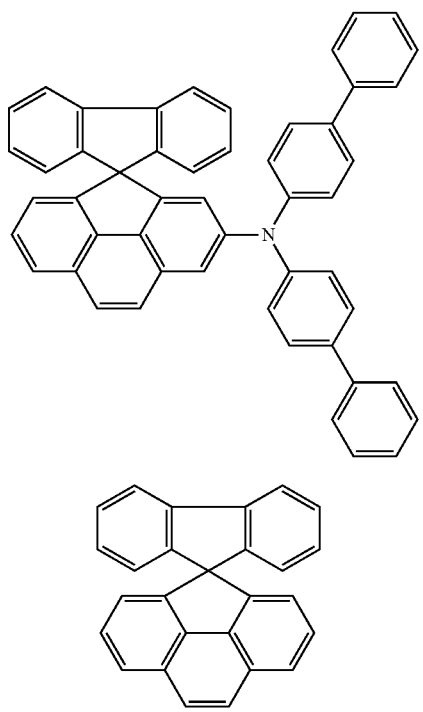

The organic electroluminescence devices of Examples 9 to 11 and Comparative Examples 9 and 10 were manufactured as follows. An anode having a thickness of about 150 nm was formed using ITO, a hole injection layer having a thickness of about 60 nm was formed using TNATA, a hole transport layer having a thickness of about 30 nm was formed using corresponding Example Compound or Comparative Compound, an emission layer having a thickness of about 25 nm was formed using ADN doped with 3% TBP, an electron transport layer having a thickness of about 25 nm was formed using Alq3, an electron injection layer having a thickness of about 1 nm was formed using LiF, and a cathode having a thickness of about 100 nm was formed using Al.

Then, the emission efficiency of the organic electroluminescence devices thus manufactured was evaluated. The evaluation results are shown in the following Table 5. The emission efficiency is a measured value at a current density of about 10 mA/cm$^2$.

The measurement was conducted using a source meter of 2400 series of Keithley Instruments, a CS-200 luminance colorimeter (Konica Minolta Holdings Co., Ltd., measurement angle 1°), and PC program LabVIEW8.2 for measurement (National Instruments Co., Ltd., in Japan).

TABLE 5

| Device manufacturing examples | Hole transport layer | Current density (mA/cm$^2$) | Emission efficiency (cd/A) |
|---|---|---|---|
| Example 9 | Example Compound A-3 | 10 | 6.6 |
| Example 10 | Example Compound A-12 | 10 | 6.5 |
| Example 11 | Example Compound A-21 | 10 | 6.4 |
| Comparative Example 9 | Comparative Compound X-9 | 10 | 5.4 |
| Comparative Example 10 | Comparative Compound X-10 | 10 | 0.4 |

Referring to the results in Table 5, it is found that the organic electroluminescence devices of Examples 9 to 11 have increased emission efficiency when compared to those of Comparative Examples 9 and 10. Each of Example Compounds A-3, A-12 and A-21 used in Examples 9 to 11 includes a heteroatom having hole transport property, and hole transport property of the device may be improved and emission efficiency may be improved when compared to Comparative Compounds X-9 and X-10 respectively used in Comparative Examples 9 and 10.

The compound according to an embodiment of the inventive concept may be used as a material for an organic electroluminescence device. The compound according to an embodiment of the inventive concept may improve the emission efficiency of an organic electroluminescence device. The compound according to an embodiment of the inventive concept may increase the life of an organic electroluminescence device.

The organic electroluminescence device according to an embodiment of the inventive concept may accomplish improved emission efficiency. The organic electroluminescence device according to an embodiment of the inventive concept may attain increased life.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present invention have been described herein, it is understood that the present invention should not be limited to these example embodiments but various changes and modifications can be made by one ordinary skilled in the art within the spirit and scope of the present invention as defined by the following claims and equivalents thereof.

What is claimed is:

1. A polycyclic compound represented by the following Formula 1, Formula 3, or Compound 41:

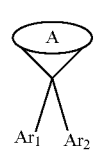

Formula 1

-continued

Formula 3

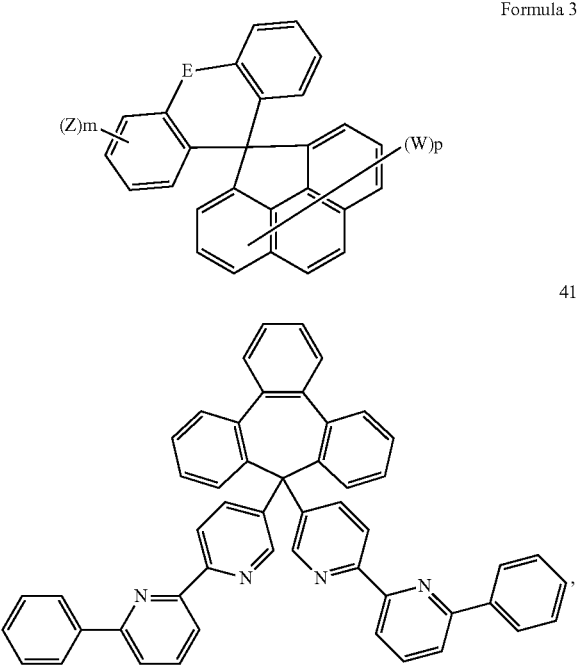

in Formula 1,
Ar₁ and Ar₂ are each independently selected from substituted or unsubstituted anthracenyl group, substituted or unsubstituted pyrenyl group, substituted or unsubstituted phenanthryl group, substituted or unsubstituted chrysenyl group, substituted or unsubstituted triphenylenyl group, and substituted or unsubstituted carbazolyl group, where Ar₁ and Ar₂ optionally combine with each other to form a ring, and
A is represented by the following Formula 2-1:

Formula 2-1

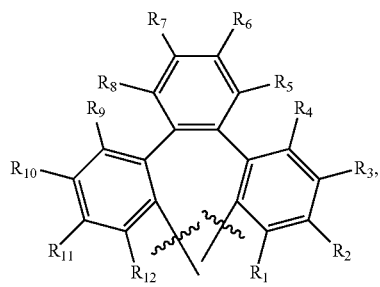

in Formula 2-1,
$R_1$ to $R_{12}$ are each independently selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, where adjacent groups optionally combine with each other to form a ring,
in Formula 3,
W is selected from hydrogen, deuterium, halogen, silyl group, substituted or unsubstituted alkyl group having 1 to 20 carbon atoms, substituted or unsubstituted aryl group having 6 to 60 carbon atoms for forming a ring, and substituted or unsubstituted heteroaryl group having 5 to 60 carbon atoms for forming a ring, and
p is an integer from 0 to 8, wherein when p is 2 or more, a plurality of W are the same as or different from each other,
E is O, S, or NR',
m is 0 or 1, and
Z and R' are each independently represented by the following Formula 4:

Formula 4

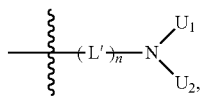

in Formula 4,
$U_1$ and $U_2$ are each independently substituted or unsubstituted aryl group having 6 to 30 carbon atoms for forming a ring, or substituted or unsubstituted heteroaryl group having 2 to 30 carbon atoms for forming a ring,
L' is substituted or unsubstituted arylene group having 6 to 30 carbon atoms for forming a ring, and
n is 0 or 1,
wherein when E is NR', m is 0, and when E is O or S, m is 1.

2. The polycyclic compound of claim 1, wherein Formula 3 is represented by the following Formula 5:

Formula 5

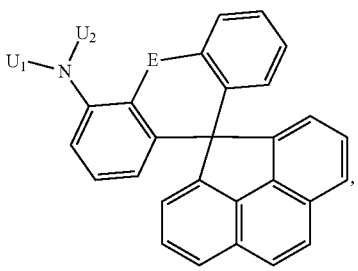

in Formula 5,
E, $U_1$ and $U_2$ are the same as defined in Formula 4.

3. The polycyclic compound of claim 1, wherein the polycyclic compound represented by Formula 3 is at least one selected from Compounds A-1 to A-23 (collectively denoted as Formula Group 1):

Formula Group 1

A-1

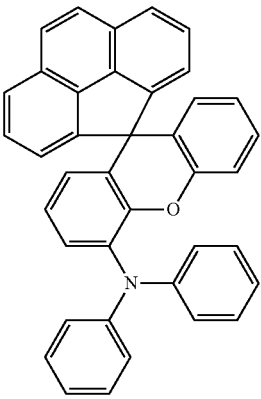

A-2
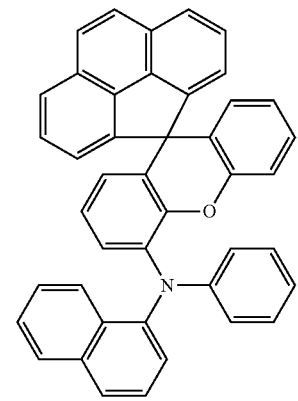
A-3
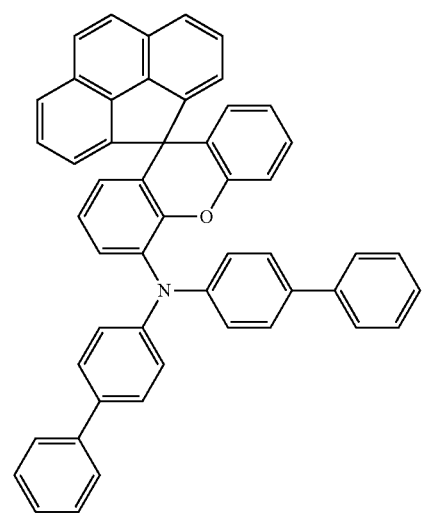
A-4
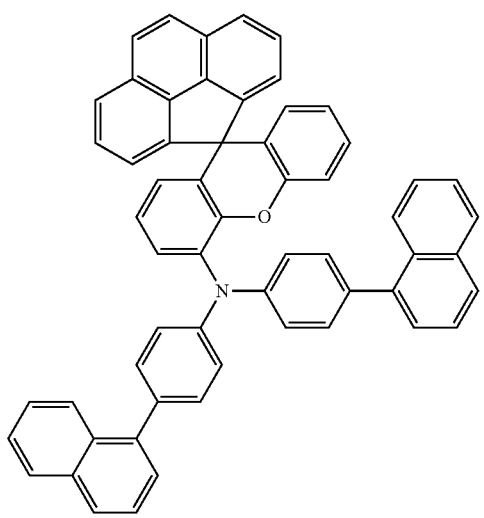
A-5
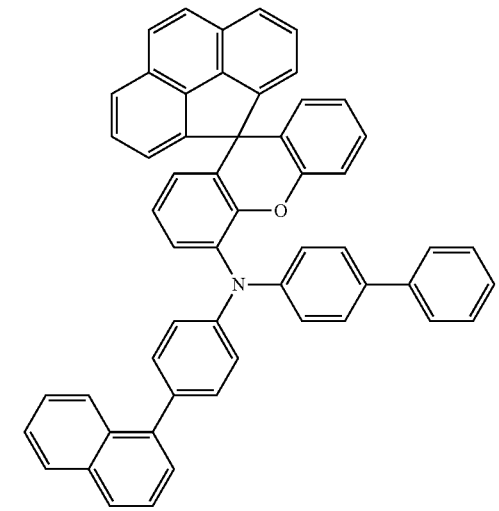
A-6
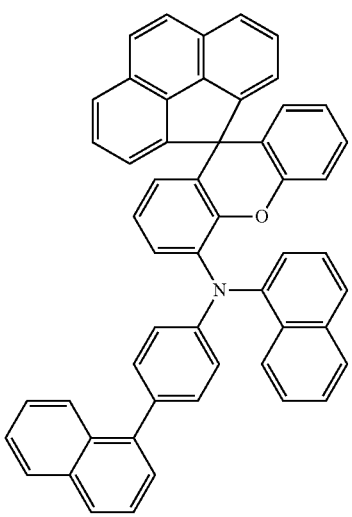
A-7
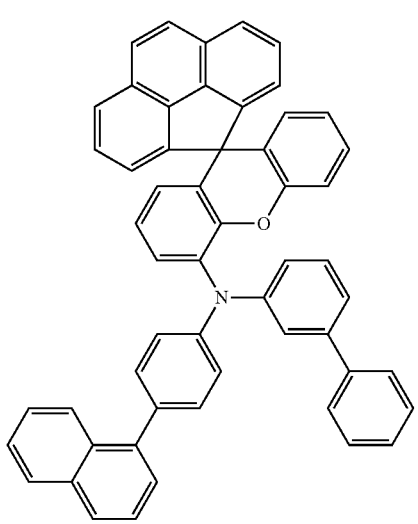

A-8
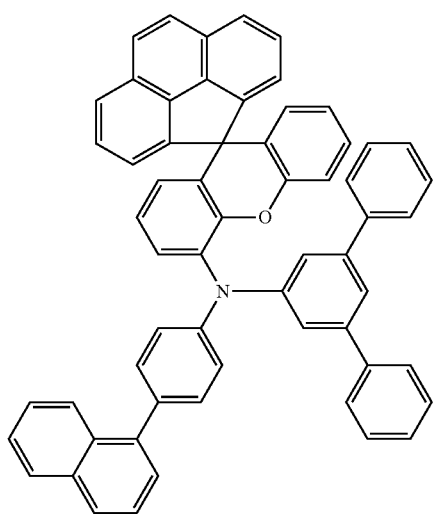
A-9
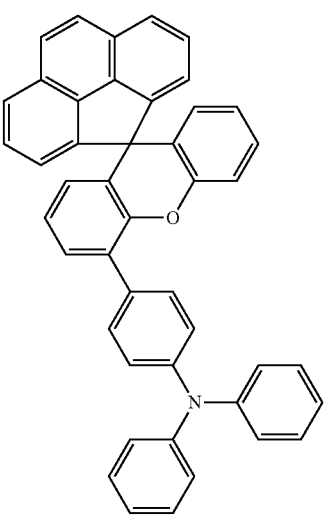
A-10
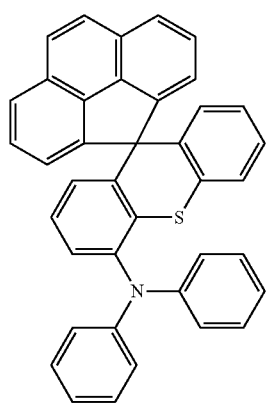
A-11
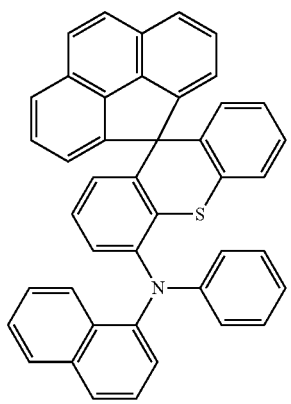
A-12
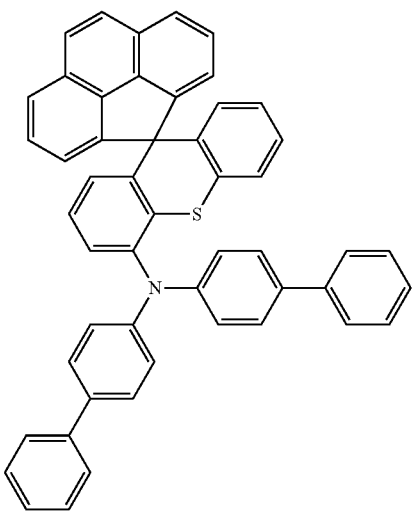
A-13
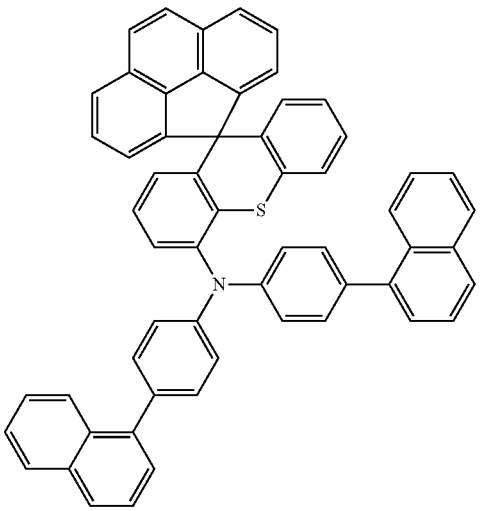

A-14
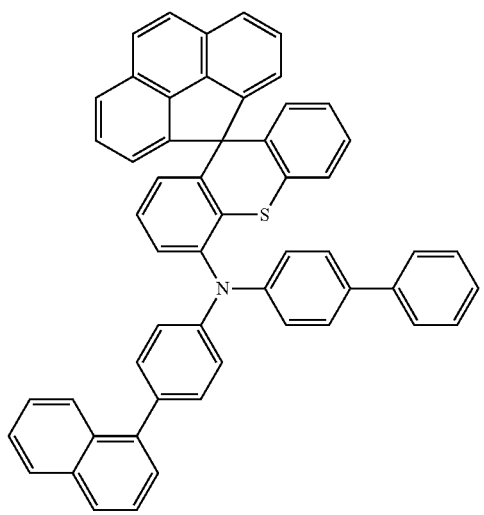
A-17
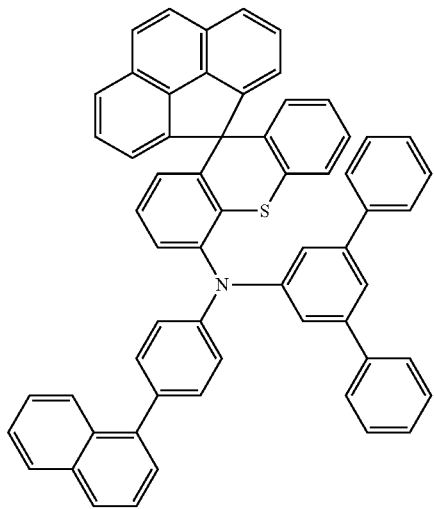
A-15
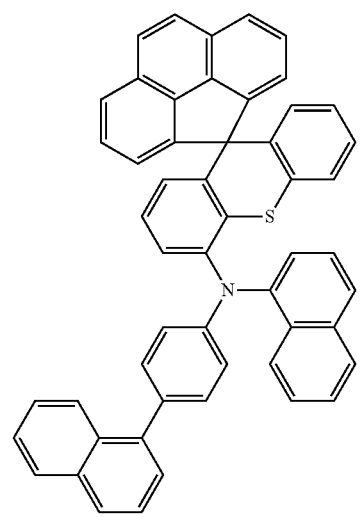
A-18
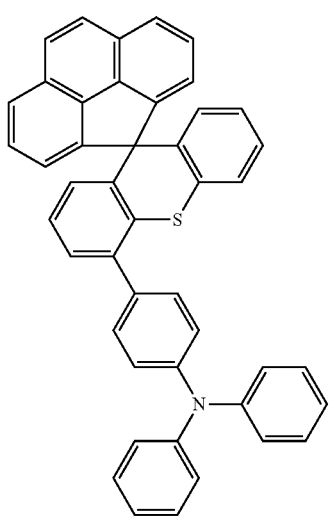
A-16
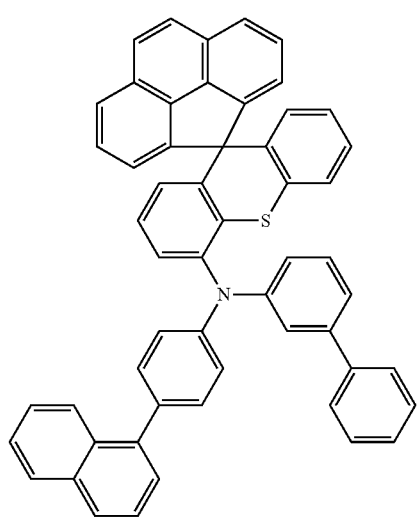
A-19
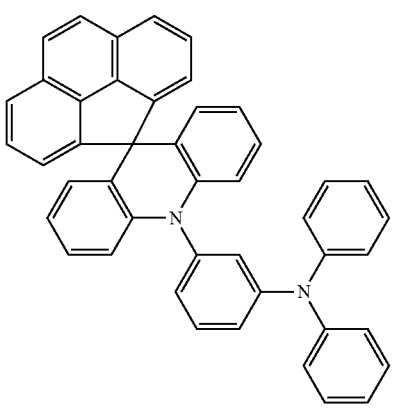

A-20
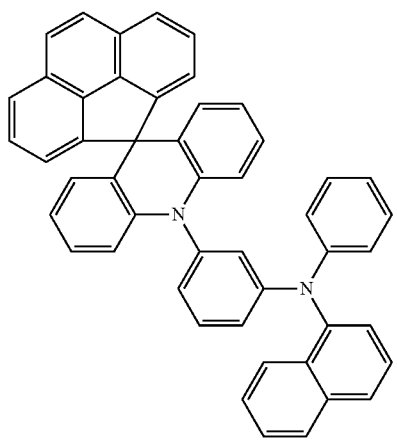
A-21
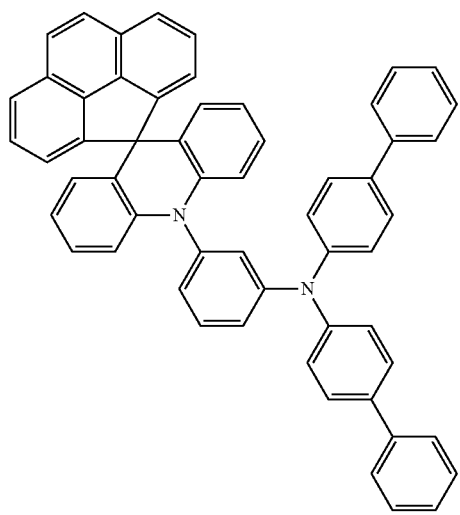
A-22
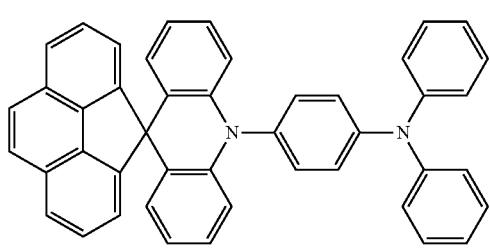
A-23
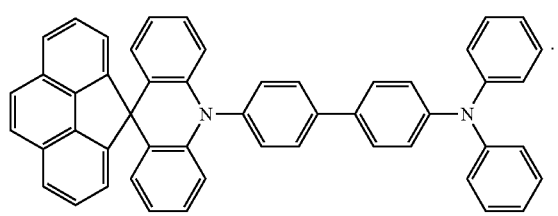
4. A polycyclic compound represented by one of the following Formulae 9 and 11-16:
Formula 9
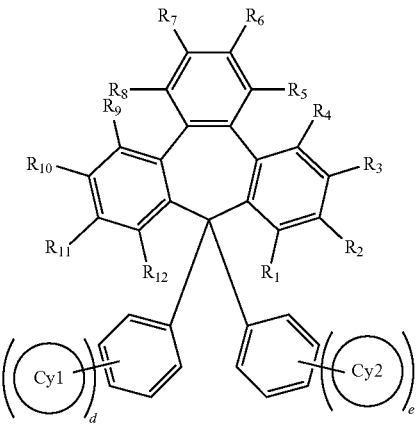
Formula 11
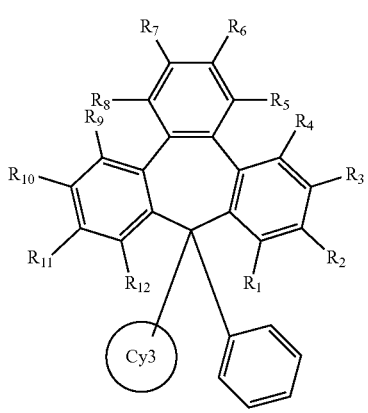
Formula 12
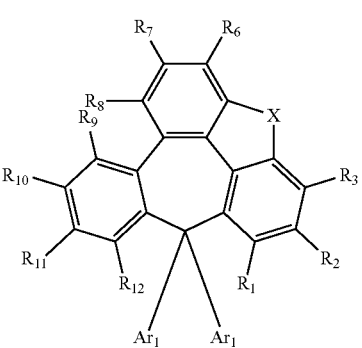
Formula 13
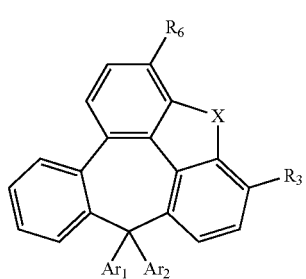

117
-continued

Formula 14

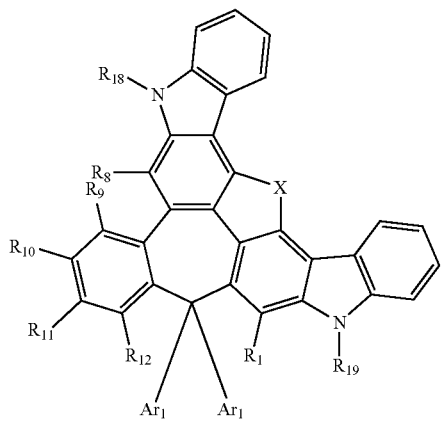

Formula 15

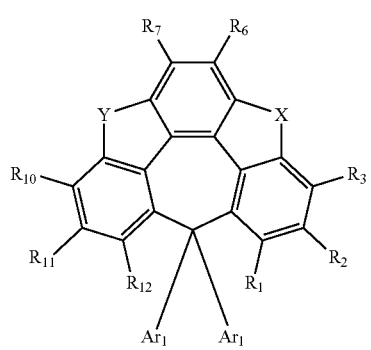

Formula 16

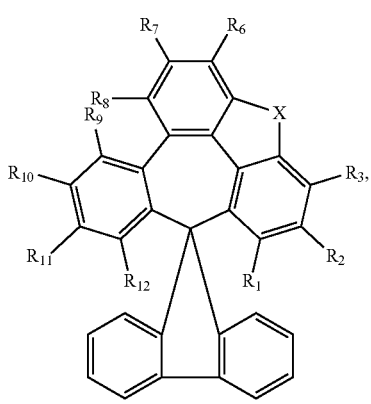

wherein in Formulae 9 and 11-16,
Cy1 and Cy2 are each independently substituted or unsubstituted heteroaryl group including 1 to 3 N atoms as heteroatoms and having 2 to 30 carbon atoms for forming a ring,
d and e are each independently 0 or 1, where the sum of d and e is not 0 (d+e≠0),
Cy3 is substituted or unsubstituted aryl group having a three- or four-membered ring,
X is O, S, $NR_{13}$, $CR_{14}R_{15}$, or $SiR_{16}R_{17}$,
Y is O, S, $NR_{20}$, or substituted or unsubstituted phosphine oxide,
$Ar_1$ and $Ar_2$ are each independently substituted or unsubstituted aryl group having 6 to 30 carbon atoms for forming a ring, or substituted or unsubstituted heteroaryl group having 2 to 30 carbon atoms for forming a ring, where $Ar_1$ and $Ar_2$ optionally combine with each other to form a ring,
$R_1$ to $R_{12}$ and $R_{13}$ to $R_{17}$ are each independently selected from hydrogen, deuterium, halogen, silyl group, substituted or unsubstituted alkyl group having 1 to 20 carbon atoms, substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, where adjacent groups selected from $R_1$ to $R_{12}$ optionally combine with each other to form a ring,
wherein in Formula 13, $R_3$ and $R_6$ are each independently selected from substituted or unsubstituted arylamine group, substituted or unsubstituted aryl group having 6 to 30 carbon atoms for forming a ring, and substituted or unsubstituted heteroaryl group having 2 to 30 carbon atoms for forming a ring, and
$R_{18}$ to $R_{20}$ are each independently selected from hydrogen, deuterium, substituted or unsubstituted aryl group having 6 to 30 carbon atoms for forming a ring, and substituted or unsubstituted heteroaryl group having 2 to 30 carbon atoms for forming a ring.

5. A polycyclic compound represented by at least one selected from Compounds 1, 2, 4-8, 10 to 50, 52 to 56, 58 to 60, 62 to 66 and 67 to 122 (collectively denoted as Formula Group 2 and Formula Group 3, respectively):

Formula Group 2

1

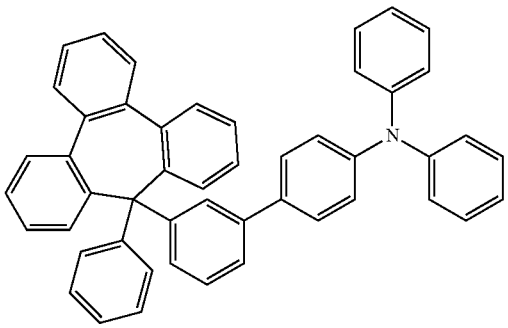

2

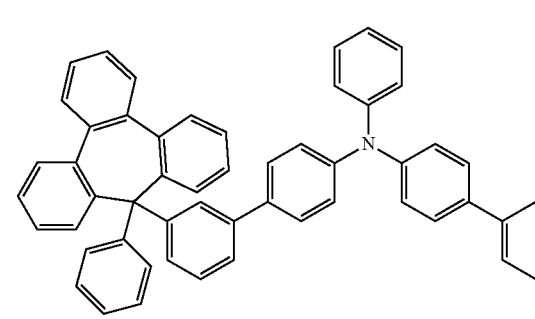

4

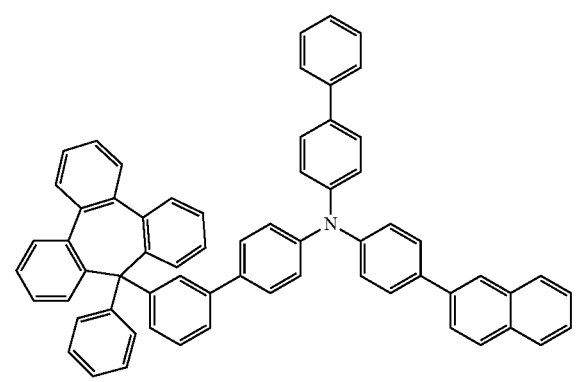

119
-continued
5
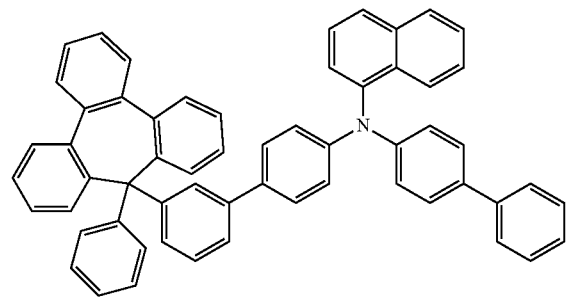
6
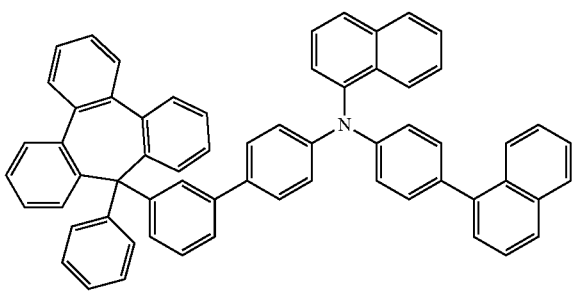
7
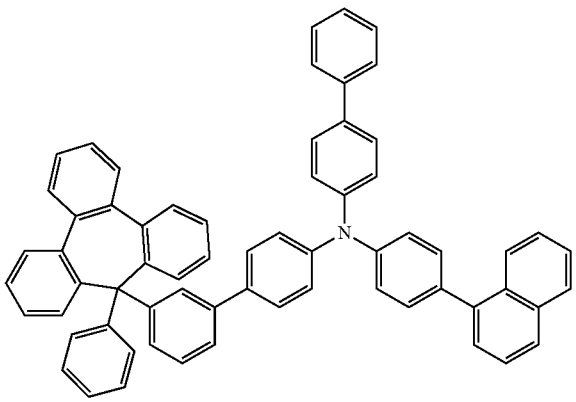
8
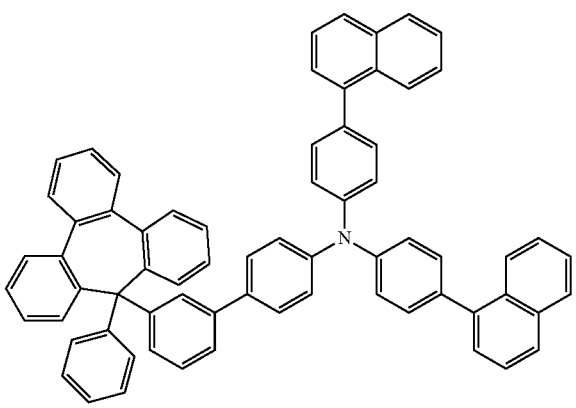
120
-continued
10
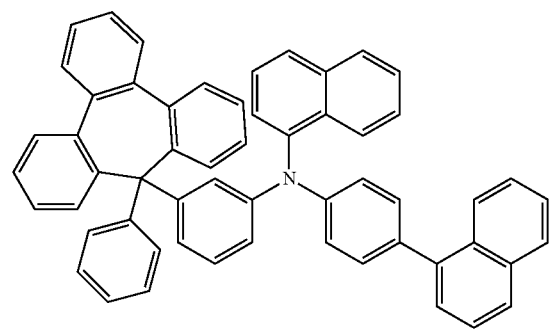
11
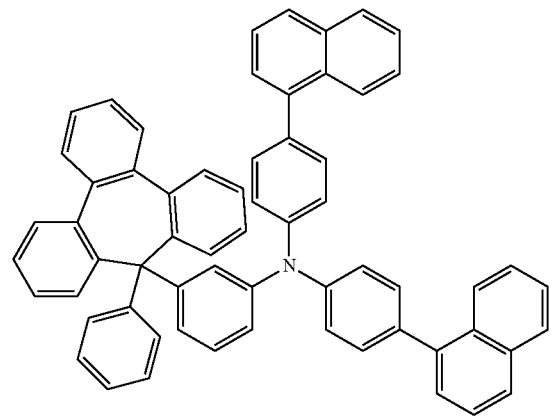
12
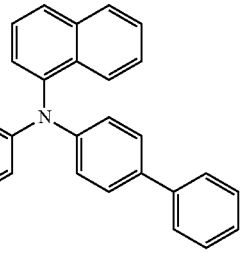
13

14
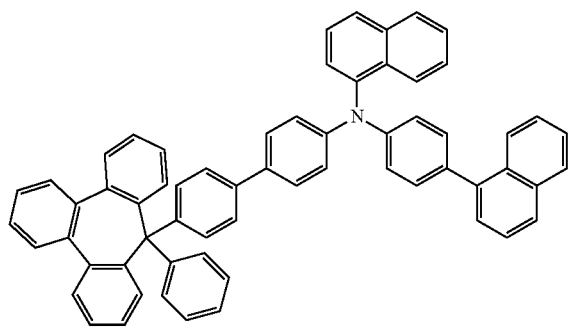
15
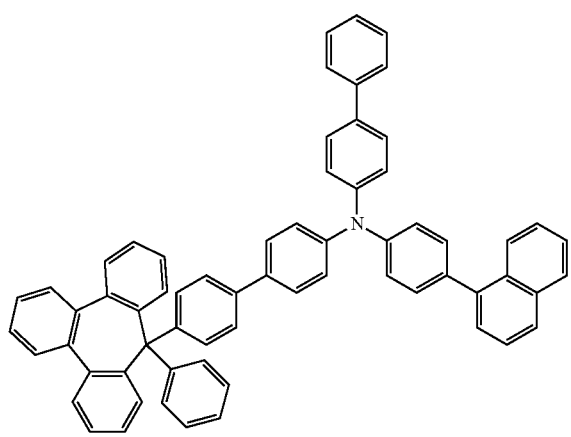
16
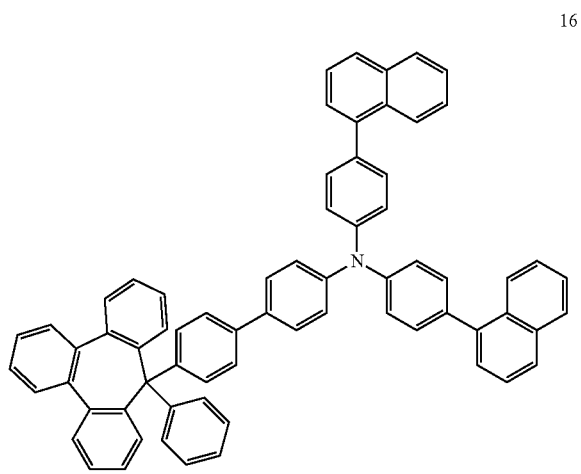
17
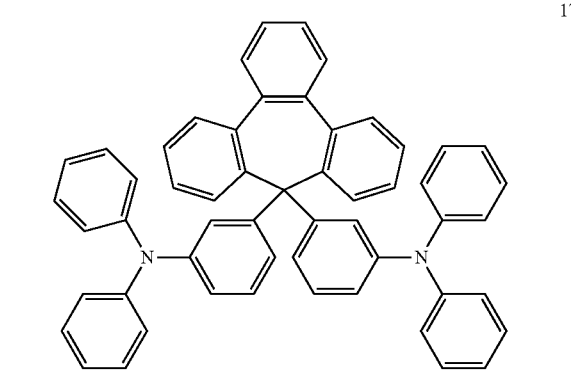
18
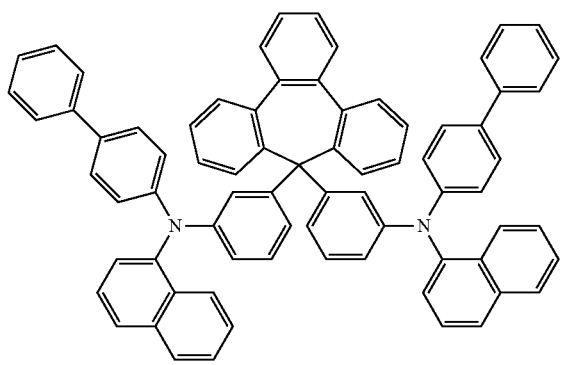
19
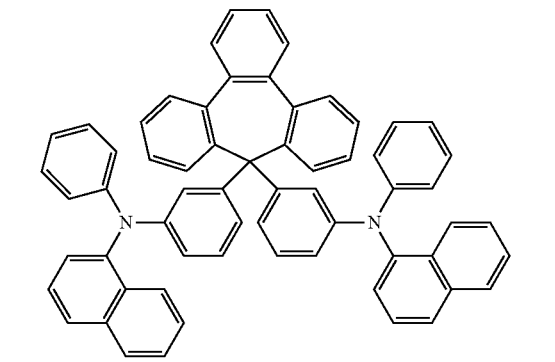
20
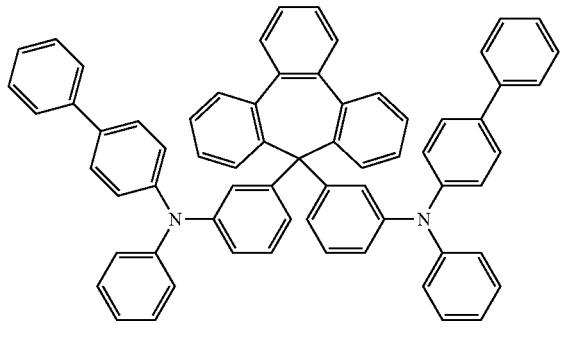
21
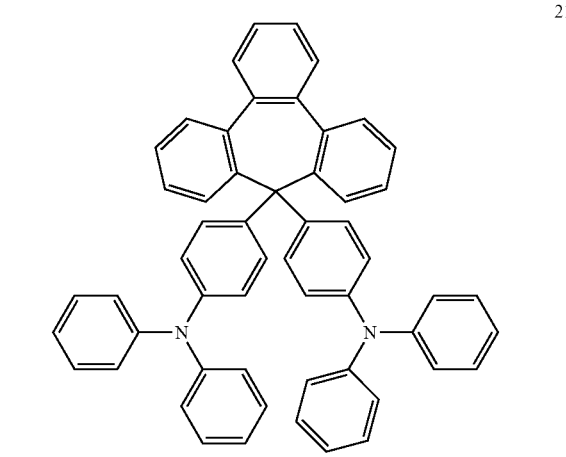

22
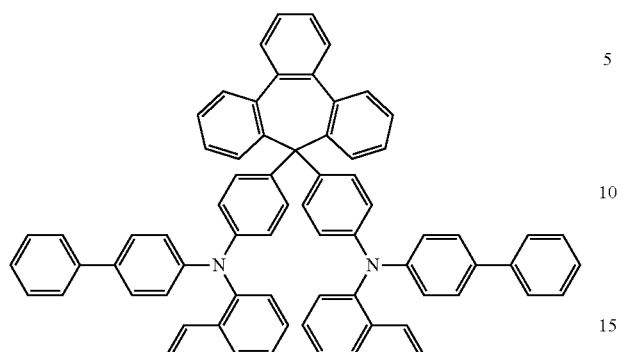
23
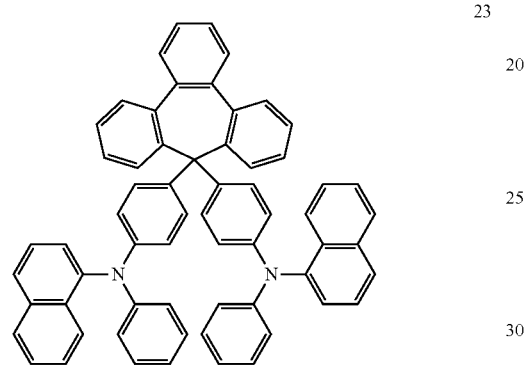
24
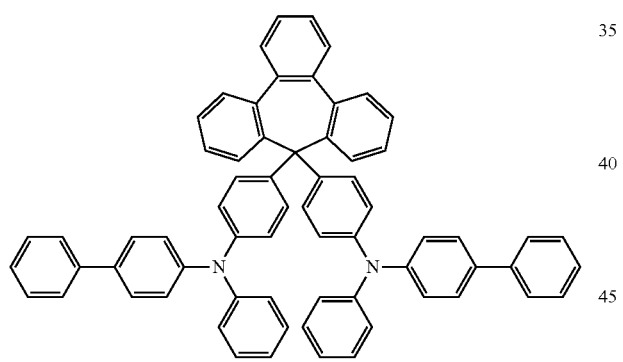
25
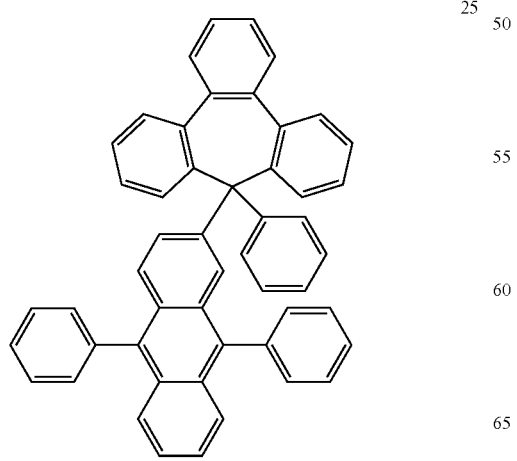
26
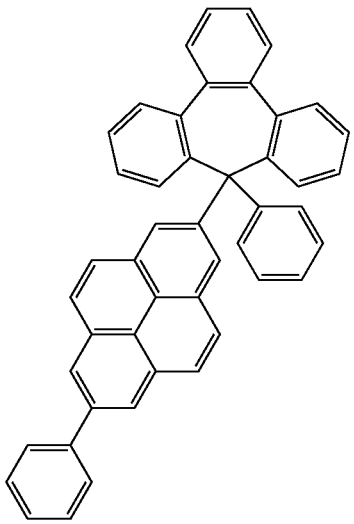
27
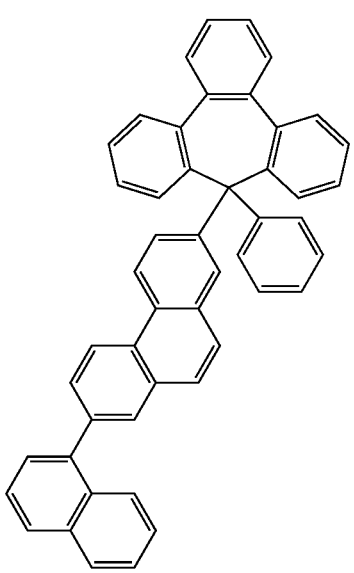
28
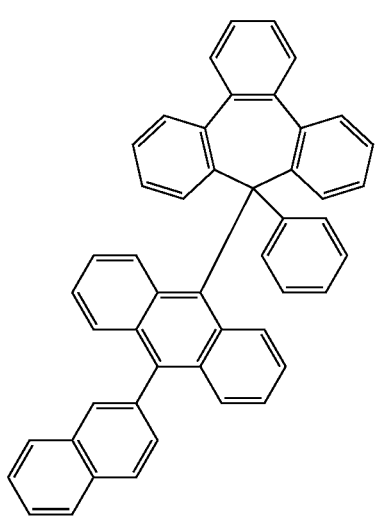

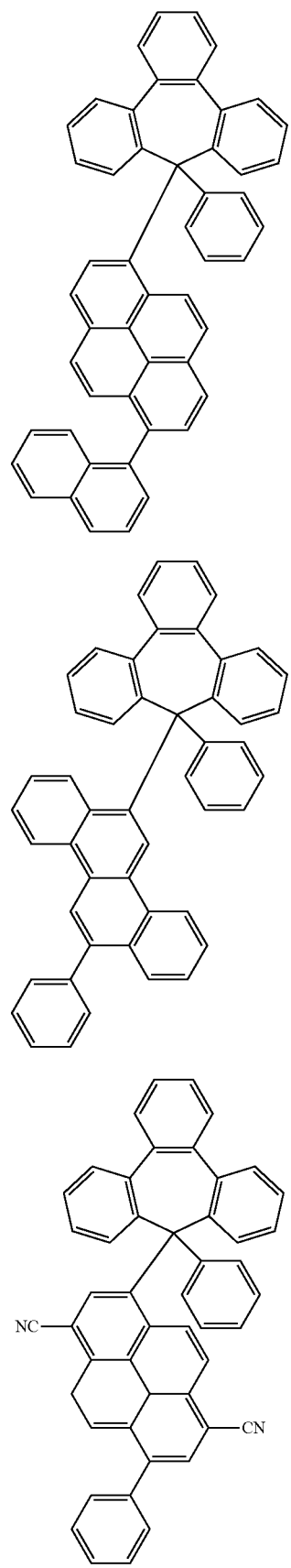
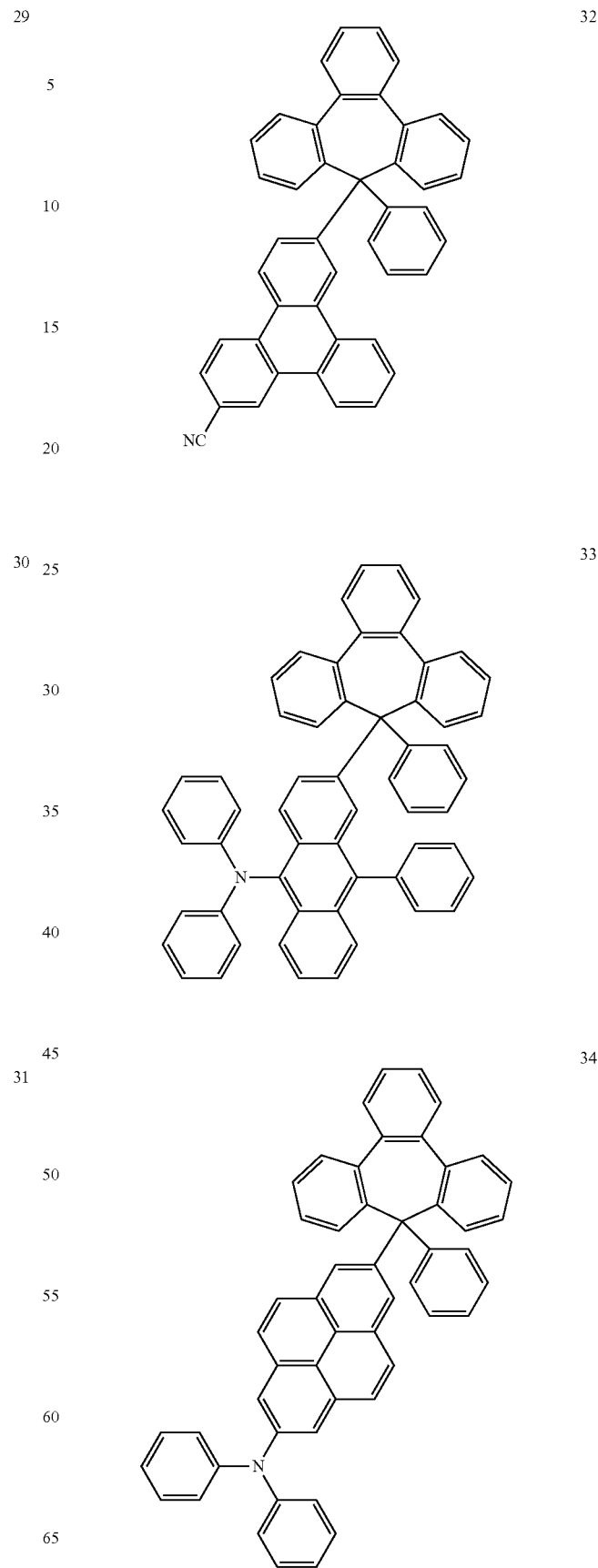

35
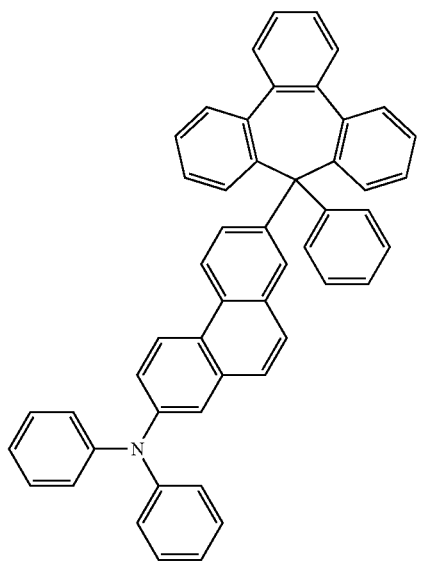
36
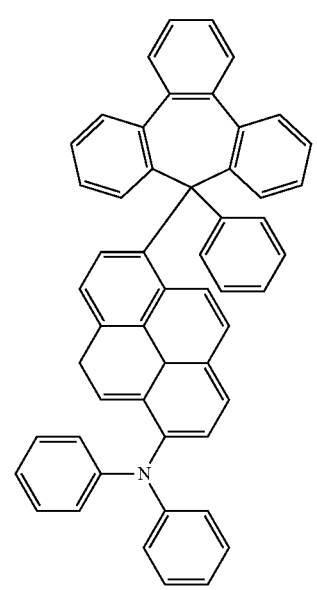
37
38
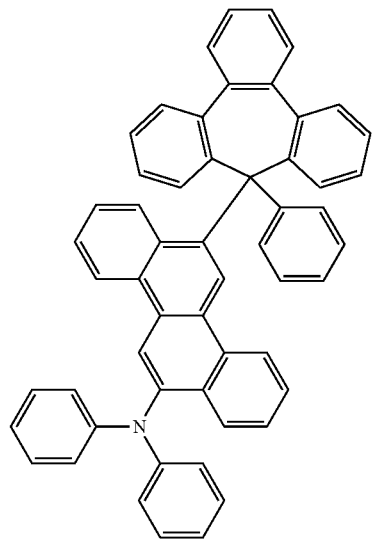
39
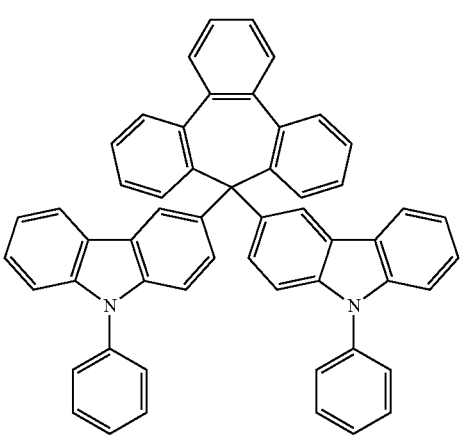
40

41
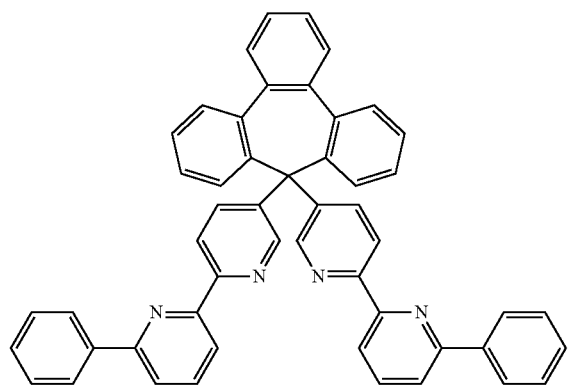
42
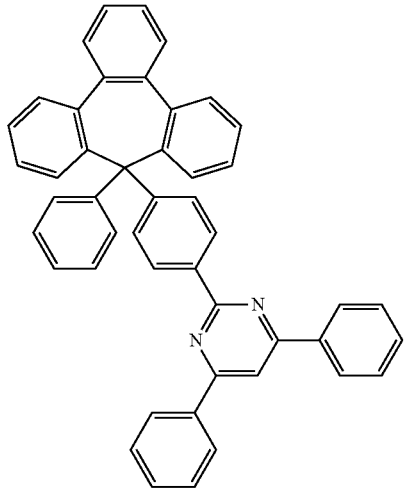
43
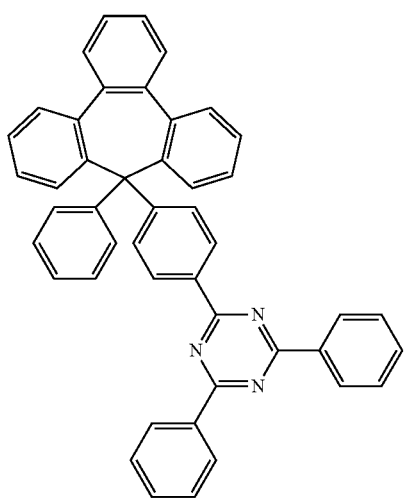
44
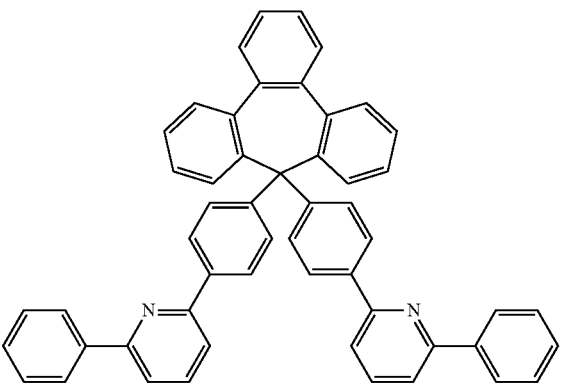
45
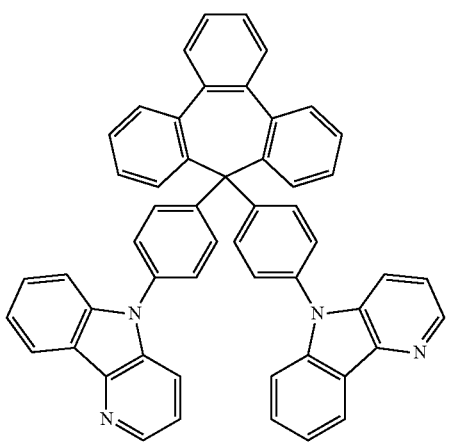
46
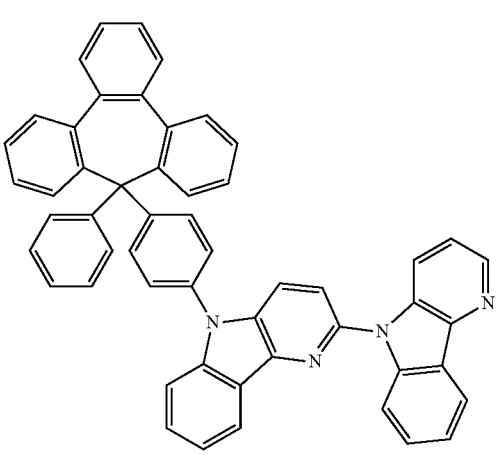

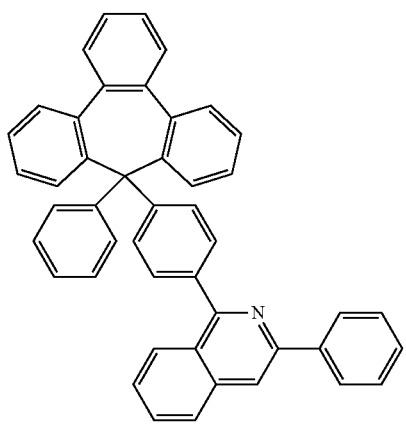
47
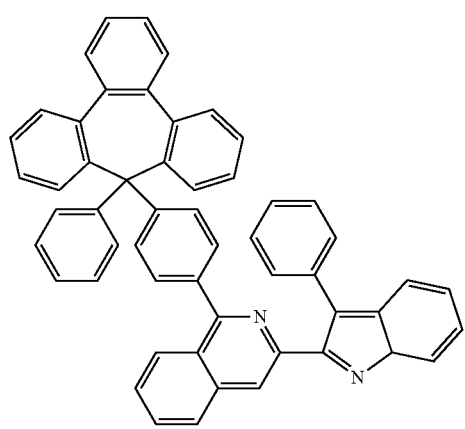
48
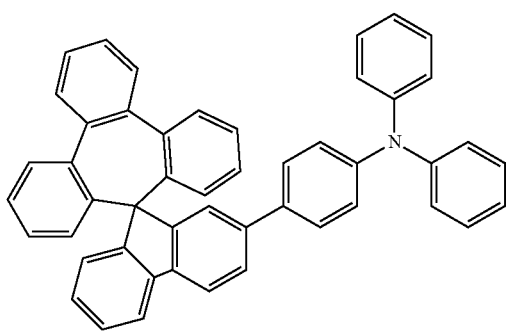
49
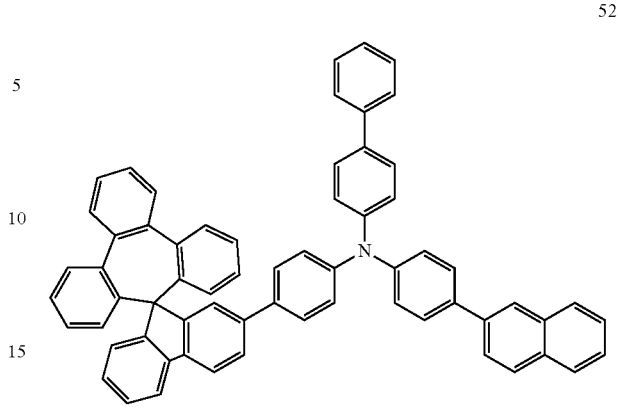
52
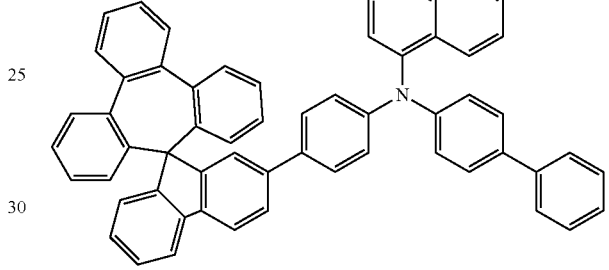
53
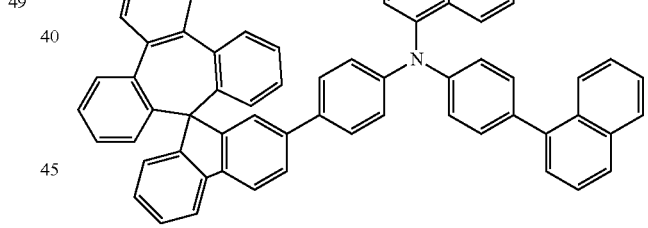
54
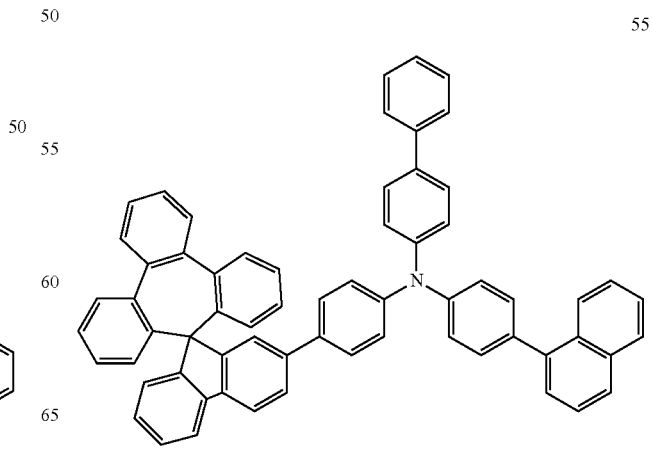
55

133
-continued
56
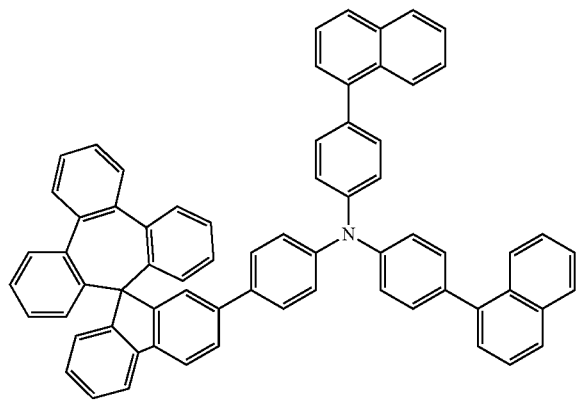
58
59
60
134
-continued
62
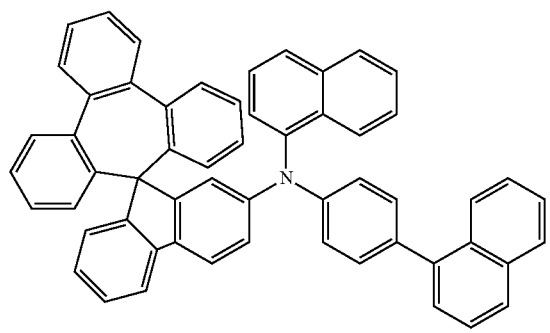
63
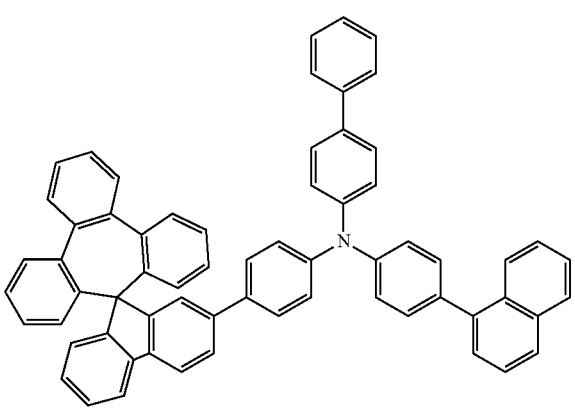
64
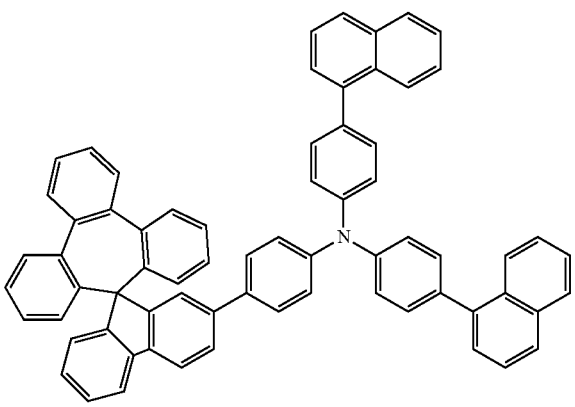
65
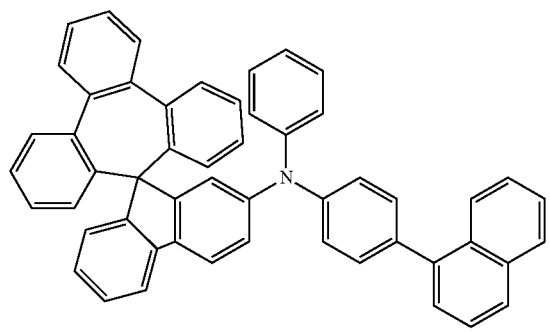

66
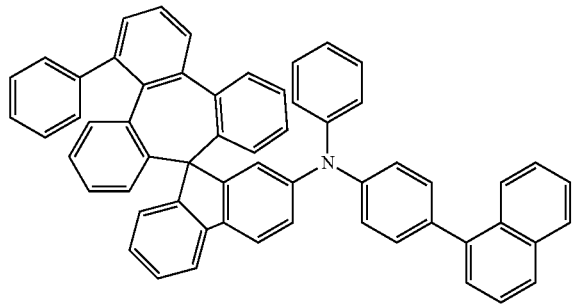
69
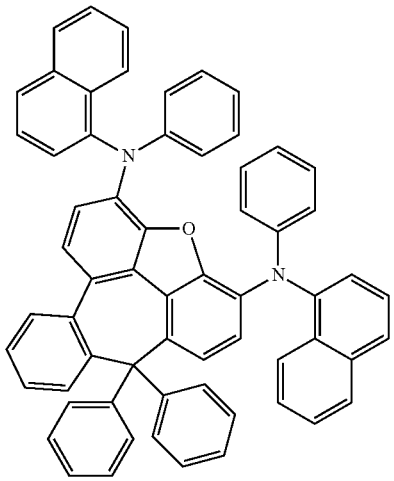
Formula Group 3
67
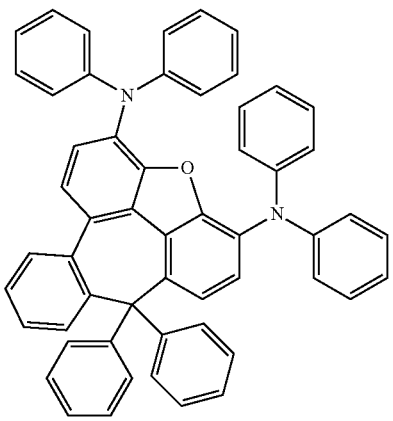
70
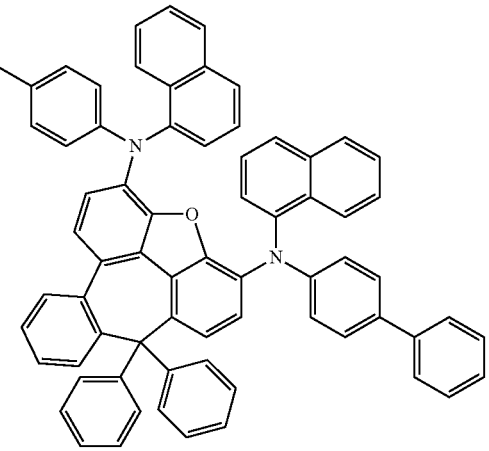
68
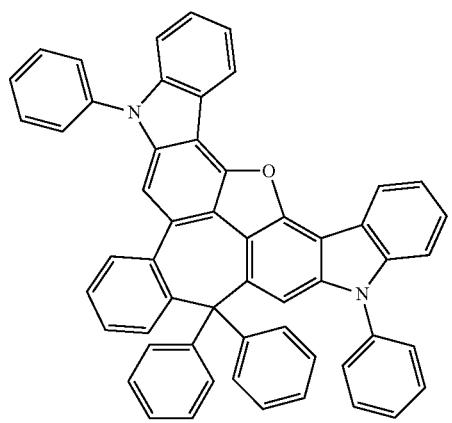
71
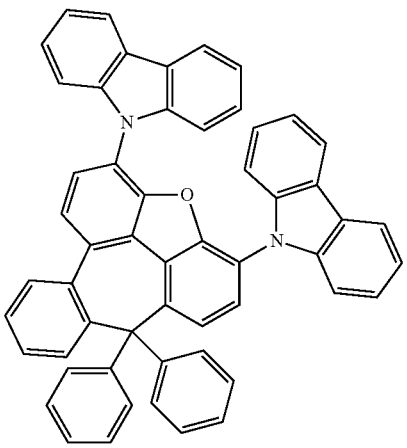

72
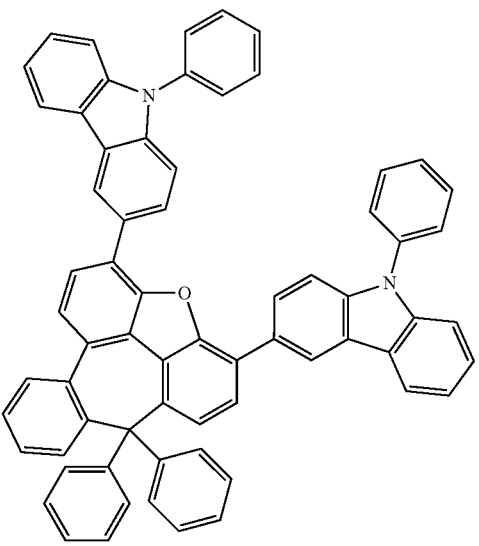
73
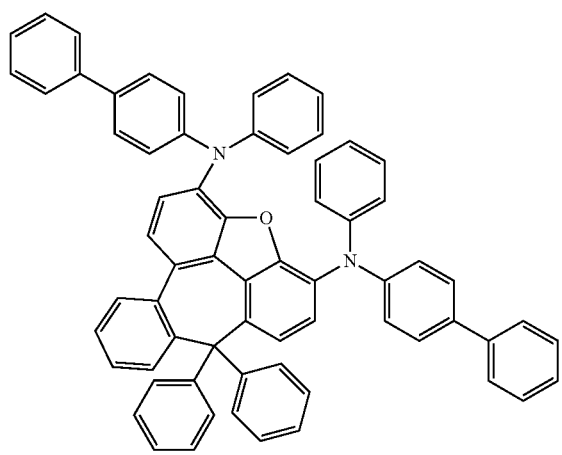
74
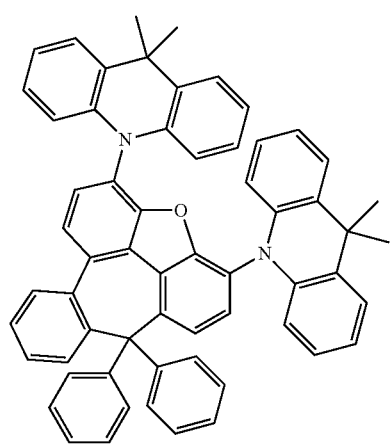
75
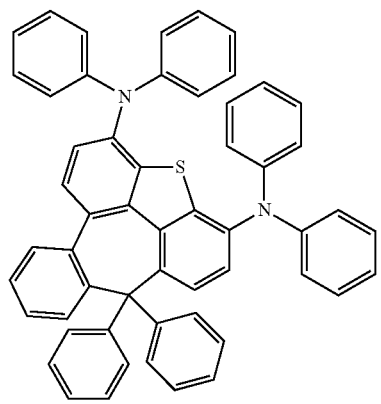
76
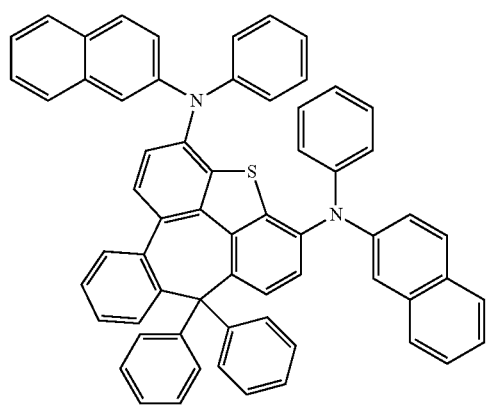
77
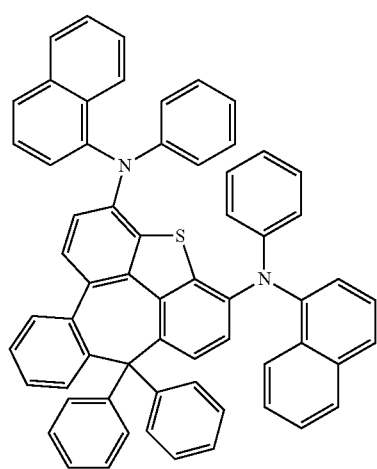

78
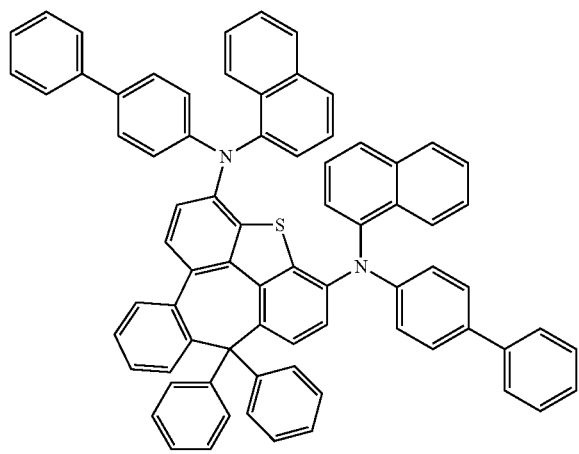
81
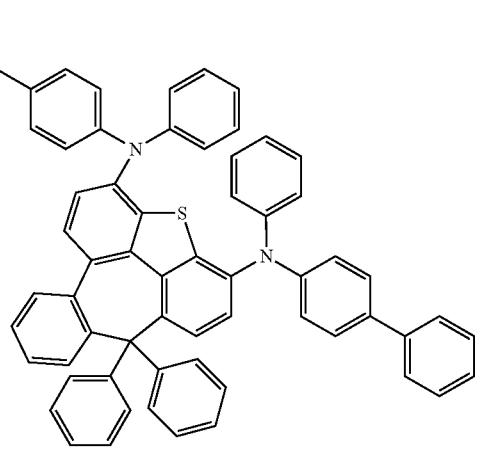
79
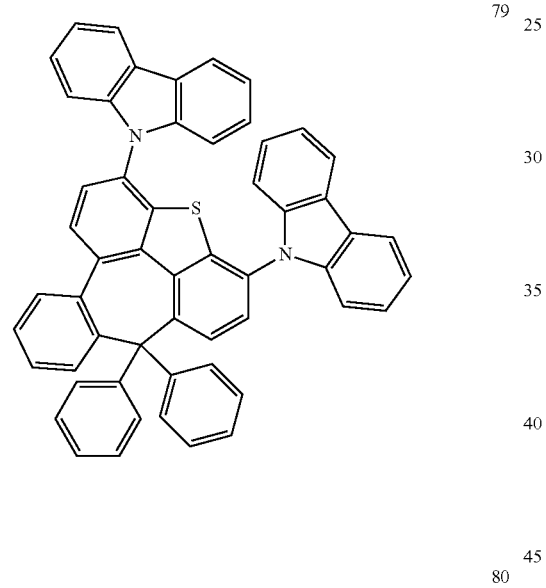
82
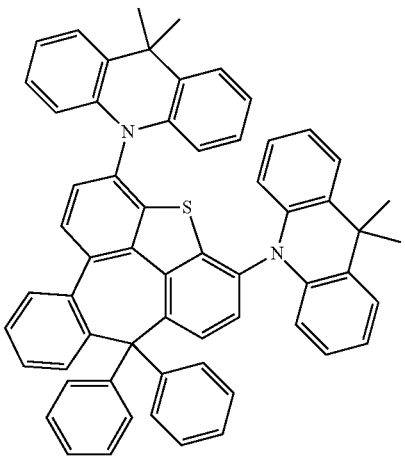
80
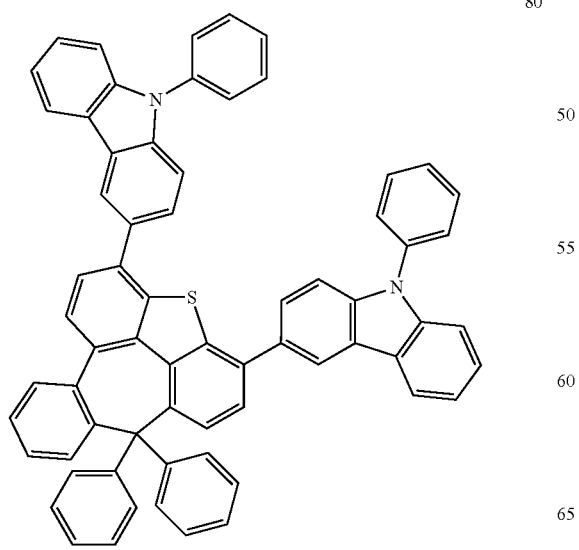
83
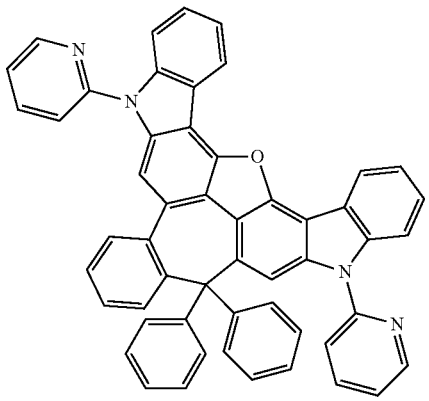

84
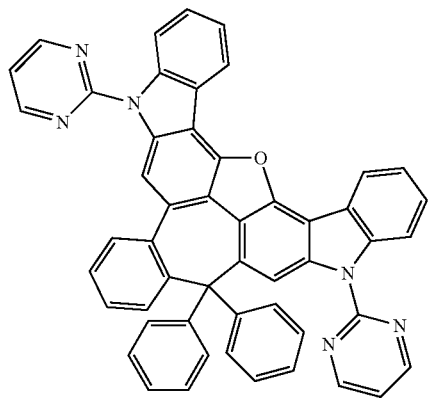
85
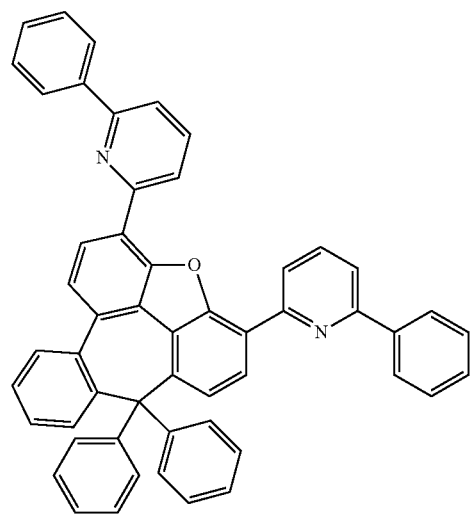
86
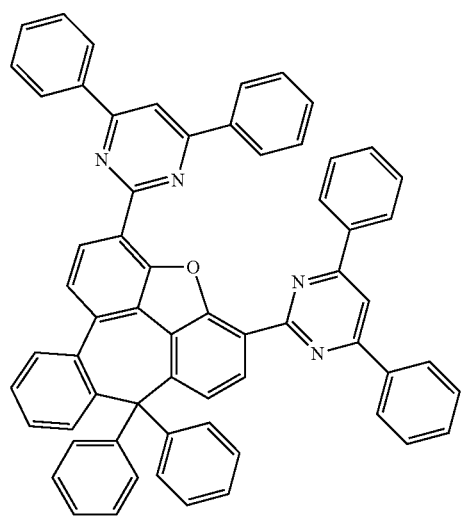
87
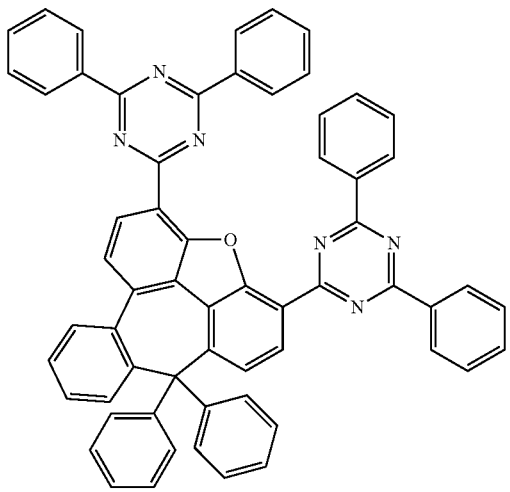
88
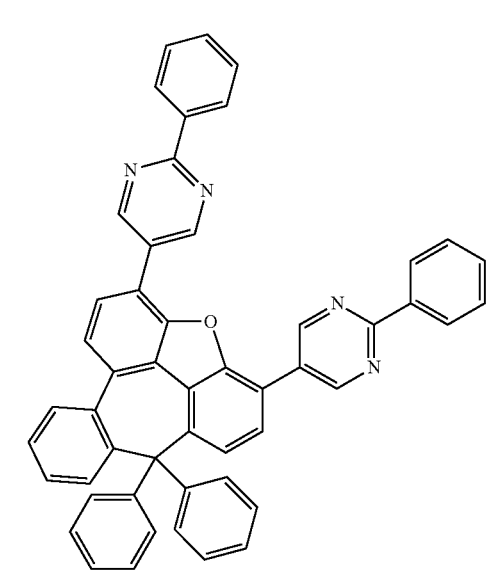
89
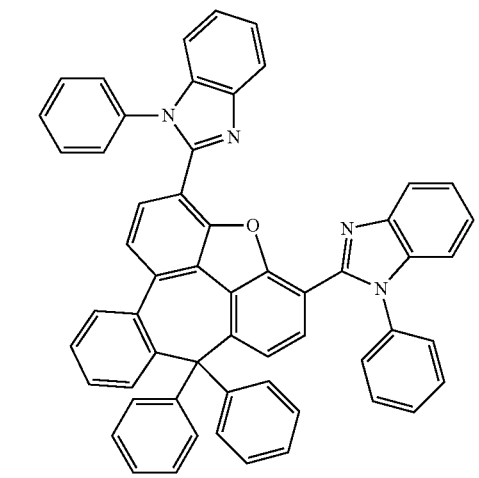

143
144
90
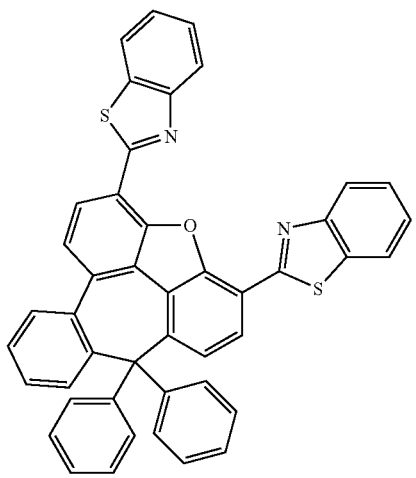
93
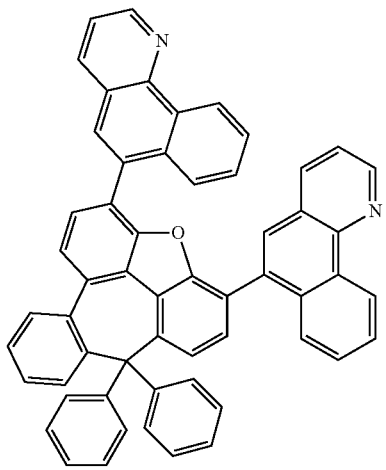
91
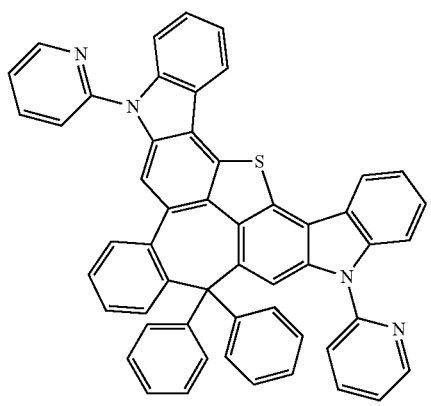
94
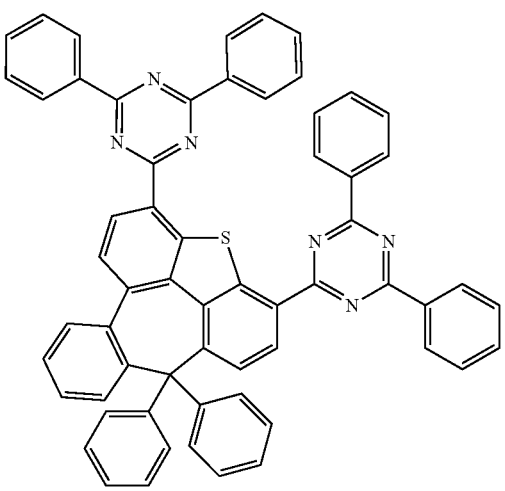
92
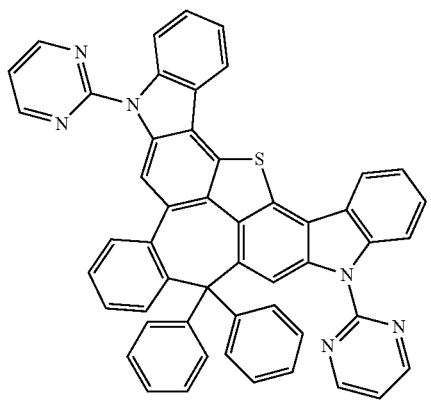
95

96
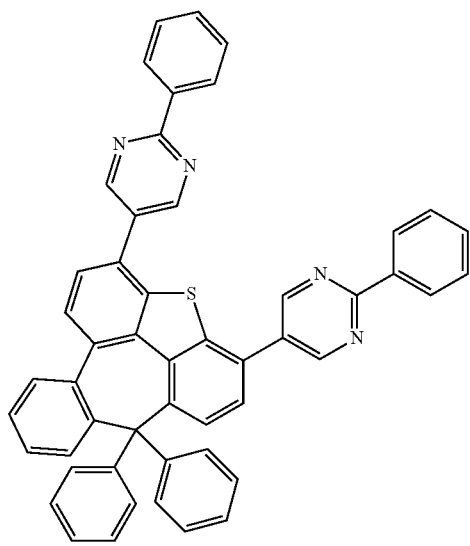
97
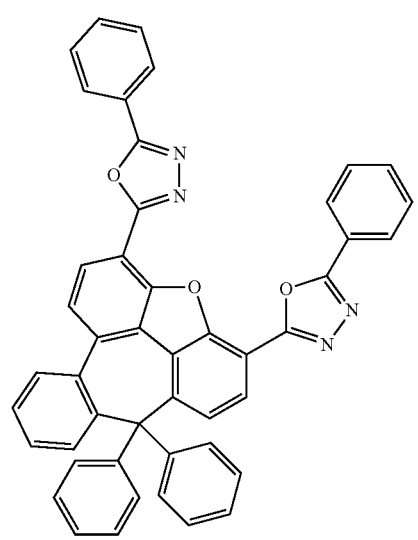
98
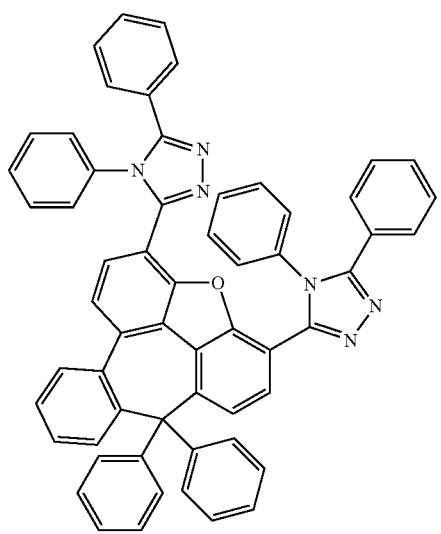
99
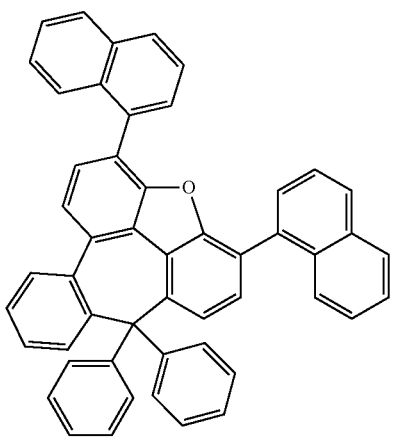
100
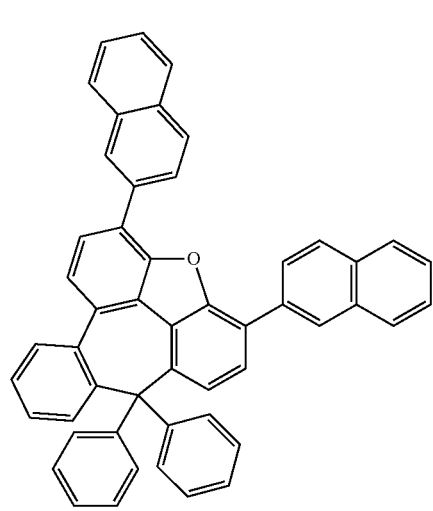
101
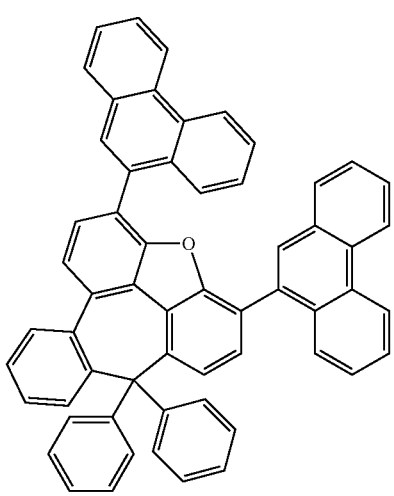

102
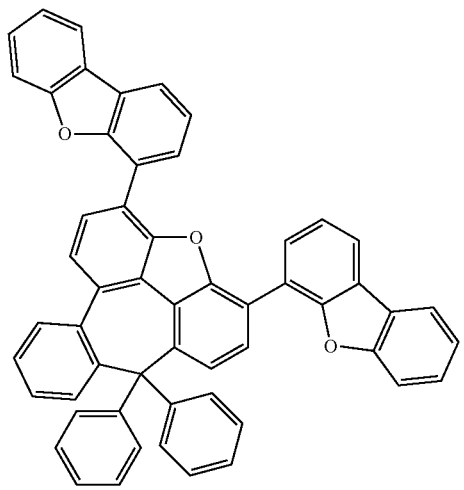
103
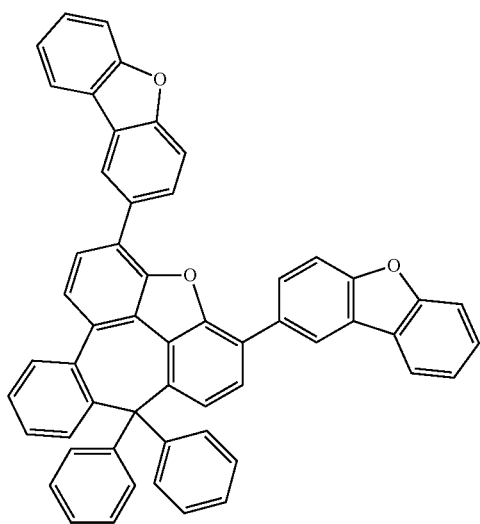
104
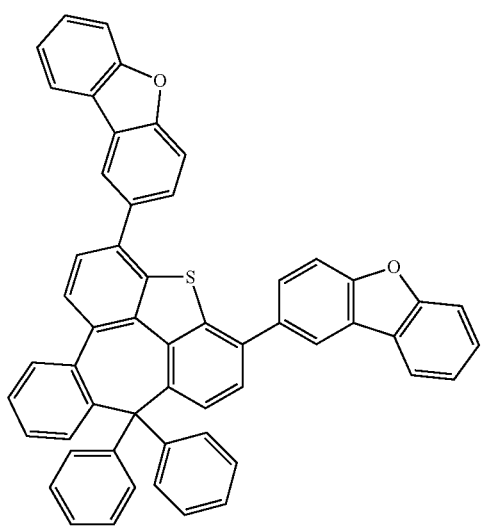
105
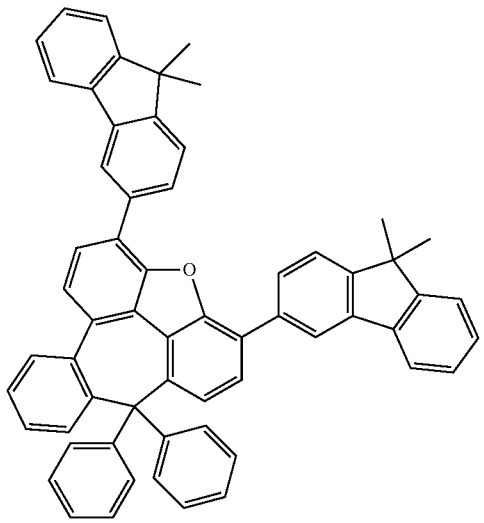
106
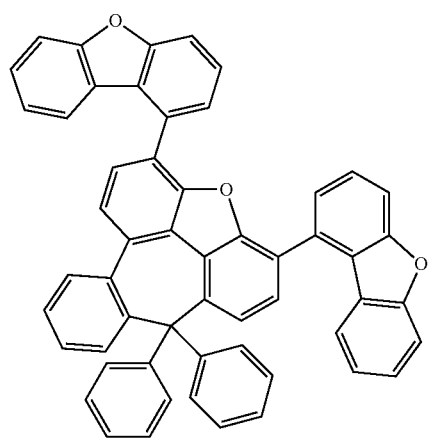
107
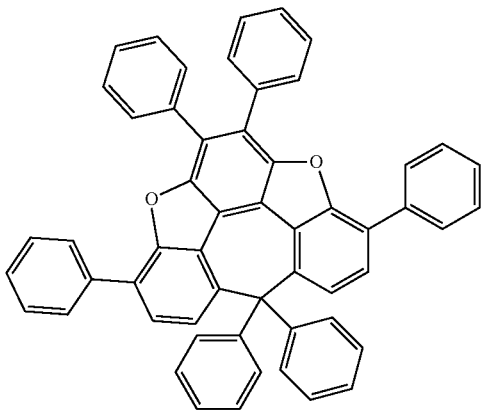

149
-continued
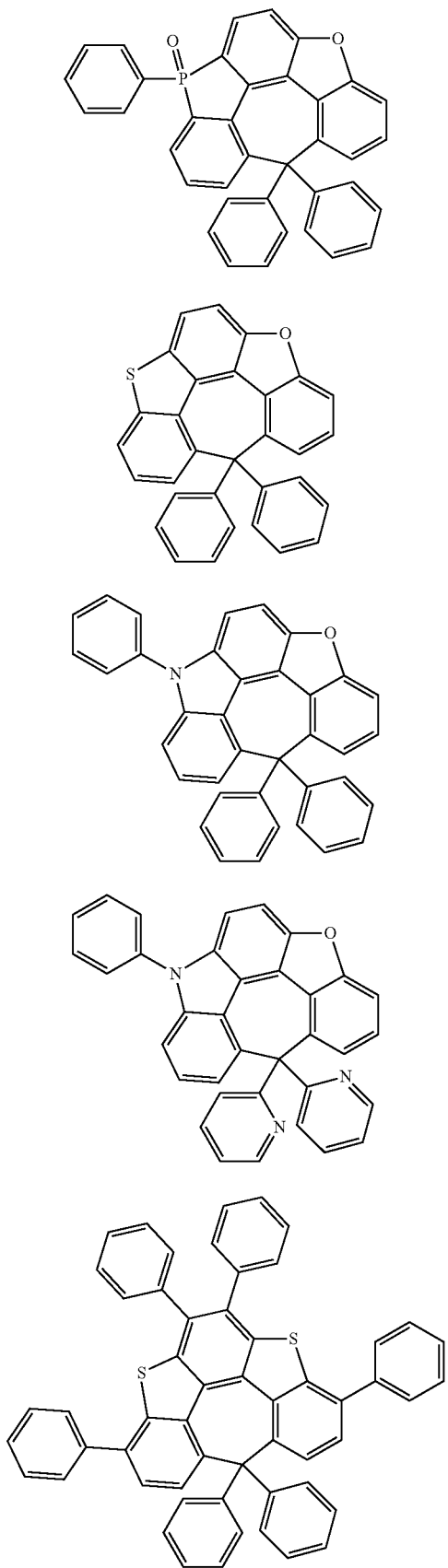
150
-continued
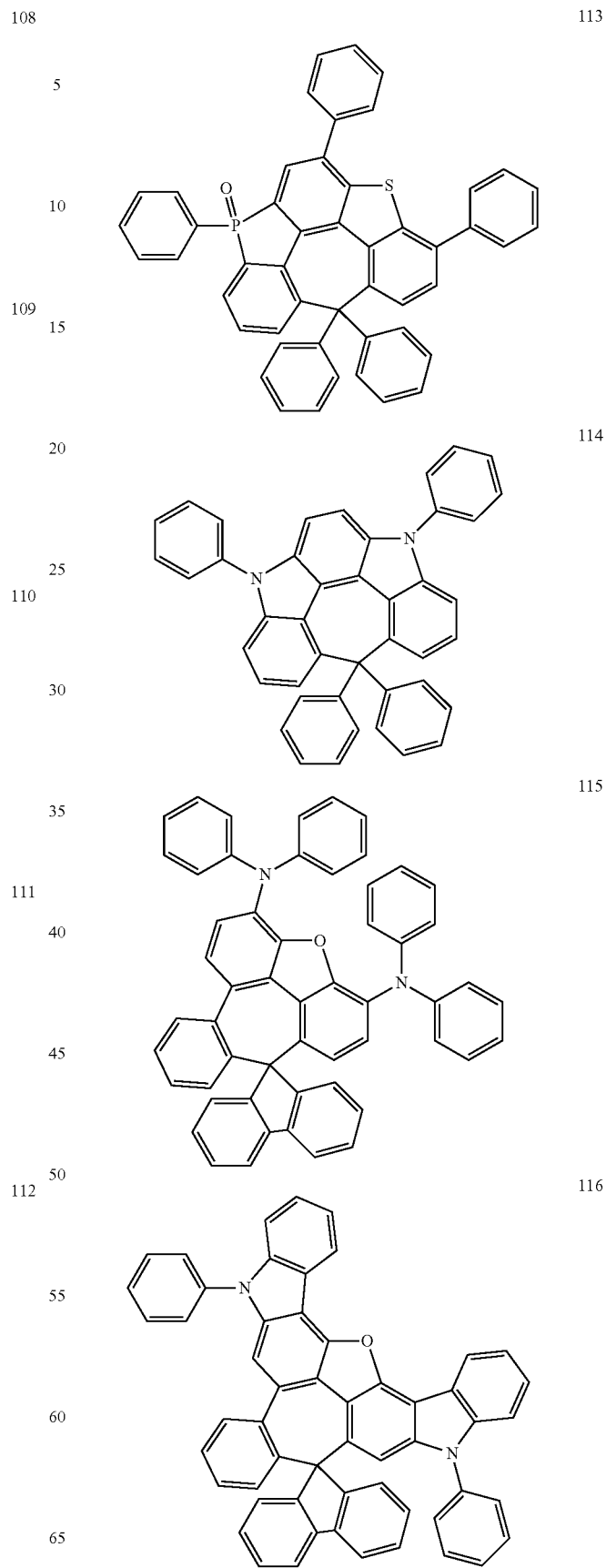

117

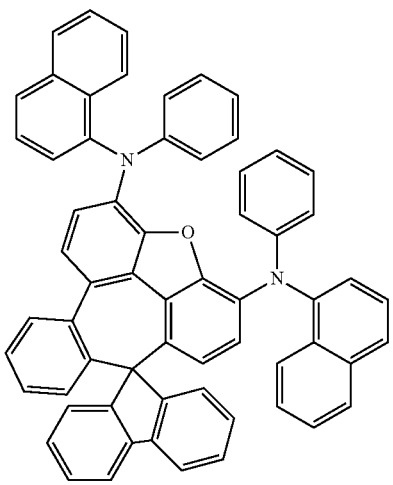

118

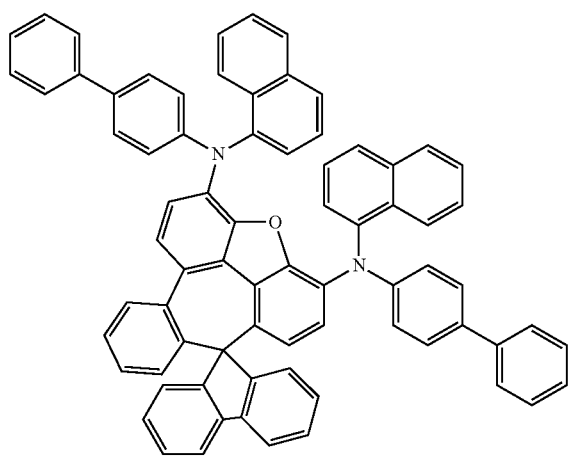

119

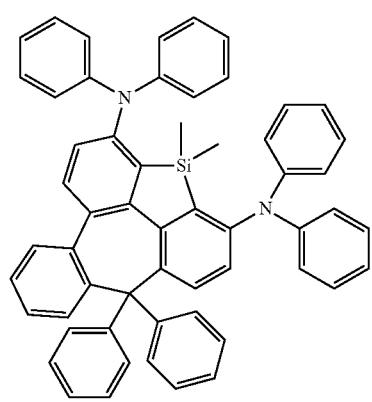

120

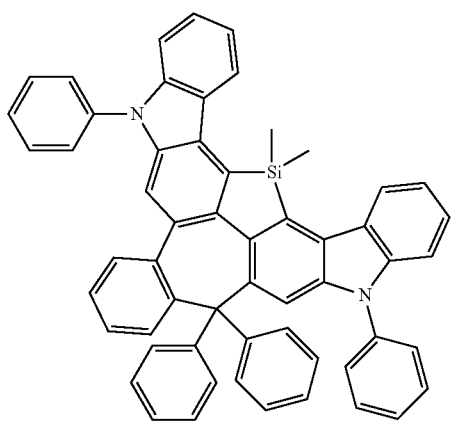

121

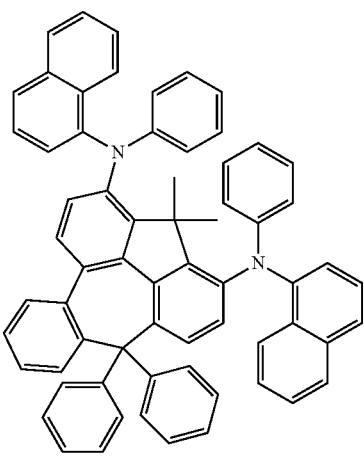

122

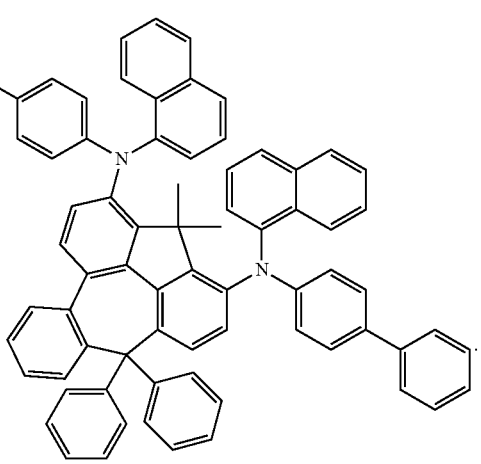

6. An organic electroluminescence device, comprising:
a first electrode;
a hole transport region on the first electrode;
an emission layer on the hole transport region;
an electron transport region on the emission layer; and
a second electrode on the electron transport region,
wherein at least one selected from the hole transport region and the emission layer comprises the polycyclic compound of claim 1.

7. The organic electroluminescence device of claim 6, wherein the polycyclic compound is at least one selected from Compounds A-1 to A-23 (collectively denoted as Formula Group 1):
Formula Group 1
A-1
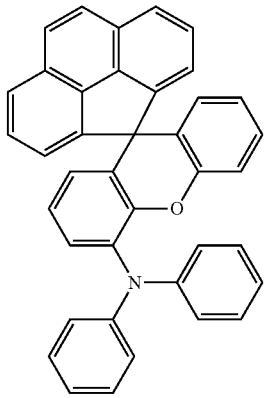
A-2
A-3
A-4
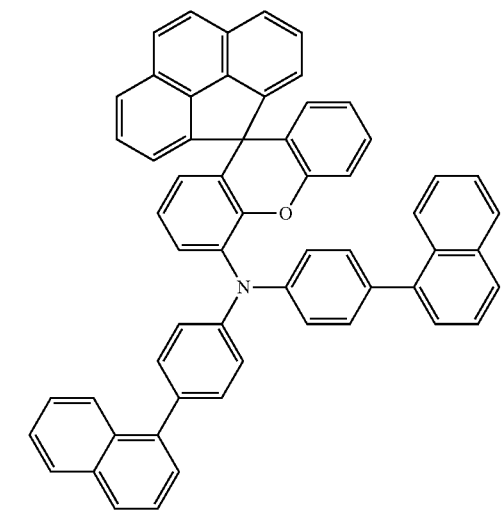
A-5
A-6
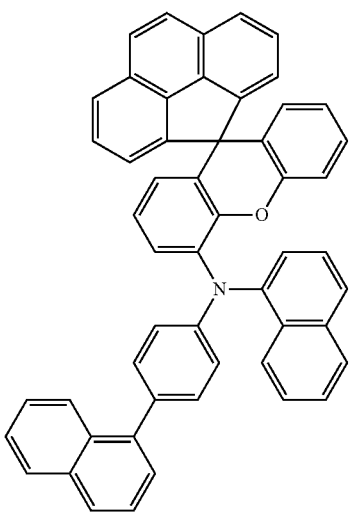
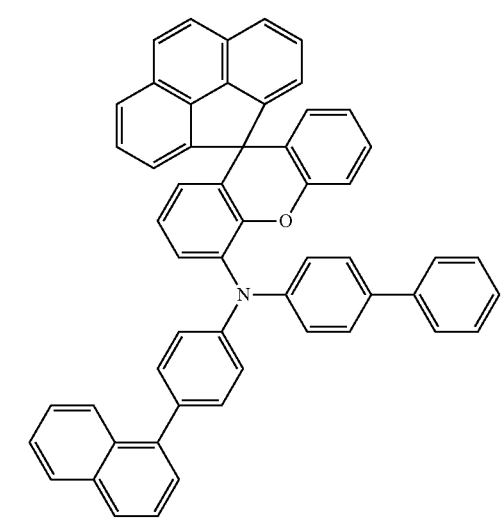

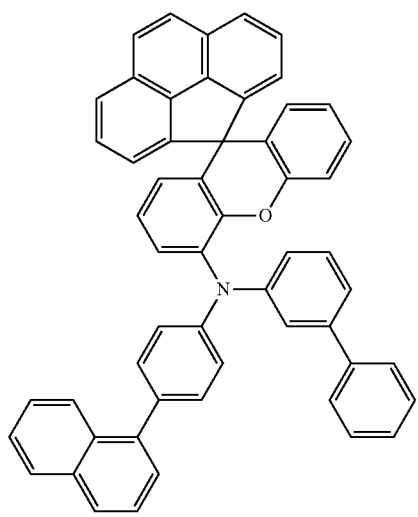
A-7
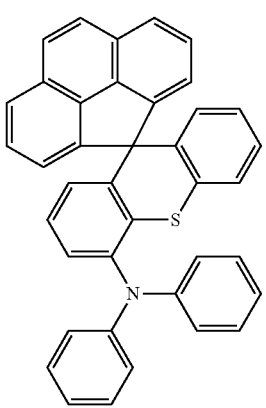
A-10
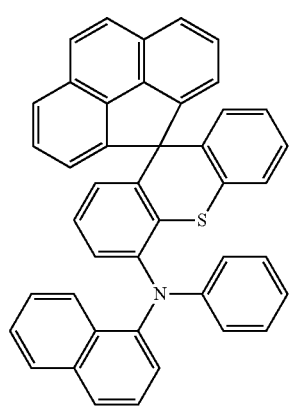
A-11
A-8
A-9
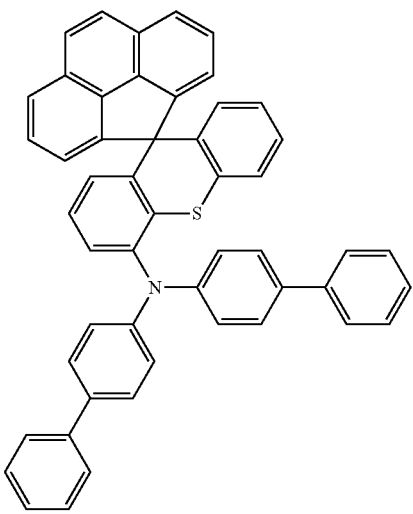
A-12

A-13
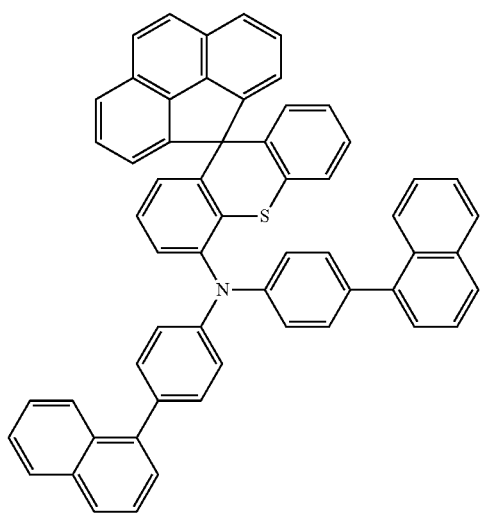
A-14
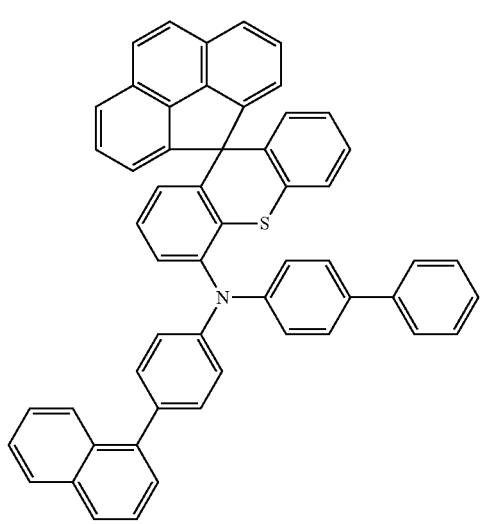
A-15
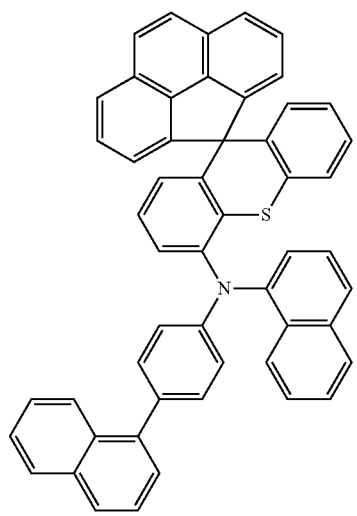
A-16
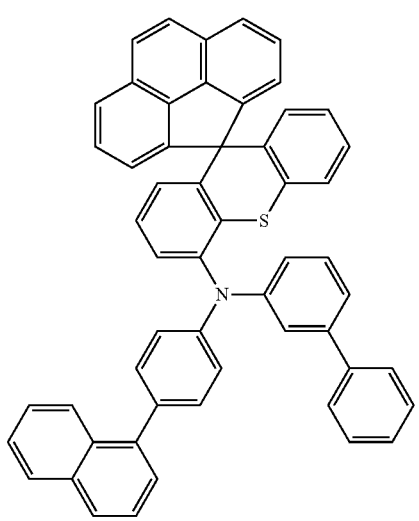

A-17
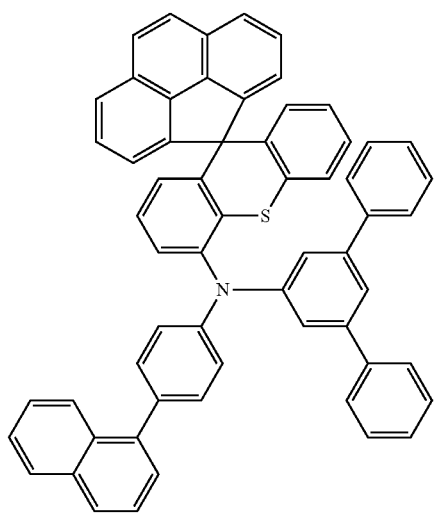
A-18
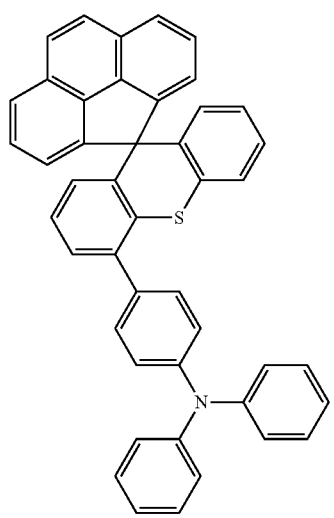
A-19
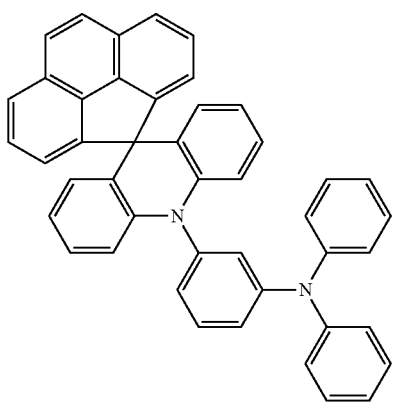
A-20
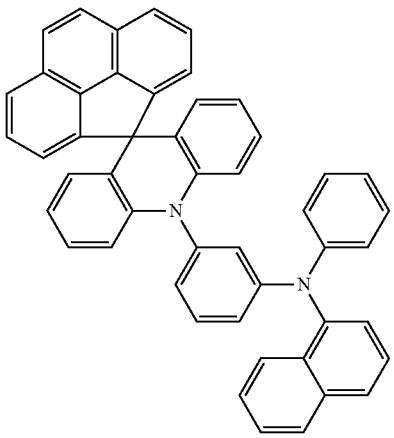
A-21
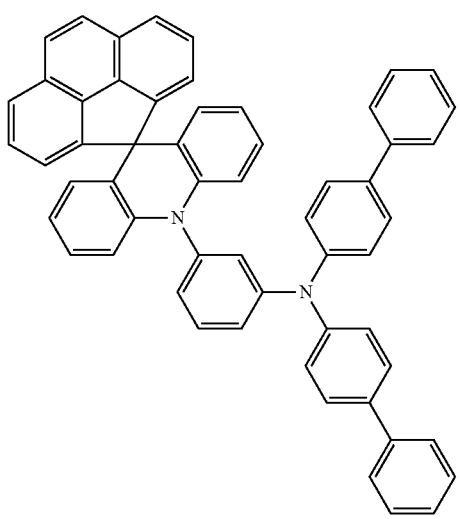
A-22
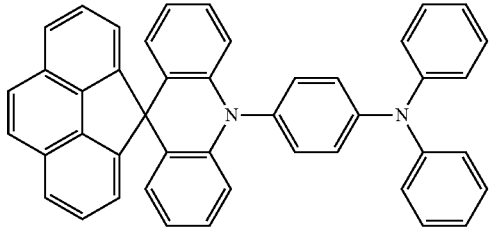
A-23
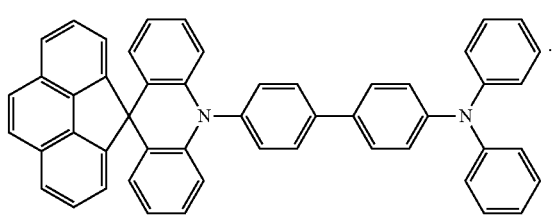
8. An organic electroluminescence device, comprising:
a first electrode;
a hole transport region on the first electrode;
an emission layer on the hole transport region;
an electron transport region on the emission layer; and
a second electrode on the electron transport region, wherein at least one selected from the hole transport region and the emission layer comprises the polycyclic compound of claim 4.

* * * * *